(12) United States Patent
Amir

(10) Patent No.: US 12,161,831 B2
(45) Date of Patent: Dec. 10, 2024

(54) MICRONEEDLES AND COMPOSITIONS FOR SKIN AUGMENTATION

(71) Applicant: Avraham Amir, Tel Mond (IL)

(72) Inventor: Avraham Amir, Tel Mond (IL)

(73) Assignee: Avraham Amir, Tel Mond (IL)

( * ) Notice: Subject to any disclaimer, the term of this patent is extended or adjusted under 35 U.S.C. 154(b) by 465 days.

(21) Appl. No.: 16/571,199

(22) Filed: Sep. 16, 2019

(65) Prior Publication Data

US 2020/0009364 A1 Jan. 9, 2020

Related U.S. Application Data

(63) Continuation-in-part of application No. PCT/IL2019/050032, filed on Jan. 6, 2019, and a
(Continued)

(51) Int. Cl.
*A61M 37/00* (2006.01)
*A61K 9/00* (2006.01)
*A61K 33/42* (2006.01)
*A61K 47/02* (2006.01)
*A61K 47/10* (2017.01)
*A61P 17/00* (2006.01)

(52) U.S. Cl.
CPC ........ *A61M 37/0015* (2013.01); *A61K 9/0021* (2013.01); *A61K 33/42* (2013.01); *A61K 47/02* (2013.01); *A61K 47/10* (2013.01); *A61P 17/00* (2018.01); *A61M 2037/0023* (2013.01); *A61M 2037/0046* (2013.01); *A61M 2037/0061* (2013.01)

(58) Field of Classification Search
CPC .... A61M 2037/0023; A61M 2037/003; A61M 2037/0038
See application file for complete search history.

(56) References Cited

U.S. PATENT DOCUMENTS 7,655,250 B2 2/2010 Mansouri
8,167,852 B2 5/2012 Quan
(Continued)

FOREIGN PATENT DOCUMENTS

CN 104434561 A 3/2015
CN 106421929 A 2/2017
(Continued)

OTHER PUBLICATIONS

Fukamizu et al. (2012) Development of a three-microneedle device for hypodermic drug delivery and clinical application. Plast Reconstr Surg 130(2): 451-5.
(Continued)

*Primary Examiner* — Courtney B Fredrickson
(74) *Attorney, Agent, or Firm* — Mark Cohen; PEARL COHEN ZEDEK LATZER BARATZ LLP

(57) ABSTRACT

The present invention provides microneedles for administration of biocompatible materials effective in augmentation of skin or other skin treatments, and applicators comprising such microneedles. In particular, the microneedles and applicators of the present invention are aimed at filling the undesired lines, wrinkles, depressed scars and folds of a subject's facial and neck skin and restoring youthful fullness to the skin.

17 Claims, 30 Drawing Sheets

Related U.S. Application Data continuation-in-part of application No. 14/427,309, filed as application No. PCT/IL2013/050510 on Jun. 13, 2013, now Pat. No. 10,420,921.

(60) Provisional application No. 62/614,418, filed on Jan. 7, 2018, provisional application No. 61/725,498, filed on Nov. 13, 2012, provisional application No. 61/721,037, filed on Nov. 1, 2012, provisional application No. 61/700,371, filed on Sep. 13, 2012.

(56) References Cited

U.S. PATENT DOCUMENTS

| | | | |
|---|---|---|---|
| 2002/0020688 A1* | 2/2002 | Sherman | B26F 1/24 216/2 |
| 2002/0156453 A1 | 10/2002 | Pettis et al. | |
| 2006/0177494 A1 | 8/2006 | Cormier | |
| 2007/0078414 A1* | 4/2007 | McAllister | A61B 17/205 604/232 |
| 2007/0260201 A1 | 11/2007 | Prausnitz et al. | |
| 2008/0213461 A1 | 4/2008 | Gill | |
| 2008/0262444 A1 | 10/2008 | Takad | |
| 2010/0125288 A1 | 5/2010 | Gelfand et al. | |
| 2010/0221314 A1 | 9/2010 | Matsudo | |
| 2012/0078189 A1* | 3/2012 | Ogawa | B29C 39/42 604/173 |
| 2012/0265145 A1 | 10/2012 | Mefti | |
| 2013/0006147 A1* | 1/2013 | Fukuda | A61B 5/150458 600/573 |
| 2013/0041330 A1 | 2/2013 | Matsudo | |
| 2014/0066842 A1 | 3/2014 | Zhang et al. | |
| 2015/0057605 A1* | 2/2015 | Ameri | A61M 37/0015 514/11.7 |
| 2019/0184366 A1* | 6/2019 | Henderson | B01J 19/0046 |

FOREIGN PATENT DOCUMENTS

| | | |
|---|---|---|
| EP | 1439871 B | 1/2009 |
| EP | 2338557 | 6/2011 |
| JP | 2003238347 | 8/2003 |
| JP | 2008079919 | 4/2008 |
| JP | 2010017214 | 1/2010 |
| JP | 20100502268 | 1/2010 |
| JP | 2017-164191 A | 9/2017 |
| WO | WO/93/16657 | 9/1993 |
| WO | WO/01/91846 | 12/2001 |
| WO | WO/03/092785 | 11/2003 |
| WO | WO/2008/072229 | 6/2008 |
| WO | WO 2010/071918 | 7/2010 |
| WO | WO/2011/044367 | 4/2011 |
| WO | WO/2011/115272 | 9/2011 |

OTHER PUBLICATIONS

Jacovella (2008) Use of calcium hydroxyl apatite (Radiesse) for facial augmentation. Clin Interv Aging 3(1): 161-74.

Kim et al., (2012) Microneedles for drug and vaccine delivery. Adv Drug Deliv Rev 64(14): 1547-68.

Suchaneka and Yoshimura (1998) Processing and properties of hydroxyapatite-based biomaterials for use as hard tissue replacement implants. J MaterRes 13(1): 94-117.

International Search Report together with Written Opinion issued for PCT/IL2019/050032 dated Jul. 11, 2019.

Shirkhanzadeh M. "Microneedles coated with porous calcium phosphate ceramics: effective vehicles for transdermal delivery of solid trehalose" Journal of Materials Science: Materials in Medicine. Jan. 2005;16(1):37-45.

Chopra et al. A comprehensive examination of topographic thickness of skin in the human face Aesthetic surgery journal. Nov. 2015;35(8):1007-13.

* cited by examiner

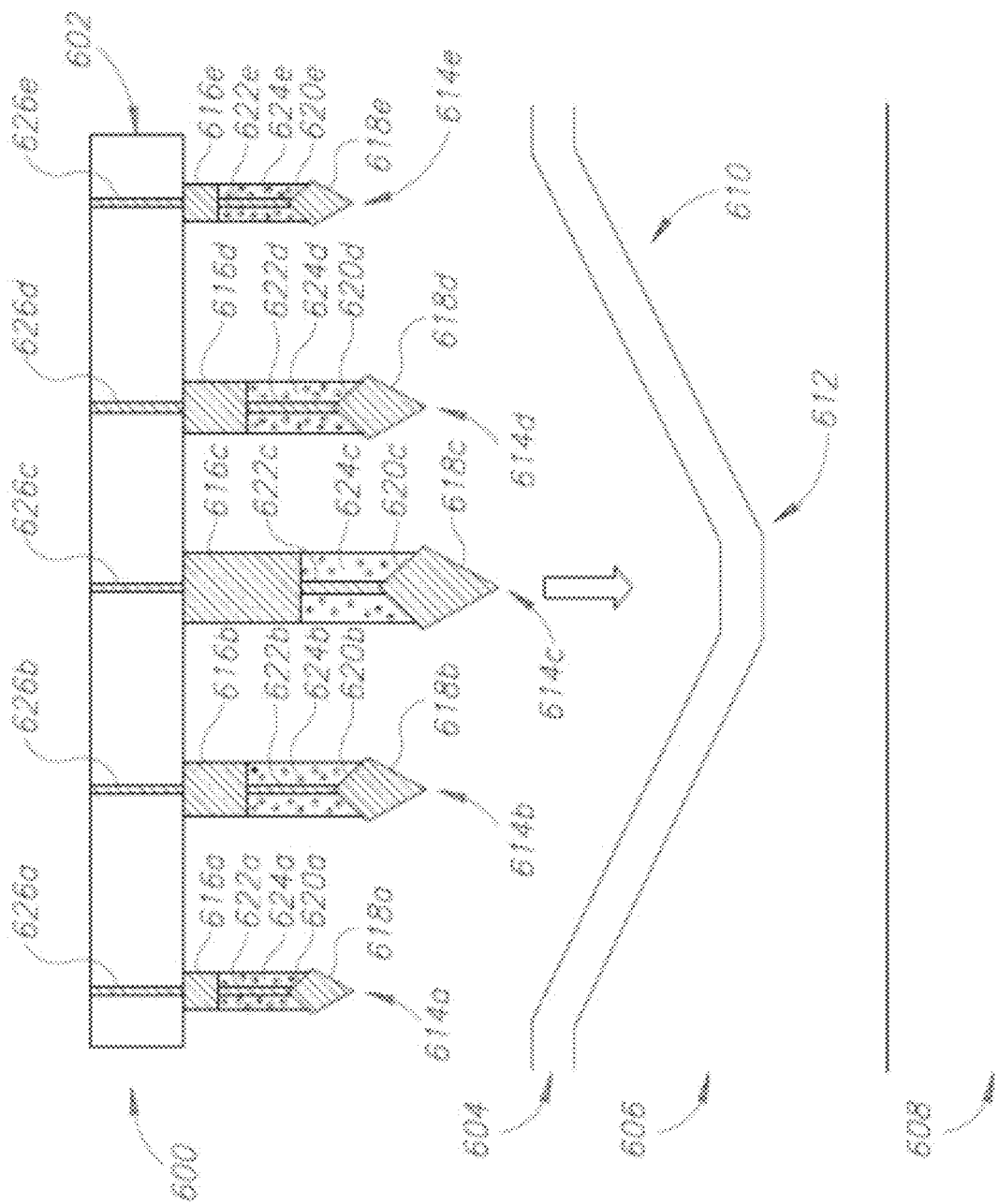

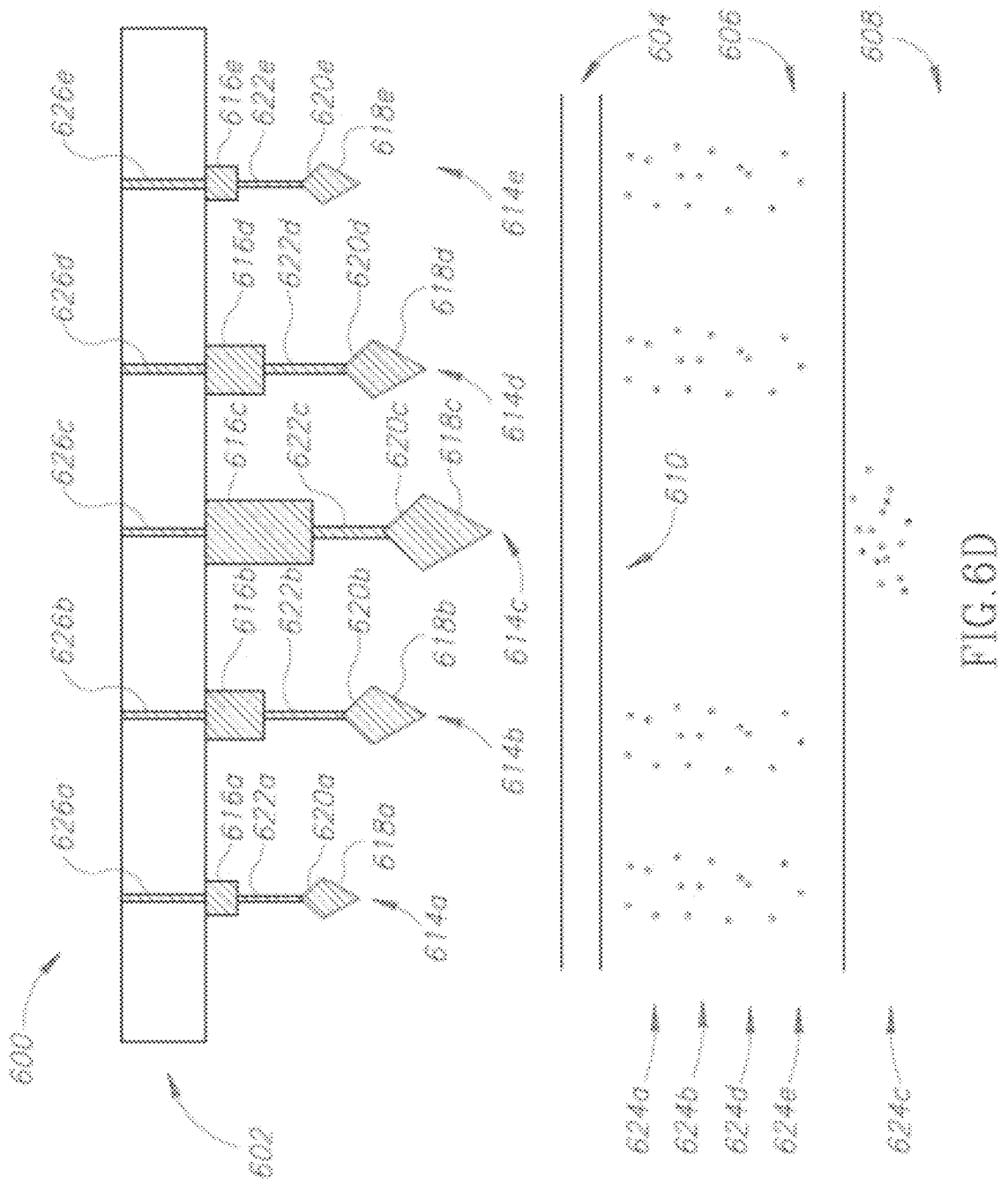

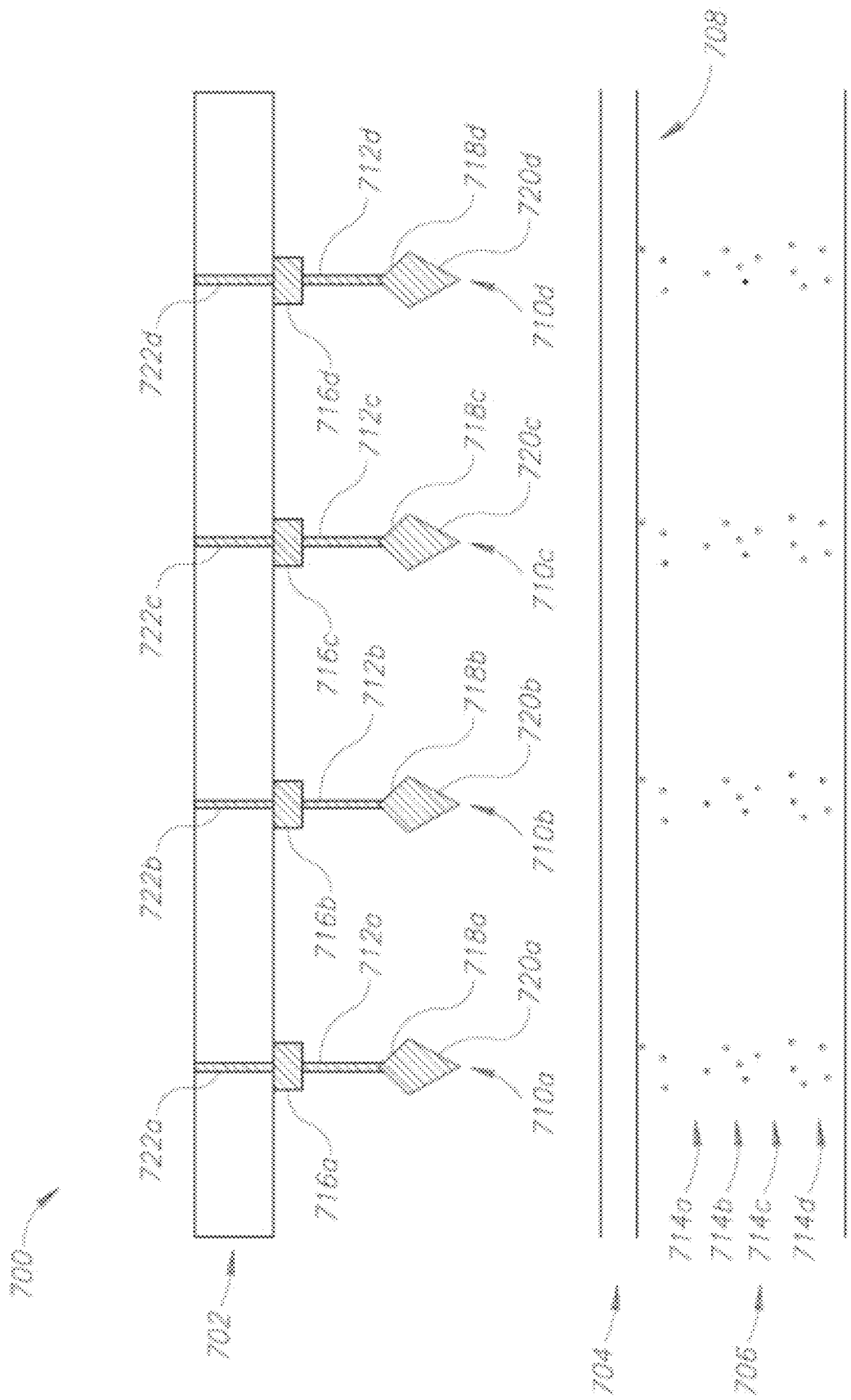

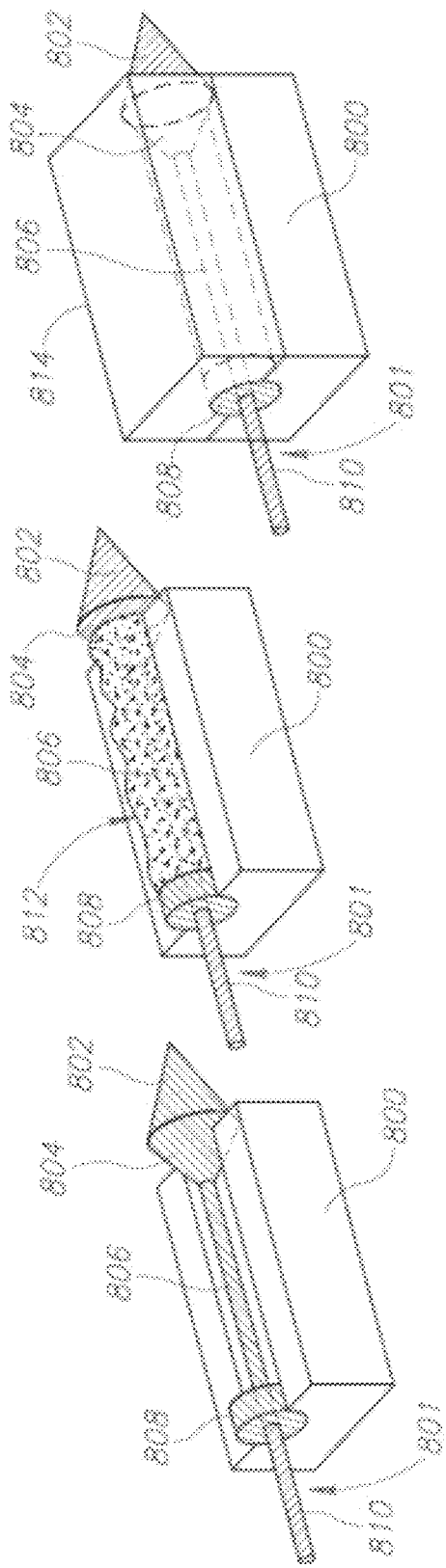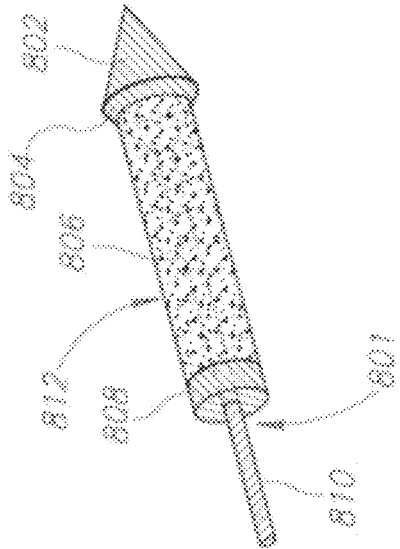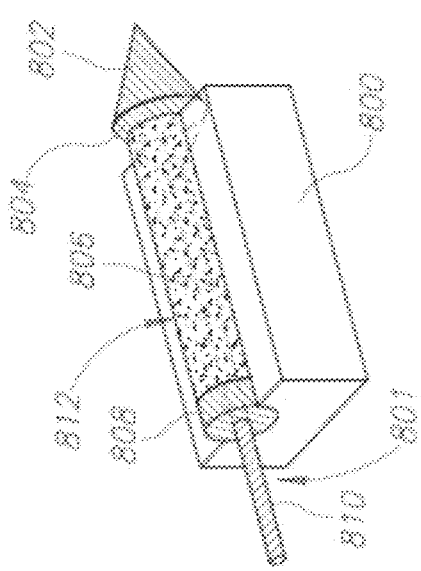

MICRONEEDLES AND COMPOSITIONS FOR SKIN AUGMENTATION

FIELD OF THE INVENTION

The present invention relates to microneedles and applicators comprising an array of microneedles for the administration of biocompatible materials effective in augmentation of skin, and methods of use thereof. In particular, the devices and methods of the present invention are aimed at filling the undesired lines, wrinkles, depressed scars and folds of a subject's skin and restoring youthful fullness to the skin.

BACKGROUND OF THE INVENTION

Skin is composed of the epidermis and the dermis. Below these layers lies the hypodermis, also commonly referred to as subcutaneous fat layer, sub-cutis or subcutaneous tissue, which is not usually classified as a layer of skin.

The outermost epidermis is made up of stratified squamous epithelium with an underlying basement membrane. It contains no blood vessels, and is nourished by diffusion from the dermis. The epidermis is mainly composed of keratinocytes, with melanocytes and Langerhans cells also present. This layer of skin functions as a barrier between the body and the external environment, keeping water in the body and preventing penetration of harmful chemicals and pathogens. The thickness of the epidermis in adult facial and neck skin is usually between 30 μm and 60 μm (micron, micrometer), depending on the specific location in the body. The thinnest epidermis is usually found in the posterior auricular, with a thickness of about 29.5 μm, while the thickest epidermis is usually found in the upper lip, with a thickness of about 62.6 μm (Chopra et al., Aesthetic Surgery Journal, 2015, Vol 35(8), pages 1007-1013).

The dermis lies below the epidermis and contains a number of structures including blood vessels, nerves, hair follicles, smooth muscle, glands and lymphatic tissue. The dermis (or corium) in facial and neck skin is typically 700-2000 micrometer (μm) thick, and is the major component of human skin. It is composed of a network of connective tissue, predominantly collagen fibrils providing support and elastin fibers providing flexibility. The main cell types composing the dermis are fibroblasts, adipocytes (fat storage) and macrophages.

The hypodermis lies below the dermis and is important for attaching the skin to the underlying bone and muscle as well as supplying it with blood vessels and nerves. The hypodermis is made up of loose connective tissue and elastin and contains fibroblasts, macrophages and adipocytes. The adipocytes play a major role in the fat storage function of the hypodermis. The fat serves as a filling material and as insulation of the body from the external environment.

Facial aging occurs as the result of several factors, among them are inherent changes within the skin, effects of gravity, activity of facial muscles leading to the formation of dynamic lines, skin loss or shift, bone loss, loss of tissue elasticity and exposure to harsh environmental conditions, particularly the sun or ultraviolet radiation and pollutants. The skin ages when the epidermis begins to thin, causing the junction with the dermis to flatten. Collagen decreases as a person ages and the bundles of collagen, which gives the skin turgor, become looser and lose strength. When the skin loses elasticity, it is less able to resist stretching. Coupled with gravity, muscle pull, and tissue changes, the skin begins to wrinkle. Water loss and breakdown of bonds between cells also reduces the barrier function of the skin, which can cause the skin's pore size to increase.

There have been efforts to develop and use compositions to correct defects in skin, such as scars and wrinkles, or to augment the tissue of a subject in order to improve the appearance of the skin, particularly facial skin. The average skin thickness in the face and neck (in areas were wrinkles, lines and folds are common) is 1.26 millimeter (mm).

Currently, there are dozens of known dermal filling agents for skin augmentation which include autologous implantable materials, allogeneic products, xenogeneic products and synthetically derived products. Available dermal fillers comprise biodegradable natural substances (such as collagen, gelatine, hyaluronic acid, dextran and dried acellular particulate dermal matrix), biodegradable synthetic polymers (such as poly-L-lactic acid, polyethylene oxide and carboxymethylcellulose), non-biodegradable synthetic polymers (such as polymethyl methacrylate, polyacrylamide, polyalkylimide and silicones) and combinations thereof.

Biocompatible ceramic skin augmentation materials, such as hydroxyapatite ($Ca_5(PO_4)_3(OH)$), are known to be efficient skin augmentation materials. Hydroxyapatite is a naturally occurring mineral form of calcium phosphate. Hydroxyapatite comprises the mineral constituent of bone, therefore rendering it biocompatible and non-immunogenic when introduced into the body of a subject. Of note, hydroxyapatite is biodegradable following the same metabolic pathways as bone debris resulting from common bone fractures, yet is semi-permanent, as it lasts up to 3 years when implanted into a subject. Moreover, when injected as small microspheres, hydroxyapatite acts as a scaffold that promotes new tissue formation similar to its surrounding environment. Inside skins such as the dermis, deposited particles of Hydroxyapatite support fibroblastic ingrowth and new collagen formation (Jacovella, P. F, *Clin. Interv. Aging.*, 2008, 3(1): 161-174, Suchanek W. and Yoshimura M., *J. Mater. Res.*, 1997, 13(1): 94-117).

Skin augmentation products are typically injected with a needle into the dermis layer or just below the surface of the skin, at the site of the wrinkle, line, or fold (or scar or subcutaneous tissue to be enhanced). The products essentially plump up the skin from beneath the upper layers of skin. Some skin augmentation products are implanted beneath the skin through an incision. In either case, the skin is cut or punctured with a needle or a scalpel type instrument to insert skin augmentation products into the desired location, and thus the procedure is performed by a trained medical professional. Application of dermal fillers by injection or implantation is uncomfortable and possibly painful to the subject, and, furthermore, requires highly trained medical professional manpower.

Currently used methods for wrinkle erasing are Botulinum toxin type A (known as "BOTOX"), peeling (mechanical or chemical), dermabrasion, surgery and the administration of fillers. All fillers are currently administered via a syringe connected to a needle. This technique however: cannot address fine wrinkles or lines, does not always give a smooth result, is painful, due to the high pressure which is built in the treated tissue during and after administration, is wasteful in augmentation material, and can be performed by only highly professional personal, i.e. plastic surgeons.

It is thus desirable to have means for efficient, easy-to-use, pain-free, finely-targeted delivery of skin fillers to achieve a smooth, youthful and natural look.

SUMMARY OF THE INVENTION

In certain embodiments, the present invention relates to novel combinations of microneedles and augmentation compositions, which provide highly efficient delivery of augmentation materials into the epidermis.

The inventive advantages of the new combinations are several. For example, as exemplified herein, the use of semi-solid and solid augmentation compositions provided by the present invention first provides the manufacturer of these microneedles the advantage of easy handling of the augmentation compositions when applying the composition onto the microneedles, and secondly provides the end-user, be that a trained plastic surgeon or a self-administering client, with the advantage of easy application of the microneedles onto the skin defect to be treated. More, as further exemplified herein, the augmentation compositions provided by the present invention deliver their full load of skin augmenting material only into the dermis and hypodermis target tissues, thus preventing waste of skin augmenting material, undesired side-effects associated with delivery into the epidermis, and the need for repeated or multiple administration cycles. Of note, the side-effects of delivery of skin augmenting materials into the epidermis are an appearance of small solid lumps in the treated skin, the skin does not look smooth, and ulceration of the lumps becomes a source of infection and inflammation.

Further inventive advantages of the new combinations are, for example, that they result in a homogeneous and smooth look in regular wrinkles and even in fine lines (e.g. wrinkles in lateral sides and above the eyebrow), and that they eliminate the need for powerful and painful injections. Moreover, they can be self-administered. They can also be used as a complementary treatment following botulinum injections in areas where it is not allowed to inject the Botulinum toxin (BTX).

The present invention, in certain embodiments, relates to microneedles, augmentation compositions, and to a device comprising an array of microneedles and a skin augmentation composition useful for augmenting skin in a subject. In particular, the device of the invention is useful for filling undesired lines, wrinkles, depressed scars and folds of a subject's skin. According to the invention, the microneedles advantageously comprise at least one biocompatible material that is injected into the dermis layer or hypodermis layer of a subject's facial or neck skin and remains there for a prolonged time-period, inducing a filling effect.

According to some embodiments, a microneedle is provided configured to administrate a biocompatible medical composition to a dermis layer and/or hypodermis layer of a subject, the microneedle comprising:
  a rigid rod section having at least one cavity which is open along its length, the cavity is configured to temporarily accommodate a biocompatible medical composition there-within;
  a rigid sharp tip section, at one end of the rod, configured to allow penetration of at least a part of the rod to a dermis layer and/or hypodermis layer of a subject;
  a rigid base section, at the second end of the rod, comprising a length of at least 30 μm;
wherein the sharp tip section and the base section are configured to devoid of the biocompatible medical composition.

According to some embodiments, the shape of the cross-section area of the rod section, the tip section and the base section is selected from: rectangular, triangular, circular, oval, polygonal, and any combination thereof.

According to some embodiments, the at least one cavity comprises the biocompatible medical composition, and wherein the biocompatible medical composition or at least part of the biocompatible medical composition is solid and/or semi-solid at room temperature and is configured to be released from the cavity/ies to the dermis and/or hypodermis upon contact with liquid in the dermis layer and/or hypodermis layer.

According to some embodiments, at least one of the following holds true:
  the biocompatible medical composition is configured to at least partially separate from the cavity and the microneedle, when in dermis and/or hypodermis environment;
  biocompatible medical composition comprises at least one of: skin augmentation material, botulinum composition, medical pigment composition, steroids and any combination thereof;
  the biocompatible medical composition comprises at least one of:
    at least one of: skin augmenting material, botulinum material, medical pigment material, steroids, and any combination thereof;
    at least one dispersant material, configured to disperse the at least one of: skin augmenting material, botulinum material, medical pigment material, steroids upon contact with the dermis layer and/or the hypodermis layer and any combination thereof; and
    at least one dispersant material, configured to promote diffusion and/or solubility and/or dispersion in water and/or water solution, and is selected from: water-soluble polymer, polyethylene glycol (PEG), polyethylene oxide (PEO), polyoxyethylene (POE), glycerin, carboxymethylcellulose, sterile water, magnesium sulfate, salt, and any combination thereof.

According to some embodiments, the base section is connected and/or anchored to a rigid connecting bar and/or a section of a substrate, such that the rod section is about perpendicular to the section of the substrate and/or to the rigid connecting bar.

According to some embodiments, an applicator is provided configured to administrate a biocompatible medical composition to a dermis layer and/or hypodermis layer of a subject, the applicator comprising:
  a substrate, configured to be attached to the subject's skin; and
  one or more microneedles, according to any one of the above mentioned embodiments, connected and/or anchored to the substrate, via their base section, such that the microneedles are about perpendicular to the substrate and such that the microneedles are configured to penetrate the dermis layer and/or hypodermis layer when the substrate is attached to the subject's skin.

According to some embodiments, at least one of the following holds true:
  at least a part of the substrate is at least partially transparent;
  at least a part of the substrate is not transparent;
  the substrate comprises markings, on a surface of the substrate, which is opposite to the surface of the attached microneedle/s, the markings configured to assist a care giver with the application of the microneedle/s;
  the substrate is: rigid, at least partially flexible, or flexible;
  the substrate comprises an adhesive material, configured to attach at least a part of the substrate to the subject's skin;
  the substrate comprises a form of at least one strip or at least one patch;

the microneedles are connected and/or anchored and arranged in a form selected from the group consisting of: at least one row, at least one array, at least two segments, and any combination thereof;

the microneedles comprise various lengths for at least one of: the rod sections, the base sections, the tip sections and any combination thereof.

According to some embodiments, the cavities of the microneedles comprise the biocompatible medical composition, and wherein the biocompatible medical composition is solid and/or semi-solid at room temperature and is configured to be released from the cavity/ties to the dermis and/or hypodermis upon contact with liquid in the dermis layer and/or hypodermis layer.

According to some embodiments, a method is provided for administrating of a biocompatible medical composition to a dermis and/or hypodermis of a subject; the method comprising:

providing one or more microneedles, according to any one of the above mentioned embodiments, with a biocompatible medical composition; wherein at least part of the biocompatible medical composition is solid and/or semi solid at room temperature and is configured to disperse when in contact with liquid environment of dermis layer and/or hypodermis layer; and wherein the step of providing is configured to devoid the tip section and the base section from the biocompatible medical composition;

inserting the microneedle/s to the dermis layer and/or hypodermis layer of a subject; and retracting the microneedle/s from the dermis layer and/or hypodermis layer of the subject, after a predetermined time period.

According to some embodiments, the method further comprising a step of injecting water solution or water for injection or saline, with or without an anesthetic material to the treated area, about 1 minute to about 30 minutes, prior to the insertion of the microneedle/s.

According to some embodiment, the step of inserting is provided via attaching the applicator, according to any one of the above mentioned embodiments, to the skin of the subject; and wherein the step of retracting comprises a retraction of the applicator. According to some embodiments, the method can be repeated as needed.

According to some embodiments, the method further comprises providing the biocompatible medical composition with:

at least one of: skin augmenting material, botulinum material, medical pigment material, steroids, and any combination thereof; and at least one dispersant material, configured to disperse the at least one of: skin augmenting material, botulinum material, steroids, and medical pigment material, upon contact with the dermis layer and/or the hypodermis layer.

According to some embodiments, the dispersant material is configured to promote dispersion, diffusion and/or solubility in water or water solution, and is selected from: water-soluble polymer, polyethylene glycol (PEG), polyethylene oxide (PEO), polyoxyethylene (POE), glycerin, carboxymethylcellulose, sterile water, magnesium sulfate, salt, and any combination thereof.

According to some embodiments, the predetermined time period is selected between about 0.5 to about 24 hours.

According to some embodiments, a method is provided configured for manufacturing the applicator, according to any one of the above mentioned embodiments, the method comprising:

cutting and/or carving at least one applicator from a sheet of a rigid material; and spreading the biocompatible medical composition onto the cavities of the microneedles rod sections, such that cavities are filled.

According to some embodiments, in a case of cutting or carving the at least one applicator out of the sheet, further comprising a step of returning the cut/curved applicator/s back to the sheet before spreading the composition, and removing the cut/curved applicator/s out again after the spreading step.

According to some embodiments, the method further comprising a step of removing any excessive composition from at least one of: the substrate, the tip section, the base section, and the outer surface of the rigid rod, while leaving the composition within the cavity/ies.

According to some embodiments, the method further comprising a step of providing the biocompatible medical composition with:

at least one of: skin augmenting material, botulinum material, medical pigment material, steroids, and any combination thereof; and at least one dispersant material in a frozen state, configured to disperse by melting while in the tissue, at least one of the: skin augmenting material, botulinum material, steroids, and medical pigment material, upon contact with the dermis layer and/or the hypodermis layer.

According to some embodiments, the method further comprising a step of connecting together at least two applicators with having a single microneedles' row, to provide an applicator with multiple microneedle rows.

According to some embodiments, the method further comprising a step of selecting the rigid material for manufacturing the applicators from a group consisting of: metal, plastic, polymeric, a ceramic material, a silicone, and an absorbable material configured to be absorbed in the dermis layer or hypodermis layer or in both dermis layer and hypodermis.

According to some embodiments of the invention a microneedle is provided, configured for administering a skin augmentation composition to a dermis layer or a hypodermis layer of human facial or neck skin, the microneedle comprising:

a biocompatible skin augmentation composition, comprising at least one biocompatible skin augmenting material; and at least one biocompatible dispersant, which is configured to disperse the skin augmenting material upon contact with the dermis layer or the hypodermis layer, wherein the skin augmentation composition is solid and/or semi-solid at room temperature, and is configured to disperse upon contact with liquid, in the dermis layer or the hypodermis layer, and a skeleton made of a rigid material, the skeleton comprises:

a base section on one end of the skeleton, having a length ($L_b$) of at least about 30 μm, wherein the base section substantially devoid of a skin augmentation composition;

a middle section connected to the base section on one end, having a length ($L_m$) of between about 35 μm to about 2500 μm, wherein the middle section comprises the skin augmentation composition, and is configured to at least partly expose the skin augmentation composition to the outer environment of the microneedle: and a sharp tip section connected to the middle section on one end and configured to penetrate human facial or neck skin on the other end, the tip having a base with a cross-section area which is same or larger than the cross-section of the middle section together with the skin augmentation composition, wherein the tip section substantially devoid of a skin augmentation composition.

According to some embodiments, the skin augmentation composition comprising at least about 25% by weight of at least one biocompatible skin augmenting material. According to some embodiments, the skin augmentation composition comprising at least about 1% by weight of at least one biocompatible dispersant. According to some embodiments, the skin augmentation composition comprises about 50% to about 75% by weight of the biocompatible skin augmenting material, and at least one biocompatible dispersant. According to some embodiments, at least about 10% of the total volume of the needle is filled with the skin augmentation composition. According to some embodiments, at least about 40% of the total volume of the needle is filled with the skin augmentation composition. According to some embodiments, about 40% to about 50% of the total volume of the needle is filled with the skin augmentation composition. According to some embodiments, biocompatible dispersant is configured to disperse at least a portion of the skin augmenting material into: the dermis layer, the hypodermis layer, or into both the dermis layer and the hypodermis layer.

According to some embodiments, the base section is between about 30 μm to about 60 μm in length ($L_b$), configured to enable the middle section to disperse at least a portion of the skin augmentation composition into the dermis layer. According to some embodiments, the base section is at least about 790 μm in length, configured to disperse the skin augmentation composition into the deep dermis layer or hypodermis layer. According to some embodiments, the base section is between about 790 μm to about 820 μm in length, and the biocompatible dispersant disperses the skin augmenting material into the deep dermis layer or hypodermis layer.

According to some embodiments, the microneedle is between about 500 μm to about 7000 μm in length (L). According to some embodiments, the microneedle is between about 1000 μm to about 2500 μm in length. According to some embodiments, the microneedle is between about 1000 μm to about 1500 μm in length.

According to some embodiments, rigid material is selected from a group consisting of: metal, plastic, polymeric, a ceramic material, a silicone, an absorbable material configured to be absorbed in the dermis layer or hypodermis layer or in both dermis layer and hypodermis. According to some embodiments, the metal is stainless steel. According to some embodiments, stainless steel is 304 stainless steel.

According to some embodiments, the base section has a shape selected from the group consisting of: a rectangular box, a cuboid, a cylinder, a triangular box and a polygonal box. According to some embodiments, the middle section has a shape selected from the group consisting of: a rectangular box, a cuboid, a cylinder, a triangular box and a polygonal box.

According to some embodiments, the middle section has a shape of one or more elongated boxes having elongated sidewalls and an elongated internal cavity, each elongated box comprises 1 to 3 open elongated sidewalls configured to at least partly expose the skin augmentation composition to the outer environment of the microneedle. According to some embodiments, each elongated box comprises two opposing elongated sidewalls and two opposing elongated open sidewalls. According to some embodiments, the length ($L_m$) of each one of the elongated boxes is selected between about 400 μm to about 800 μm and the width of each one of the elongated boxes is selected between about 200 μm to about 1000 μm. According to some embodiments, the skin augmentation composition is accommodated in the elongated internal cavity, between, near or attached to at least one elongated sidewall.

According to some embodiments, the middle section has a shape of one or more elongated cylinders having elongated sidewalls and an elongated internal cavity, each elongated cylinder comprises an arcuate opening configured to at least partly expose the skin augmentation composition to the outer surface of the microneedle. According to some embodiments, each arcuate opening spans up to half of the circumference of the elongated sidewalls. According to some embodiments, the length ($L_m$) of each one of the elongated cylinders is selected between about 400 μm to about 2500 μm and the width of each one of the elongated cylinders is selected between about 200 μm to about 500 μm. According to some embodiments, the skin augmentation composition is located in the elongated internal cavity, between, near and/or attached to at least one elongated sidewall.

According to some embodiments, the middle section has a shape of one or more containers comprising the skin augmentation composition in at least one internal cavity, each container having perforated sidewalls configured to at least partly expose the skin augmentation composition to the outer surface of the microneedle.

According to some embodiments, the cross-section of the base of the sharp tip section is about 10% to 45% larger than the total cross-section of the middle section and the skin augmentation composition.

According to some embodiments, the sharp tip section has a tip having a 10° to a 60° angle. According to some embodiments, the sharp tip section has a shape selected from the group consisting of: a cone, a pyramid, a triangular pyramid and a polygonal pyramid.

According to some embodiments, the biocompatible skin augmenting material is hydroxyapatite and/or hyaluronic acid. According to some embodiments, the biocompatible skin augmenting material is in the form of solid and/or semi solid particles and/or spheres. According to some embodiments, about 10% of the particles or spheres are about 15 μm to about 35 μm in diameter. According to some embodiments, bout 50% of the particles and/or spheres are about 35 μm to about 50 μm in diameter. According to some embodiments, about 90% of the particles and/or spheres are about 50 μm to about 70 μm in diameter.

According to some embodiments, the biocompatible dispersant is a water-soluble polymer and/or salt. According to some embodiments, the biocompatible dispersant is glycerin. According to some embodiments, the biocompatible dispersant comprises glycerin; and wherein the augmenting material comprises calcium hydroxylapatite (CaHA) microspheres, together with sterile water and carboxymethylcellulose. According to some embodiments, the water-soluble polymer is selected from: polyethylene glycol (PEG), polyethylene oxide (PEO), polyoxyethylene (POE), and any combination thereof. According to some embodiments, the water-soluble polymer has a molecular weight in the range of about 1000 to about 19000 gram/mole. According to some embodiments, the water-soluble polymer is PEG 12000.

According to some embodiments, the skin augmentation composition further comprises: at least one of: Botulinum toxin type A or type B, medical pigment, and any combination thereof.

According to some embodiments, the middle section of the microneedles comprise dispersant without augmenting material but with at least one of: Botulinum toxin type A or type B, medical pigment, steroids, and any combination thereof According to some embodiments of the invention, an applicator is provided, configured for administration of a skin augmentation composition to the dermis layer or hypodermis layer of facial or neck skin, comprising plurality of microneedles, according to at least some of the embodiments as mentioned above.

According to some embodiments, the applicator further comprising: a substrate having a generally flattened structure having two opposing surfaces, wherein one surface is intended for being placed proximal to the skin of a subject and the other surface facing away from the skin of the subject; and at least one row or an array of microneedles located on the surface intended for being placed proximal to the skin of the subject, the array comprising a multiplicity of microneedles, according to at least some of the embodiments as mentioned above.

According to some embodiments, the distance between microneedles is selected between about 0.5 mm and about 2.5 mm. According to some embodiments, the applicator is in a form of a strip or a patch.

According to some embodiments of the invention, a method is provided, for filling an undesired section selected from: fold, wrinkle, line and depressed area, located in the dermis layer or hypodermis layer of facial or neck skin of a subject, the method comprising attaching to the site of the fold, wrinkle, line or depressed area, at least one microneedle, according to at least some of the embodiments as mentioned above, or at least one applicator, according to at least some of the embodiments as mentioned above.

According to some embodiments, the method further comprising injecting anesthetic material with water solution or water for injection to the treated area, about 1 minute to about 30 minutes, prior to the attachment of the microneedle/s. According to some embodiments, the microneedle or the applicator is kept attached to the site of the fold, wrinkle, line or depressed area between about 0.5 to about 24 hours.

According to some embodiments of the invention, a microneedle is provided, according to at least some of the embodiments as mentioned above, or an applicator is provided, according to at least some of the embodiments as mentioned above, for use in filling an undesired fold, wrinkle, line or depressed area in the dermis layer or hypodermis layer of facial or neck skin.

According to some embodiments of the invention, a skin augmentation composition is provided, comprising: at least about 25% by weight of at least one biocompatible skin augmenting material, and at least one biocompatible dispersant, which is configured to disperse the skin augmenting material upon contact with the dermis layer or hypodermis layer.

According to some embodiments of the invention, a microneedle is provided, configured for administration of a biocompatible medical composition to a dermis layer and/or hypodermis layer of a subject, the microneedle comprising:

a rigid rod having at least one open cavity, the cavity is configured to temporarily accommodate a biocompatible medical composition there-within;

a rigid sharp tip, at one end of the rod, configured to allow penetration of at least a part of the rod to a dermis layer and/or hypodermis layer of a subject.

According to some embodiments, the shape of the cross-section area of the rod is selected from: rectangular, triangular, circular, oval, polygonal, and any combination thereof.

According to some embodiments, the cavity comprises the biocompatible medical composition, and wherein the biocompatible medical composition is solid and/or semi-solid at room temperature and is configured to disperse upon contact with liquid in the dermis layer and/or hypodermis layer. According to some embodiments, the biocompatible medical composition is configured to at least partially separate from the cavity and the microneedle, when in dermis and/or hypodermis environment.

According to some embodiments, the biocompatible medical composition comprises at least one of: skin augmentation composition, botulinum composition, medical pigment composition, steroids and any combination thereof. According to some embodiments, the biocompatible medical composition comprises: at least one of: skin augmenting material, botulinum material, medical pigment material, steroids, and any combination thereof; and at least one dispersant material, configured to disperse the at least one of: skin augmenting material, botulinum material, steroids and medical pigment material, upon contact with the dermis layer and/or the hypodermis layer.

According to some embodiments, the dispersant material is configured to promote diffusion and/or solubility in water and/or water solution, and is selected from: water-soluble polymer, polyethylene glycol (PEG), polyethylene oxide (PEO), polyoxyethylene (POE), glycerin, carboxymethylcellulose, sterile water, magnesium sulfate, salt, and any combination thereof.

According to some embodiments, the microneedle further comprises a rigid base section comprising a length ($L_b$) of at least 30 μm, at the second end of the rod. According to some embodiments, the sharp tip section and/or the base section substantially devoid of the biocompatible medical composition.

According to some embodiments, the base section is configured to be connected and/or anchored to a rigid connecting bar. According to some embodiments, the base section is connected and/or anchored to a rigid connecting bar, such that the rod is about perpendicular to the rigid connecting bar.

According to some embodiments, the base section is configured to be connected and/or anchored to a substrate. According to some embodiments, the base section is connected and/or anchored to a section of a substrate, such that the rod is about perpendicular to the section of the substrate.

According to some embodiments of the invention, a device is provided, configured for administration of a biocompatible medical composition to a dermis layer and/or hypodermis layer of a subject, the device comprising:

- a substrate, configured to be attached to the subject's skin; and
- at least one microneedle, according to at least some embodiments as mentioned above, connected and/or anchored to the substrate, such that when the substrate is attached to the subject's skin, the at least one microneedle penetrates the dermis layer and/or hypodermis layer.

According to some embodiments, at least a part of the substrate is at least partially transparent. According to some embodiments, the substrate is not transparent. According to some embodiments, the substrate further comprises markings, on a surface of the substrate, which is opposite to the surface of the attached microneedle/s, the markings are configured to assist a care giver with the location and application of the microneedle/s.

According to some embodiments, the device comprising a plurality of the microneedles, arranged in a form selected from the group consisting of: at least one row, at least one array, at least two segments, and any combination thereof. According to some embodiments, the plurality of the microneedles comprises various lengths (L) for the microneedles.

According to some embodiments, the substrate is: rigid, at least partially flexible, or flexible. According to some embodiments, the substrate comprises an adhesive material, configured to attach at least a part of the substrate to the subject's skin According to some embodiments, the substrate comprises a form of a strip or a patch.

According to some embodiments, a method is provided, for administrating of a biocompatible medical composition to a dermis and/or hypodermis of a subject; the method comprising:
  providing at least one microneedle, according to at least some of the embodiments as mentioned above, with a biocompatible medical composition; wherein the biocompatible medical composition or at least part of the composition is solid and/or semi solid at room temperature and is configured to be released from the cavities and disperse when in liquid environment of dermis layer and/or hypodermis layer;
  inserting the at least one microneedle to the dermis layer and/or hypodermis layer of a subject; and optionally,
  retracting the at least one microneedle from the dermis layer and/or hypodermis layer of the subject, after a predetermined time period.

According to some embodiments, the step of retracting the substrate is provided after at least one microneedle, at least partly released the medical composition in the skin or sub cutis. According to some embodiments, the step of providing further comprises substantially devoid the tip section and/or the base section from the biocompatible medical composition.

According to some embodiments, the method further comprising injecting an anesthetic material with water solution or water for injection to the treated area, about 1 minute to about 30 minutes, prior to the insertion of the microneedle/s.

According to some embodiments, the step of inserting is provided via attaching a device, according to at least some of the embodiments as mentioned above, to the skin of the subject; and wherein the step of retracting comprises a retraction of the device.

According to some embodiments, the method further comprises providing the biocompatible medical composition with:
  at least one of: skin augmenting material, botulinum material, medical pigment material, steroids, and any combination thereof; and
  at least one dispersant material, configured to disperse the at least one of: skin augmenting material, botulinum material, steroids, and medical pigment material, upon contact with the dermis layer and/or the hypodermis layer.

According to some embodiments, the dispersant material is configured to promote diffusion and/or solubility in water or water solution, and is selected from: water-soluble polymer, polyethylene glycol (PEG), polyethylene oxide (PEO), polyoxyethylene (POE), glycerin, carboxymethylcellulose, sterile water, magnesium sulfate, salt, and any combination thereof.

According to some embodiments, the predetermined time period is selected between about 0.5 to about 24 hours.

The present invention provides, in one aspect, a microneedle for administering a skin augmentation composition to the dermis layer or hypodermis layer of human facial or neck skin, the microneedle comprising: (a) a skin augmentation composition comprising at least about 25% by weight of at least one biocompatible skin augmenting material, and at least one biocompatible dispersant which disperses the skin augmenting material upon contact with the dermis layer or hypodermis layer; and (b) a skeleton made of a rigid material, the skeleton comprises: (i) a base section on one end of the skeleton, having a height of at least about 30 μm, the base section substantially devoid of a skin augmenting material, (ii) a middle section connected to the base section on one end, having a height of between about 35 μm to about 2500 μm, comprising the skin augmentation composition, wherein the middle section and the skin augmentation composition are configured to at least partly expose the skin augmentation composition to the outer surface of the microneedle, and (iii) a sharp tip section connected to the middle section on one end and configured to penetrate human facial or neck skin, having a diameter the same or larger than the diameter of the middle section, the tip section substantially devoid of a skin augmenting material; wherein the skin augmentation composition is solid or semi-solid at room temperature.

In certain embodiments, the skin augmentation composition is solid at room temperature. In certain embodiments, the skin augmentation composition is solid at 3° C. In certain embodiments, the skin augmentation composition is solid at 20° C. In certain embodiments, the skin augmentation composition is solid at room temperature. In certain embodiments, the skin augmentation composition is solid at 30° C. In certain embodiments, the skin augmentation composition is solid at 40° C.

In certain embodiments, the skin augmentation composition is solid at room temperature, the skin augmenting material is solid at room temperature and the dispersant is solid at room temperature. In certain embodiments, the skin augmentation composition is solid at room temperature, the skin augmenting material is semi-solid at room temperature and the dispersant is solid at room temperature. In certain embodiments, the skin augmentation composition is solid at room temperature, the skin augmenting material is solid at room temperature and the dispersant is semi-solid at room temperature. In certain embodiments, the skin augmentation composition is solid at room temperature, the skin augmenting material is semi-solid at room temperature and the dispersant is semi-solid at room temperature. In certain embodiments, the skin augmentation composition is semi-solid at room temperature, the skin augmenting material is solid at room temperature and the dispersant is solid at room temperature. In certain embodiments, the skin augmentation composition is semi-solid at room temperature, the skin augmenting material is semi-solid at room temperature and the dispersant is solid at room temperature. In certain embodiments, the skin augmentation composition is semi-solid at room temperature, the skin augmenting material is solid at room temperature and the dispersant is semi-solid at room temperature. In certain embodiments, the skin augmentation composition is semi-solid at room temperature, the skin augmenting material is semi-solid at room temperature and the dispersant is semi-solid at room temperature.

In certain embodiments, the skin augmentation composition substantially consists of the biocompatible skin augmenting material and the biocompatible dispersant. In certain embodiments, the skin augmentation composition consists of the biocompatible skin augmenting material and the biocompatible dispersant.

In certain embodiments, the skin augmentation composition is solid at room temperature, comprises about 50% to about 75% by weight of the biocompatible skin augmenting material, and about 25% to about 50% by weight of the biocompatible dispersant, wherein at least about 20% of the total volume of the needle is filled with the skin augmentation composition. In certain embodiments, the skin augmentation composition is solid at room temperature, comprises about 60% to about 65% by weight of the biocompatible skin augmenting material, and about 35% to about 40% by weight of the biocompatible dispersant, wherein about 40% to about 50% of the total volume of the needle is filled with the skin augmentation composition.

In certain embodiments, the skin augmentation composition comprises at least about 30% by weight of the biocompatible skin augmenting material. In certain embodiments, the skin augmentation composition comprises at least about 35% by weight of the biocompatible skin augmenting material. In certain embodiments, the skin augmentation composition comprises at least about 40% by weight of the biocompatible skin augmenting material. In certain embodiments, the skin augmentation composition comprises at least about 45% by weight of the biocompatible skin augmenting material. In certain embodiments, the skin augmentation composition comprises at least about 50% by weight of the biocompatible skin augmenting material. In certain embodiments, the skin augmentation composition comprises at least about 55% by weight of the biocompatible skin augmenting material. In certain embodiments, the skin augmentation composition comprises at least about 60% by weight of the biocompatible skin augmenting material.

In certain embodiments, the skin augmentation composition comprises at least about 1% by weight of the at least one biocompatible dispersant. In certain embodiments, the skin augmentation composition comprises at least about 25% by weight of the at least one biocompatible dispersant. In certain embodiments, the skin augmentation composition comprises at least about 30% by weight of the at least one biocompatible dispersant. In certain embodiments, the skin augmentation composition comprises at least about 30% by weight of the at least one biocompatible dispersant. In certain embodiments, the skin augmentation composition comprises at least about 35% by weight of the at least one biocompatible dispersant. In certain embodiments, the skin augmentation composition comprises at least about 30%, at least about 35%, at least about 40%, at least about 45%, at least about 50%, at least about 55% or at least about 60% by weight of the biocompatible skin augmenting material; and at least about 1%, at least about 25%, at least about 30% or at least about 35% by weight of the at least one biocompatible dispersant. Each possibility represents a separate embodiment of the invention.

In certain embodiments, the skin augmentation composition comprises 4% by weight of the biocompatible skin augmenting material for every 3% by weight of the at least one biocompatible dispersant. In certain embodiments, the skin augmentation composition comprises 5% by weight of the biocompatible skin augmenting material for every 3% by weight of the at least one biocompatible dispersant. In certain embodiments, the skin augmentation composition comprises 6% by weight of the biocompatible skin augmenting material for every 3% by weight of the at least one biocompatible dispersant.

In certain embodiments, the skin augmentation composition comprises about 50% to about 75% by weight of the biocompatible skin augmenting material, and about 25% to about 50% by weight of the biocompatible dispersant. In certain embodiments, the skin augmentation composition comprises about 60% to about 65% by weight of the biocompatible skin augmenting material, and about 35% to about 40% by weight of the biocompatible dispersant. In certain embodiments, the skin augmentation composition comprises about 62.5% by weight of the biocompatible skin augmenting material, and about 37.5% by weight of the biocompatible dispersant.

In certain embodiments, at least about 20% of the total volume of the needle is filled with the skin augmentation composition. In certain embodiments, at least about 30% of the total volume of the needle is filled with the skin augmentation composition. In certain embodiments, at least about 40% of the total volume of the needle is filled with the skin augmentation composition. In certain embodiments, at least about 50% of the total volume of the needle is filled with the skin augmentation composition. In certain embodiments, about 40% to about 50% of the total volume of the needle is filled with the skin augmentation composition.

In certain embodiments, the biocompatible dispersant disperses at least a portion of the skin augmenting material into the dermis layer, into the hypodermis layer, or into both the dermis layer and the hypodermis layer. In certain embodiments, the biocompatible dispersant disperses at least a portion of the skin augmenting material into both the dermis layer and the hypodermis layer.

In certain embodiments, the base section is between about 30 μm to about 60 μm in height, and the biocompatible dispersant disperses at least a portion of the skin augmenting material into the dermis layer. In certain embodiments, the biocompatible dispersant further disperses at least a portion of the skin augmenting material into the hypodermis layer. In certain embodiments, the base section is at least about 30 μm in height, and the biocompatible dispersant disperses at least a portion of the skin augmenting material into the dermis layer. In certain embodiments, the biocompatible dispersant further disperses at least a portion of the skin augmenting material into the hypodermis layer.

In certain embodiments, the base section is at least about 60 μm in height, and the biocompatible dispersant disperses at least a portion of the skin augmenting material into the dermis layer. In certain embodiments, the biocompatible dispersant further disperses at least a portion of the skin augmenting material into the hypodermis layer. In certain embodiments, the base section is between about 790 μm to about 820 μm in height, and the biocompatible dispersant disperses the skin augmenting material into the hypodermis layer or deep dermis layer. In certain embodiments, the base section is at least about 790 μm in height, and the biocompatible dispersant disperses the skin augmenting material into the deep dermis layer or hypodermis layer or both. In certain embodiments, the base section is at least about 820 μm in height, and the biocompatible dispersant disperses the skin augmenting material into the deep dermis or hypodermis layer or both. In certain embodiments, the base section is at least about 2000 μm in height, and the biocompatible dispersant disperses the skin augmenting material into the hypodermis layer. In certain embodiments, the base section is at least about 30 μm in height, and the biocompatible dispersant disperses the skin augmenting material into the hypodermis layer.

In certain embodiments, the microneedle is between about 500, 1000, 1500, 2000, 2500 or 3000 μm to about 2500, 3000, 4000, 5000, 6000 or 7000 μm in height. In certain embodiments, the microneedle is between about 1000 μm to about 2500 μm in height. In certain embodiments, the microneedle is between about 1000 μm to about 1500 μm in height. Each possibility represents a separate embodiment of the invention.

In certain embodiments, the rigid material is selected from a group consisting of metal, a plastic, polymeric, a ceramic material, a silicone material and a combination thereof. In certain embodiments, the metal is stainless steel. Each possibility represents a separate embodiment of the invention. In certain embodiments, the stainless steel is 304 stainless steel. In certain embodiments, the rigid material is made of a biocompatible absorbable material.

In certain embodiments, the base section has a shape selected from the group consisting of a rectangular box, a cuboid, a cylinder, a triangular box and a polygonal box. Each possibility represents a separate embodiment of the invention. In certain embodiments, the base section has a shape of a rectangular box or of a cylinder.

In certain embodiments, the middle section has a shape selected from the group consisting of a rectangular box, a cuboid, a cylinder, a triangular box and a polygonal box. Each possibility represents a separate embodiment of the invention.

In certain embodiments, the middle section has a shape of one or more elongated boxes having elongated sidewalls and an elongated internal cavity, each elongated box comprises 1 to 3 open elongated sidewalls configured to at least partly expose the skin augmentation composition to the outer surface of the microneedle. In certain embodiments, each elongated box comprises two opposing elongated sidewalls and two opposing elongated open sidewalls. In certain embodiments, the height of each one of the elongated boxes is about 100, 200, 300 or 400 μm to about 600, 700, 800, 900, 1000, 1100, 1200, or 1300 μm and the width of each one of the elongated boxes is about 300, 400, 500, 600, 700, or 800 μm. Each possibility represents a separate embodiment of the invention. In certain embodiments, the skin augmentation composition is located in the elongated internal cavity, between, near or attached to at least one elongated sidewall. Each possibility represents a separate embodiment of the invention.

In certain embodiments, the middle section has a shape of one or more elongated cylinders having elongated sidewalls and an elongated internal cavity, each elongated cylinder comprises an arcuate opening configured to at least partly expose the skin augmentation composition to the outer surface of the microneedle. In certain embodiments, each arcuate opening spans up to half of the circumference of the elongated sidewalls. In certain embodiments, the height of each one of the elongated cylinders is about 400 μm to about 600, 700, 800, 900, 1000, 1100, 1200 or 1300 μm and the width of each one of the elongated cylinders is about 400, 500, 600, 700, 800, 1000, or 1300 μm. Each possibility represents a separate embodiment of the invention. In certain embodiments, the skin augmentation composition is located in the elongated internal cavity, between, near or attached to at least one elongated sidewall. Each possibility represents a separate embodiment of the invention.

In certain embodiments, the middle section has a shape of one or more containers comprising the skin augmentation composition, optionally in at least one internal cavity, each container having perforated sidewalls configured to at least partly expose the skin augmentation composition to the outer surface of the microneedle.

In certain embodiments, the middle section has a shape of one or more containers comprising the skin augmentation composition, optionally in an elongated internal cavity, each container having perforated sidewalls configured to at least partly expose the skin augmentation composition to the outer surface of the microneedle.

In certain embodiments, the sharp tip section has the same diameter as the total diameter of the middle section and the skin augmentation composition. In certain embodiments, the sharp tip section has a larger diameter than the total diameter of the middle section and the skin augmentation composition. In certain embodiments, the sharp tip section is about 5%, about 10%, about 15% or about 20% larger than the total diameter of the middle section and the skin augmentation composition. In certain embodiments, the sharp tip section has a tip having a 10° angle, a 20° angle, a 30° angle, a 40° angle, a 50° angle or a 60° angle. Each possibility represents a separate embodiment of the invention. In certain embodiments, the sharp tip section has a shape selected from the group consisting of: a cone, a pyramid, a triangular pyramid and a polygonal pyramid. Each possibility represents a separate embodiment of the invention.

In certain embodiments, the biocompatible skin augmenting material is calcium-hydroxyapatite or calcium-hydroxylapatite. In certain embodiments, the biocompatible skin augmenting material is hyaluronic acid. In certain embodiments, the biocompatible skin augmenting material is in the form of solid particles or solid spheres. In certain embodiments, about 10% of the particles or spheres are up to about 15 μm to about 35 μm in diameter. In certain embodiments, about 50% of the particles or spheres are up to about 35 μm to about 50 μm in diameter. In certain embodiments, about 90% of the particles or spheres are up to about 50 μm to about 70 μm in diameter. In certain embodiments, about 10% of the particles or spheres are up to about 26 μm in diameter. In certain embodiments, about 50% of the particles or spheres are up to about 41 μm in diameter. In certain embodiments, about 90% of the particles or spheres are up to 64 μm in diameter.

In certain embodiments, the biocompatible dispersant is a water-soluble polymer. In certain embodiments, the water-soluble polymer is polyethylene glycol (PEG), polyethylene oxide (PEO) or polyoxyethylene (POE). In certain embodiments, the water-soluble polymer has a molecular weight in the range of about 1000, about 2000, about 3000, about 4000, about 5000, about 6000, about 7000, about 8000, about 9000 or about 10000 to about 10000, about 11000, about 12000, about 13000, about 14000, about 15000, about 16000, about 17000, about 18000 or 19000 gram/mole. Each possibility represents a separate embodiment of the invention. In certain embodiments, the water-soluble polymer is PEG 12000.

The present invention further provides, in another aspect, an applicator configured for administration of a skin augmentation composition to the dermis layer or hypodermis layer of facial or neck skin, comprising a microneedle as described above.

In certain embodiments, the applicator comprises: (a) a substrate having a generally flattened structure having two opposing surfaces, wherein one surface is intended for being placed proximal to the skin of a subject and the other surface facing away from the skin of the subject; and (b) at least one array of microneedles located on the surface intended for being placed proximal to the skin of the subject, the array comprising a multiplicity of microneedles as described above.

In certain embodiments, the applicator comprises: (a) a substrate having a un-flattened structure having two opposing surfaces, wherein one surface is intended for being placed proximal to the skin of a subject and the other surface facing away from the skin of the subject; and (b) at least one array of microneedles located on the surface intended for being placed proximal to the skin of the subject, the array comprising a multiplicity of microneedles as described above.

In certain embodiments, the distance between microneedles is selected in the range of about 0.5-2.5 mm; for example, about: 0.5, 0.6, 0.7, 0.8, 1.0, 1.2, 1.5, 2.0, 2.2, or 2.5 mm. Each possibility represents a separate embodiment of the invention.

In certain embodiments, the applicator is in a form of a strip or a patch. In certain embodiments, the applicator is in the form of a strip. In certain embodiments, the applicator is in the form of a patch.

The present invention further provides, in another aspect, a method for filling an undesired fold, wrinkle, line or depressed area in the dermis layer or hypodermis layer of facial or neck skin of a subject, comprising attaching to the site of the fold, wrinkle, line or depressed area a microneedle as described above or an applicator as described above.

In certain embodiments, the microneedle or applicator are kept attached to the site of the fold, wrinkle, line or depressed area for about 3 to about 6 hours. In certain embodiments, the microneedle or applicator are kept attached to the site of the fold, wrinkle, line or depressed area for about 3 to about 12 hours. In certain embodiments, the microneedle or applicator are kept attached to the site of the fold, wrinkle, line or depressed area for about 3 to about 18 hours. In certain embodiments, the microneedle or applicator are kept attached to the site of the fold, wrinkle, line or depressed area for about 3 to about 24 hours. In certain embodiments, the microneedle or applicator are kept attached to the site of the fold, wrinkle, line or depressed area for about 0.5 to about 24 hours.

The present invention further provides, in another aspect, a microneedle as described above, or an applicator as described above, for use in filling an undesired fold, wrinkle, line or depressed area in the dermis layer or hypodermis layer of facial or neck skin.

The present invention further provides, in another aspect, a skin augmentation composition comprising at least about 25% by weight of at least one biocompatible skin augmenting material, and at least about 1% by weight of at least one biocompatible dispersant which disperses the skin augmenting material upon contact with a dermis layer or hypodermis layer of a human facial or neck skin.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 6A, 6B, 6C and 6D schematically show application of an applicator to a deep skin line or deficiency, according to some embodiments of the invention:

FIGS. 7A, 7B, 7C and 7D schematically show application of an applicator to a shallow skin line or deficiency, according to some embodiments of the invention;

FIGS. 8A, 8B, 8C, 8D and 8E schematically show a manufacturing procedure for microneedles, according to some embodiments of the invention:

Figure 1A:
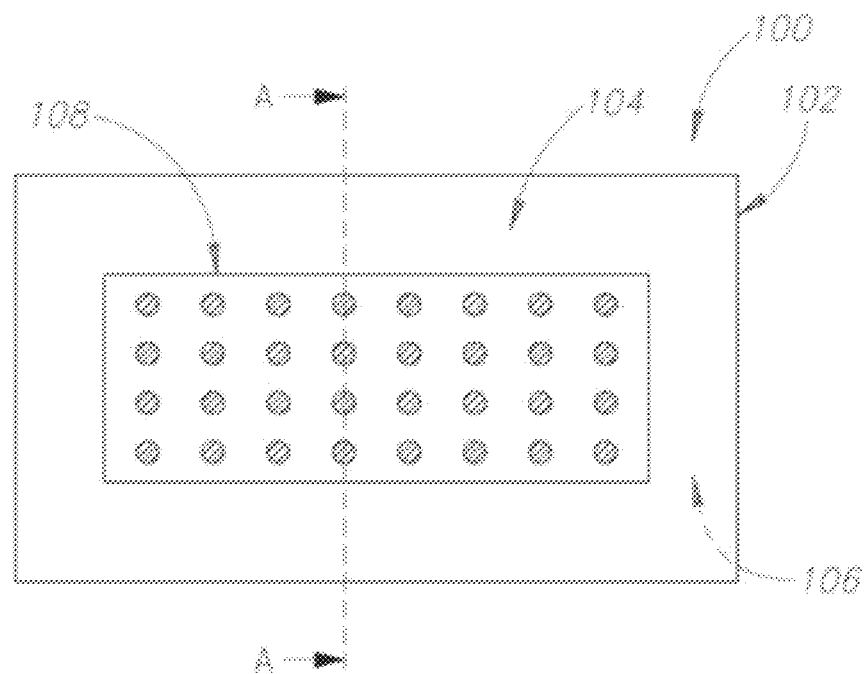
FIG. 1A schematically shows an applicator, according to some embodiments of the invention, in the form of a patch.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The present invention provides, for the first time, a microneedle-based applicator for delivery of a skin augmentation composition to the skin of a subject, configured to be delivered according to the histological depth and the shape of the deficient area. The applicators of the invention provide an efficient, comfortable and easy-to-use delivery system for skin augmentation compositions. The present invention further provides delivery methods of skin augmentation compositions to the skin of a subject. The methods of the invention enable, inter alia, filling of undesired folds, wrinkles, or lines in a subject's skin. According to some embodiments, the methods of the invention enable a subject to use the applicators and methods of the invention without the help of a trained medical professional. According to other embodiments, the applicators of the invention may be supplied as disposable strips or patches. Each possibility represents a separate embodiment of the present invention.

According to one aspect, the present invention provides an applicator configured for administration of a skin augmentation composition to a skin of a subject, the applicator comprising a substrate, wherein the substrate has a generally flattened structure having two opposing surfaces, wherein one surface is intended for being placed proximal to the skin of a subject and the other surface facing away from the skin of the subject; and an array of microneedles, wherein the array of microneedles is located on the surface proximal to the skin of the subject, the array comprising a multiplicity of microneedles, wherein each of the microneedles comprises:
  a skeleton made of a rigid material, the skeleton comprises:
    a sharp tip section located on one end of the skeleton, the sharp tip section being configured to penetrate a skin of a subject;
    a base on an opposing end of the skeleton; and
    a middle section connecting between the sharp tip section and the base; and
  a skin augmentation composition, wherein the augmentation composition at least partly surrounds the middle section, such that a diameter of the sharp tip section is larger than a diameter of the augmentation composition.

According to another aspect, the present invention provides a microneedle for administration of a skin augmentation composition to a skin of a subject, the microneedle comprising:
  a skeleton made of a rigid material, the skeleton comprises:
    a sharp tip section located on one end of the skeleton, the sharp tip section being configured to penetrate a skin of a subject;
    a base on an opposing end of the skeleton; and
    a middle section connecting between the sharp tip section and the base; and
  a skin augmentation composition, wherein the augmentation composition at least partly surrounds the middle section, such that a diameter of the sharp tip section is larger than a diameter of the augmentation composition.

According to some embodiments, the applicator and/or microneedle of the invention are configured for administration of a skin augmentation composition to a skin of a subject or a sub-cutis of a subject or a combination thereof. Each possibility represents a separate embodiment of the present invention.

According to some embodiments, the term "skin augmentation" refers to increasing the volume of the treated skin and/or sub-cutis. According to some embodiments, the term "skin augmentation" refers to increasing the apparent volume of the treated skin.

According to some embodiments, the substrate is in a form selected from the group consisting of: a strip and a patch. Each possibility represents a separate embodiment of the present invention. According to some embodiments, the substrate is in the form of a strip. According to some embodiments, the substrate is in the form of a patch. A strip is currently a preferred embodiment since it allows more precise placement than other configurations.

As used herein, the term "strip" refers to a longitudinal shape having a first end and a second end. According to some embodiments, the substrate comprises a first surface intended for being proximal to the skin and a second surface facing away from the skin. As used herein, the term "proximal" refers to a side which is close to the skin of a subject. As used herein, the term "proximal side" and "proximal part" are interchangeable. According to some embodiments, the terms "the proximal surface". "the surface intended for being placed proximal to the skin of a subject" and "the inner surface" are used interchangeably. As used herein, the terms "patient" and "subject" are used interchangeably.

According to some embodiments, the microneedles are located on at least part of the proximal surface of the substrate. According to some embodiments, at least part of the proximal surface of the substrate comprises an adhesive. According to some embodiments, the microneedles are not co-localized with the adhesive on the proximal surface of the substrate. According to some embodiments, the microneedles are co-localized with the adhesive on the proximal surface of the substrate. According to some embodiments, the microneedles are at least partially co-localized with the adhesive on the proximal surface of the substrate. As used herein, the term "co-localized" refers to being situated at the same two-dimensional coordinates.

According to some embodiments, the substrate is flexible. According to some embodiments, the applicator is adaptable to the outlines of a skin which requires augmentation. According to some embodiments, the substrate is adaptable to the outlines of a skin which requires augmentation. In a non-limiting example, the applicator of the invention may be applied to a subject's face such that it adapts to the outlines and contours of the face. Applying the flexible applicator to a subject's face such that the applicator adapts to the outline of the face may enable efficient delivery of the skin augmentation composition to the desired site. According to some embodiments, the applicator is curved. According to some embodiments, the applicator is curved so as to fit to the contours of a skin which requires augmentation. According to some embodiments, the substrate is rigid (not flexible).

According to some embodiments, the applicator comprises a plurality of segments. According to some embodiments, the segments are configured to flexibly move relative to one another. According to some embodiments, each segment comprises an array of microneedles comprising the skin augmentation composition of the invention. According to some embodiments, each segment comprises a substrate and an array of microneedles comprising the skin augmentation composition of the invention. According to other embodiments, the applicator comprises a plurality of segments and a single array of microneedles. According to some embodiments, the segments are attached to one another. According to some embodiments, the segments are integrally formed with one another. An applicator comprising a plurality of segments configured to flexibly move relative to one another may enable precise placement of the applicator over the undesired lines, wrinkles, depressed scars or folds to be treated. According to some embodiments, the size and/or number of the segments varies so as to enable precise placement of the applicator over the lines, wrinkles, depressed scars or folds to be treated. Each possibility represents a separate embodiment of the present invention. According to some embodiments, the applicator comprises segments of different sizes. As used herein, the terms "a plurality of" and "a multiplicity of" are used interchangeably and refer to at least two. As used herein, the terms "made of" and "composed of" are used interchangeably. According to some embodiments, the applicator further comprises a removable shield or cover or sheath configured to protect the microneedles prior to insertion into a subject.

According to some embodiments, the applicator may be of any shape and size. According to some embodiments, the substrate may be of any shape and size. According to other embodiments, the applicator is of a shape and size enabling efficient delivery of a skin augmentation composition to a subject in need thereof. According to some embodiments, the applicator is of a shape and size which fit treatment areas on a subject. Non-limiting examples are strips, which may fit longitudinal lines or wrinkles, and patches which may fit larger skin folds, depressed scars or defects to be treated.

According to other embodiments, different applicators according to the invention may comprise different amounts of skin augmentation composition. According to some embodiments, different microneedles within the same applicator comprise a different amount of skin augmentation composition. According to other embodiments, different applicators of the invention may comprise different numbers of microneedles. According to some embodiments, the microneedles comprised in the applicators of the inventions may be arranged in different conformations. According to some embodiments, the microneedles comprised in the applicators of the invention may be of different sizes. According to some embodiments, the microneedles comprised in the applicator of the invention are arranged as a single array. According to some embodiments, the microneedles comprised in the applicator of the invention are arranged as multiple arrays. According to some embodiments, the microneedles comprised in the applicator of the invention are arranged as multiple arrays, wherein each array is comprised in a different segment of the applicator. According to some embodiments, the spacing between each 2 microneedles in the same microneedles array is between 0.1-2 mm. According to some embodiments, the spacing between each 2 microneedles in the same microneedles array is at least 0.1, 0.2, 0.3, 0.4, 0.5, 0.6, 0.7, 0.8, 0.9, 1, 1.2, 1.4, 1.6, 1.8, 2 mm. Each possibility represents a separate embodiment of the present invention. According to some embodiments, the spacing between each 2 microneedles in the same microneedles array is at least spacing which enables flexibility of the applicator of the invention and/or adaptability of the applicator to the outlines of a skin which requires augmentation. Each possibility represents a separate embodiment of the present invention.

As used herein, the term "biodegradable" refers to a material which is naturally degraded when in a subject's body, by enzymatic activity, chemical dissolution or otherwise. As used herein, the term "biocompatible" refers to a material which does not elicit any undesirable and/or toxic local or systemic effects when administered to a subject.

According to some embodiments, the substrate may be of any material known in the art, as long as it is able to support microneedles and a skin augmentation composition. According to some embodiments, the substrate is made of a non-biodegradable material. According to some embodiments, the substrate is made of a rigid material. Non-limiting examples of materials suitable for making the substrate are: a metal, a polymer, medical plastic, a rubber, latex or a combination thereof. Each possibility represents a separate embodiment of the present invention. Suitable polymers for making the applicator may include, for instance, polyethylene terephthalate, polyvinylchloride, polyethylene, polypropylene, polycarbonate, polyester, and so forth. According to some embodiments, at least part of the substrate is made of a rigid material. According to some embodiments, at least part of the substrate is made of a flexible material.

According to some embodiments, the substrate and the base of the microneedles are made of a non-biodegradable material. As used herein, the base of the microneedle refers to the base of the microneedle's skeleton. According to some embodiments, the skeleton of the microneedles and at least part of the substrate are made of a non-biodegradable material. According to some embodiments the base of the microneedles and at least part of the substrate are made of a unitary piece of a non-biodegradable material. According to some embodiments, the base of the microneedles and at least part of the substrate are integrally formed. According to some embodiments, the skeleton of the microneedles and at least part of the substrate are made of a unitary piece of a non-biodegradable material. According to some embodiments, the skeleton of the microneedles and at least part of the substrate are integrally formed. According to some embodiments, the skeleton of the microneedles and at least part of the substrate are made of metal. According to some embodiments, the skeleton of the microneedle is integrally formed with at least part of the surface of the substrate intended for being placed proximal to the skin of a subject. According to some embodiments, the skeleton of the microneedle is attached to the substrate. According to some embodiments, the skeleton of the microneedle is attached to the surface of the substrate intended for being placed proximal to the skin of a subject. According to some embodiments, the skeleton of the microneedle is at least partly inserted into the substrate. According to some embodiments, microneedles having a skeleton at least partly inserted into the substrate of the applicator are more stably secured to the substrate than microneedles that are attaches and/or integrally formed with the substrate. Each possibility represents a separate embodiment of the present invention.

According to some embodiments, the middle section of the microneedle's skeleton passes through a tight-fitting opening in the skeleton's base and is at least partly inserted into the substrate or the substrate surface intended for being placed proximal to the skin of a subject. Each possibility represents a separate embodiment of the present invention. According to some embodiments, the middle section of the microneedle's skeleton passes through a tight-fitting opening in the skeleton's base and is at least partly inserted into the substrate or the substrate surface intended for being placed proximal to the skin of a subject, such that the middle section is perpendicular to the base and the substrate. Each possibility represents a separate embodiment of the present invention.

According to some embodiments, the middle part of the microneedle is the part of the microneedle comprised in between the sharp tip section of the microneedle's skeleton and the base of the microneedle's skeleton, comprising the middle section of the microneedle's skeleton and the augmentation composition. According to some embodiments, only the middle part of the microneedle comprises the skin augmentation composition. According to some embodiments, the sharp tip section of the microneedle's skeleton does not contain the skin augmentation composition. According to some embodiments, the base of the microneedle does not contain the skin augmentation composition.

According to some embodiments, the applicator is configured to be applied by a medical professional. According to some embodiments, the applicator is configured for self-application. It is to be understood that a subject may be able to use the applicator and methods of the invention without the help of a trained medical professional. According to some embodiments, the applicator is disposable after a single use. According to some embodiments, following removal of the applicator from the skin of the subject the applicator is substantially devoid of blood or other biohazardous substances following use of the applicator. As used herein "substantially devoid" is devoid other than trace amounts.

According to some embodiments, at least part of the applicator is substantially transparent. According to some embodiments, at least part of the substrate is substantially transparent. According to some embodiments, only the part of the applicator comprising the microneedles is substantially transparent. According to some embodiments, only the part of the substrate comprising the microneedles is substantially transparent. According to some embodiments, at least the part of the substrate not comprising an adhesive surface is substantially transparent. As used herein, "substantially transparent" refers to a material having an opacity level which enables seeing the skin to be treated through the material. Using an applicator comprising a substrate which is substantially transparent, according to the present invention, may enable seeing the site of skin defect or deficiency through the applicator and thus enable accurate placement of the applicator. According to some embodiments, at least part of the substrate and/or at least part of the microneedles are substantially transparent. According to some embodiments, at least part of the substrate is not transparent. Each possibility represents a separate embodiment of the present invention.

According to some embodiments, at least part of each microneedle is substantially transparent. According to some embodiments, at least part of the microneedle's skeleton is substantially transparent. According to some embodiments, the microneedle's skeleton is substantially transparent. According to some embodiments, at least the base of the microneedles is substantially transparent. According to some embodiments, at least the base of the microneedles and a part of the substrate are substantially transparent. According to some embodiments, at least part of the substrate is substantially transparent and the microneedles are not substantially transparent. According to some embodiments, clearly visible microneedles which are not substantially transparent, comprised in a substantially transparent substrate according to the invention, assist in placing the applicator accurately over the site of skin defect or deficiency.

According to some embodiments, the applicator further comprises a marking indicating the location of the array of microneedles on the substrate. According to some embodiments, the marking indicating the location of the array of microneedles on the substrate is on the surface of the substrate facing away from the skin. According to some embodiments, the marking indicating the location of the array of microneedles on the substrate is on the surface proximal to the skin. According to some embodiments, the marking indicating the location of the array of microneedles on the substrate is both on the surface of the substrate facing away from the skin and the surface of the substrate proximal to the skin. According to some embodiments, the marking is in the form of dots or the like, each dot representing the location of a single microneedle in the microneedle array. According to some embodiments, the marking delineates the general location of the entire microneedle array on the substrate. According to some embodiments, the marking indicating the location of the array of microneedles on the substrate assists in accurately placing the applicator over the site of skin defect or deficiency, thus delivering the skin augmentation composition to the exact site of skin defect or deficiency.

Non-limiting examples of a skin defect or deficiency, according to some embodiments of the present invention, are selected from the group consisting of: undesired lines, wrinkles, folds, depressed scars, areas of skin or sub cutis deficiency or a combination thereof. Each possibility represents a separate embodiment of the present invention.

As used herein, the terms "composition". "the composition of the invention" "augmentation composition", "a soft tissue augmentation composition" and "skin augmentation composition" are used interchangeably and refer to a composition comprising at least one biocompatible skin augmentation material. It is to be understood that a skin augmentation composition according to the present invention is suitable for filling of skin, of sub-cutis or a combination thereof.

Preferably, skin augmentation materials which may be comprised in the composition of the invention are effective dermal fillers approved by the U.S. Food and Drug administration, including but not limited to fillers comprising structural proteins, polysaccharides or synthetic polymers. In certain embodiments, the biocompatible skin augmenting material is calcium-hydroxyapatite or calcium-hydroxylapatite. In certain embodiments, the biocompatible skin augmenting material is hyaluronic acid. Hyaluronic acid according to the present invention includes both non-cross-linked and/or cross-linked hyaluronic acid derivatives as are well known in the art, and can be in liquid, semi solid or solid states. In certain embodiments, the biocompatible skin augmenting material is in the form of solid particles or solid spheres. Exemplary embodiments of skin augmentation materials that may be used include collagen, such as reconstituted bovine collagen products including, but not limited to, ZYDERM I®, ZYDERM II® and ZYPLAST® (Collagen Corporation); natural human collagen COSMODERM™ and COSMOPLAST™ (INAMED); and endogenous collagen from the subject, AUTOLOGEN® produced by Collagenesis. Additional examples of dermal fillers may be selected from those comprising hyaluronic acid, including but not limited to, products such as HYLAFORM® gel manufactured by INAMED and Genzyme Corporations, derived from the rooster combs of domestic fowl; and RESTYLANE® manufactured by Medicis, a hyaluronic acid derivative derived from streptococcal bacterial fermentation. Each possibility represents a separate embodiment of the present invention. According to some embodiments, collagen according to the invention is selected from the group consisting of: allogeneic collagen, xenogeneic collagen and a combination thereof. Each possibility represents a separate embodiment of the present invention. According to other embodiments, a skin augmentation material is human cadaveric dermis cultivated from a cadaver, such as, but not limited to, the materials having the brand names Cymetra, Dermalogen, Alloderm and Fascian.

As used herein, the terms "biocompatible ceramic skin augmentation material", "biocompatible ceramic soft tissue augmentation material", "biocompatible ceramic agent", "biocompatible ceramic" and "biocompatible ceramic material" are used interchangeably. As used herein, the term "biocompatible ceramic material", refers to a biocompatible skin augmentation material having ceramic properties. According to some embodiments, the biocompatible ceramic material is an inorganic ceramic material, such as, but not limited to, hydroxyapatite. According to some embodiments, the biocompatible ceramic material is water-insoluble. According to some embodiments, the biocompatible ceramic material is a calcium phosphate ceramic material. According to some embodiments, the biocompatible ceramic material is hydroxyapatite. As used herein, the terms "hydroxyapatite", "hydroxylapatite", "calcium hydroxyapatite" and "calcium hydroxylapatite" are interchangeable. According to some embodiments, hydroxyapatite as used herein refers to a salt or derivative of hydroxyapatite.

A non-limiting example of a skin augmentation composition comprising a biocompatible ceramic material is RADIESSE® manufactured by Merz Aesthetics, comprising calcium hydroxylapatite beads suspended in a gel carrier that consists primarily of sterile water, water for injection, glycerin and sodium carboxymethylcellulose.

According to some embodiments, a biocompatible ceramic material is biodegradable. According to some embodiments, a biocompatible ceramic material is capable of undergoing biodegradation not less than 1, 2, 3, 4 weeks following administration to a subject. Each possibility represents a separate embodiment of the present invention. According to some embodiments, a biocompatible ceramic material is capable of undergoing biodegradation not less than 1, 2, 3, 4, 5, 6, 7, 8, 9, 10, 11, 12 months following administration to a subject. Each possibility represents a separate embodiment of the present invention. According to some embodiments, a biocompatible ceramic material is capable of undergoing biodegradation not less than 0.5, 1, 2, 3 years following administration to a subject. Each possibility represents a separate embodiment of the present invention. Typically, a biocompatible ceramic material is capable of undergoing biodegradation not less than 12 months following administration to a subject.

According to some embodiments, the biodegradation of a biocompatible ceramic material is significantly slower than biodegradation of skin augmentation materials selected from the group consisting of: bovine collagen, porcine collagen, recombinant collagen, human collagen, hyaluronic acid and hyaluronic acid derivatives, gelatin matrices and combinations thereof. Each possibility represents a separate embodiment of the present invention.

According to some embodiments, the biocompatible ceramic material is in the form of beads and/or particles. Each possibility represents a separate embodiment of the present invention. According to some embodiments, the biocompatible ceramic material comprises beads and/or particles having the same/different sizes. Each possibility represents a separate embodiment of the present invention. According to some embodiments, the biocompatible ceramic material is in the form of beads and/or particles of a size suitable for the size of the treated area. Each possibility represents a separate embodiment of the present invention. According to some embodiments, applicators which contain large beads of a biocompatible ceramic material are suitable for treating deep and/or large lines, wrinkles or folds.

According to some embodiments, the biocompatible ceramic material comprises beads and/or particles having a size of up to 5, 10, 20, 30, 40, 50, 60, 70, 80, 90, 100 μm. Each possibility represents a separate embodiment of the present invention. According to some embodiments, the biocompatible ceramic material comprises beads and/or particles having a size of 25-45 μm. Each possibility represents a separate embodiment of the present invention. According to some embodiments, the biocompatible ceramic material comprises beads and/or particles having a size of 10-50 μm. Each possibility represents a separate embodiment of the present invention. According to some embodiments, the biocompatible ceramic material comprises beads and/or particles having a size of 5-20 µm. Each possibility represents a separate embodiment of the present invention. According to certain embodiments, the biocompatible ceramic material comprises beads and/or particles having a size of about 40 µm. Each possibility represents a separate embodiment of the present invention. According to some embodiments, the biocompatible ceramic material particles are of about 10-100 micrometers, preferably of about 40 micrometers. Each possibility represents a separate embodiment of the present invention.

According to some embodiments, the skin augmentation composition comprises at least 1, 2, 3, 4, 5, 10, 15, 25, 30, 40, 50, 60, 70, 80, 90, 95 percent biocompatible ceramic material. Each possibility represents a separate embodiment of the present invention. According to some embodiments, the skin augmentation composition comprises at least 30% biocompatible ceramic material.

According to some embodiments, the composition of the invention comprises at least one biodegradable carrier. According to some embodiments, the composition of the invention comprises at least one biocompatible ceramic and at least one biodegradable carrier. According to some embodiments, the composition of the invention comprises at least one biocompatible ceramic, at least one biodegradable carrier and at least one additional skin augmentation material. According to some embodiments, the composition of the invention comprises hydroxyapatite and at least one biodegradable carrier. According to some embodiments, the composition of the invention comprises hydroxyapatite and polyethylene glycol. According to some embodiments, the composition of the invention comprises hydroxyapatite, polyethylene glycol and magnesium sulfate.

According to some embodiments, the biodegradable carrier is selected from the group consisting of: a salt, a biodegradable polymer and a combination thereof. Each possibility represents a separate embodiment of the present invention. According to some embodiments, the biodegradable carrier is a salt. According to some embodiments, the salt is a water-soluble salt. According to some embodiments, the salt is selected from the group consisting of: sodium sulfate, sodium chloride, magnesium sulfate, magnesium citrate, magnesium chloride and a combination thereof. Each possibility represents a separate embodiment of the present invention.

According to some embodiments, the biodegradable carrier is a biodegradable polymer. According to some embodiments, the biodegradable polymer is a polymer selected from the group consisting of: Polyethylene glycol (PEG), Polyglactin 910, Polyglecaprone 25, Polydioxanone, Lactomer 9-1, Glycomer 631, Polyglyconate and combinations thereof. Each possibility represents a separate embodiment of the present invention. According to some embodiments, the biodegradable carrier is magnesium sulfate and/or polyethylene glycol. Each possibility represents a separate embodiment of the present invention. According to some embodiments, PEG as used herein has a molecular weight between 20 and 50 kDa. According to some embodiments, a biodegradable carrier comprising PEG of 20-50 kDa has a thick paste consistency. According to some embodiments, the biodegradable carrier is Polyglactin 910 and/or magnesium sulfate. Each possibility represents a separate embodiment of the present invention.

According to some embodiments, the biodegradable carrier is degradable within 1, 2, 3, 4, 5, 6, 7, 8, 9, 10, 12 hours of inserting the microneedles into the skin of a subject Each possibility represents a separate embodiment of the present invention. According to some embodiments, the biodegradable polymer is degradable within 1, 2, 3, 4, 5, 6, 7, 8, 9, 10, 12 hours of inserting the microneedles into the skin of a subject. Each possibility represents a separate embodiment of the present invention. According to some embodiments, the biodegradable carrier is degradable within 0.5, 1, 2, 3, 4, 5, 6, 7 days of inserting the microneedles into the skin of a subject Each possibility represents a separate embodiment of the present invention. According to some embodiments, the biodegradable polymer is degradable within 0.5, 1, 2, 3, 4, 5, 6, 7 days of inserting the microneedles into the skin of a subject. Each possibility represents a separate embodiment of the present invention. Typically, the biodegradable carrier undergoes biodegradation within less than 7 days of inserting the microneedles into the skin of a subject, preferably less than 2 days, most preferably less than 1 day. Each possibility represents a separate embodiment of the present invention. Without wishing to be bound by any theory or mechanism, rapid biodegradation of the biodegradable carrier within hours/days of introduction into the body of a subject results in uniform distribution of the biocompatible ceramic material and/or the skin augmentation material in the treated area, thus achieving uniform filing of the treated skin defect/deficiency. According to some embodiments, following insertion of the composition of the invention to the skin of the subject, the biodegradable carrier undergoes biodegradation and the biocompatible ceramic remains within the skin of a subject for at least several months, preferably up to a year, most preferably more than a year. Each possibility represents a separate embodiment of the present invention.

According to some embodiments, insertion of microneedles comprising the skin augmentation composition to the skin of a subject results in biodegradation of fast-degrading elements in the composition, thus resulting in release of the biocompatible ceramic into the treated area. According to some embodiments, the fast-degrading element is a biodegradable carrier such as, but not limited to, magnesium sulfate and/or polyethylene glycol. Each possibility represents a separate embodiment of the present invention. It is to be understood that, according to some embodiments, biodegradation of elements in the composition such as a biodegradable carrier assist in homogenous spreading of the biocompatible ceramic in the treated area. According to some embodiments, following biodegradation of fast-degrading elements, such as a biodegradable carrier, the biocompatible ceramic is transferred from the microneedle to the treated area. As used herein, fast-degrading elements refer to elements within the composition of the invention which undergo biodegradation within hours or up to 7 days from insertion of the microneedles of the invention into the skin of a subject. It is to be understood that a biocompatible ceramic is not a fast-degrading element of the composition of the invention. According to some embodiments, following administration of the applicator of the invention for a desired period of time, the applicator and the microneedles are removed from the subject, while at least part of the composition remains in the treated area.

According to some embodiments, the biodegradable carrier comprises sterile water for injection and/or glycerin and/or sodium carboxymethylcellulose. Each possibility represents a separate embodiment of the present invention. According to some embodiments, the biodegradable carrier comprises water, glycerin and carboxymethylcellulose. According to some embodiments, the biodegradable carrier comprises carboxymethylcellulose.

According to some embodiments, the composition of the invention comprises a biocompatible material in the form of beads and/or particles. Each possibility represents a separate embodiment of the present invention. According to some embodiments, the composition of the invention comprises a biocompatible material in the form of beads and/or particles surrounded by at least one biodegradable carrier. Each possibility represents a separate embodiment of the present invention. According to some embodiments, the composition of the invention comprises a biocompatible material in the form of beads and/or particles surrounded by at least one biodegradable polymer. Each possibility represents a separate embodiment of the present invention. According to some embodiments, the composition of the invention comprises a biocompatible material in the form of beads and/or particles surrounded by at least one salt. Each possibility represents a separate embodiment of the present invention. According to some embodiments, the composition of comprises a biocompatible material in the form of beads and/or particles surrounded by at least one biodegradable carrier. According to some embodiments, the composition of the invention comprises hydroxyapatite in the form of beads and/or particles. Each possibility represents a separate embodiment of the present invention. According to some embodiments, the composition of the invention comprises hydroxyapatite in the form of beads and/or particles surrounded by at least one biodegradable carrier. According to some embodiments, the composition comprises a biocompatible hyaluronic acid derivates in the form of beads and/or particles surrounded by at least one biodegradable carrier. Each possibility represents a separate embodiment of the present invention.

Without wishing to be bound by any theory or mechanism, beads or particles of a biocompatible ceramic material such as, but not limited to, hydroxyapatite, surrounded by a biodegradable carrier, may homogeneously spread in the treated area upon degradation of the biodegradable carrier by dissolution, enzymatic activity and the like.

According to some embodiments, adding a biodegradable polymer to the composition of the invention results in a composition having a gel, a paste or a solid like consistency. Each possibility represents a separate embodiment of the present invention. According to some embodiments, a gel, a paste or a solid like composition may be easily inserted into the middle part of the microneedles of the invention. According to some embodiments, addition of a salt to the composition of the invention assists in uniform dispersion of the biocompatible augmentation particles or beads within the composition. Without wishing to be bound by any theory or mechanism, addition of a salt to the composition of the invention may result in water diffusion into the composition, thus assisting in uniform dispersion of the biocompatible ceramic within the composition and/or within the treated area.

As used herein, the terms "skin augmentation material" and "filler" refer to agents and compositions useful for augmentation of skin defects. According to some embodiments, a skin augmentation material is a dermal and/or sub-dermal filler. Each possibility represents a separate embodiment of the present invention. Suitable skin augmentation materials according to the invention include, but are not limited to, proteins, polysaccharides, lipids, synthetic polymers and combinations thereof. Each possibility represents a separate embodiment of the present invention. According to some embodiments, a skin augmentation material according to the invention is any material known in the art which is suitable for filling undesired fold, wrinkle, depressed scar or line in a skin of a subject. According to some embodiments, a skin augmentation material according to the invention is any skin augmentation material which may be delivered using microneedles. According to some embodiments, a biocompatible ceramic material is a skin augmentation material. According to certain embodiments, a skin augmentation material refers to a biocompatible, inert material. "Inert material" as used herein refers to a non-antigenic, non-carcinogenic, non-teratogenic, and non-migratory augmentation material.

According to some embodiments, skin augmentation materials include allogeneic products, xenogeneic products and synthetically derived products. Each possibility represents a separate embodiment of the present invention.

According to some embodiments, the skin augmentation composition comprises at least one biocompatible ceramic material and at least one additional type of skin augmentation material. According to some embodiments, the composition of the invention further comprises at least one skin augmentation material selected from the group consisting of: a biodegradable natural substance, a biodegradable synthetic polymer, a non-biodegradable synthetic polymer and combinations thereof. Each possibility represents a separate embodiment of the present invention. According to some embodiments, the composition of the invention further comprises at least one skin augmentation material selected from the group consisting of: a biodegradable natural substance, a biodegradable synthetic polymer, a non-biodegradable synthetic polymer, a non-biodegradable natural substance and combinations thereof. Each possibility represents a separate embodiment of the present invention.

According to some embodiments, a biodegradable natural substance is selected for example from the group consisting of: bovine collagen, porcine collagen, recombinant collagen, human collagen, gelatin, hyaluronic acid, hyaluronic acid derivative (in liquid, semi-solid and solid states), dried acellular particulate dermal matrix, allogeneic fat and combinations thereof. Each possibility represents a separate embodiment of the present invention.

According to some embodiments, a biodegradable synthetic polymer is selected for example from the group consisting of: poly-L-lactic acid, polyethylene oxide, carboxymethylcellulose and combinations thereof. Each possibility represents a separate embodiment of the present invention.

According to some embodiments, a non-biodegradable synthetic polymers is selected for example from the group consisting of: polymethyl methacrylate (PMMA), polymethyl methacrylate beads, silicones, silicone rubber, expanded polytetrafluoroethylene (ePTFE), polyacrylamide, polyalkylimide and combinations thereof. Each possibility represents a separate embodiment of the present invention.

According to some embodiments, the skin augmentation composition of the invention comprises at least one a skin augmentation material and at least one dispersant material. According to some embodiments, the skin augmentation composition of the invention comprises a combination of materials comprising at least one biocompatible ceramic material and at least one type of skin augmentation material other than a biocompatible ceramic material. According to some embodiments, the skin augmentation composition comprises at least one biocompatible, biodegradable carrier and at least one type of skin augmentation material selected from the group consisting of: a biodegradable natural substance, a biodegradable synthetic polymer, a non-biodegradable synthetic polymer and combinations thereof. Each possibility represents a separate embodiment of the present invention.

According to some embodiments, the skin augmentation composition comprises hydroxyapatite. According to some embodiments, the skin augmentation composition comprises hydroxyapatite and at least one type of skin augmentation material other than hydroxyapatite. According to some embodiments, the skin augmentation composition comprises at least one type of soft-tissue augmentation material selected from the group consisting of: a biodegradable natural substance, a biodegradable synthetic polymer, a non-biodegradable synthetic polymer, a non-biodegradable natural substance and combinations thereof. Each possibility represents a separate embodiment of the present invention. According to some embodiments, the skin augmentation composition comprises at least one type of soft-tissue augmentation material selected from the group consisting of: a biodegradable natural substance, a biodegradable synthetic polymer, a non-biodegradable synthetic polymer and combinations thereof. Each possibility represents a separate embodiment of the present invention.

According to some embodiments, the composition of the invention comprises less than 50% weight percent water-soluble skin augmentation materials such as, but not limited to, collagen, hyaluronic acid and gelatine. Each possibility represents a separate embodiment of the present invention.

According to some embodiments, the microneedles of the invention comprise a biologically active agent. According to some embodiments, the composition of the invention comprises a biologically active agent. According to some embodiments, the biologically active agent is selected from the group consisting of: an enzyme, a drug, a toxin and a combination thereof. Each possibility represents a separate embodiment of the present invention.

According to some embodiments, the drug is an analgesic. According to some embodiments, when the applicator of the invention is used to deliver skin augmentation composition subcutaneously, at least one analgesic is co-delivered by the applicator of the invention together with the skin augmentation composition. According to some embodiments, the skin augmentation composition of the invention further comprises an analgesic. According to some embodiments, the methods of the invention further comprise administration of an analgesic. According to some embodiments, every analgesic known in the art may be used with the present invention, such as, but not limited to: lidocaine, paracetamol, non-steroidal anti-inflammatory drug (NSAID), COX-2 inhibitor, opiates or morphinomimetics. Each possibility represents a separate embodiment of the present invention. According to some embodiments, an analgesic which may be used with the present invention is lidocaine.

According to some embodiments, the drug is a drug known in the art to assist in filling undesired lines, wrinkles, folds and the like. According to some embodiments, examples of drugs which may be comprised in the composition of the invention include, but are not limited to, anti-psoriasis drugs, muscle relaxants and a combination thereof. Each possibility represents a separate embodiment of the present invention.

According to some embodiments, the drug is a drug for treatment of pathological scarring. According to some embodiments, the drug for treatment of pathological scarring is a corticosteroid. According to some embodiments, the corticosteroid is any corticosteroid known in the art for treatment of pathological scarring, such as, but not limited to triamcinolone.

According to some embodiments, the toxin is botulinum toxin. According to some embodiments, the composition of the invention comprises botulinum toxin. According to some embodiments, the applicator of the invention comprises botulinum toxin.

According to some embodiments, the skin augmentation composition of the invention further comprises a medical pigment. According to some embodiments, the microneedles of the invention comprise a medical pigment. As used herein, the term "medical pigment" refers to a color material suitable for insertion into the skin of a subject. According to some embodiments, medical pigments have a regulatory approval for insertion into a skin of a subject. According to some embodiments, medical pigments are pigments known in the art to be suitable for micro-pigmentation treatments. In non-limiting examples, medical pigments suitable for use according to the present invention include, but are not limited to, pigments such as BIOCHROMADERM® (Biotic Phocea) or the Signature Series (Micro-Pigmentation Centre. Inc.). Possible medical pigments for use with the applicator of the present invention may be pigments for scar camouflage, areola reconstruction or lip remodeling.

According to some embodiments, a microneedle comprising a medical pigment is suitable for micro-pigmentation treatments. According to some embodiment, micro-pigmentation treatments are selected from the group consisting of: concealment of scars, concealment and/or blurring of skin pigmentation, nipple areola construction and/or augmentation, correction of freckles, lip coloring, eyebrow coloring and a combination thereof. Each possibility represents a separate embodiment of the present invention. According to some embodiments, the microneedles of the invention comprise a composition comprising a medical pigment According to some embodiments, the applicator of the invention comprises microneedles comprising a medical pigment without a biocompatible ceramic or a skin augmentation composition. Each possibility represents a separate embodiment of the present invention.

According to some embodiments, the present invention provides an applicator configured for administration of a medical pigment to a skin of a subject, the applicator comprising a substrate and an array of microneedles; wherein the substrate has a generally flattened structure having two opposing surfaces, wherein one surface is intended for being placed proximal to the skin of a subject and the other surface facing away from the skin of the subject; wherein the array of microneedles is located on the surface proximal to the skin of the subject, the array comprising a multiplicity of microneedles, wherein each of the microneedles comprises a composition comprising at least one medical pigment. According to some embodiments, the applicator is configured for administration of a medical pigment to a skin of a subject and/or to sub-cutis layers of a subject. Each possibility represents a separate embodiment of the present invention.

According to some embodiments, the microneedles comprise a skeleton made of a rigid material, the skeleton comprising: a sharp tip section located on one end of the skeleton configured to penetrate a skin of a subject, a base on an opposing end of the skeleton and a middle section connecting the sharp tip section and the base; and a composition comprising a medical pigment, wherein the composition at least partly surrounds the middle section, such that a diameter of the sharp tip section is larger than a diameter of the composition.

According to some embodiments, the present invention provides a method for performing a micro-pigmentation treatment on a subject, the method comprises administering to the subject an applicator configured for administration of a medical pigment to a skin of a subject, the applicator comprising a substrate and an array of microneedles; wherein the substrate has a generally flattened structure having two opposing surfaces, wherein one surface is intended for being placed proximal to the skin of a subject and the other surface facing away from the skin of the subject; wherein the array of microneedles is located on the surface proximal to the skin of the subject, the array comprising a multiplicity of microneedles, wherein each of the microneedles comprises a composition comprising at least one medical pigment.

According to some embodiments, the applicator of the invention comprises microneedles. According to other embodiments, the applicator of the invention comprises an array of microneedles. According to other embodiments, the applicator of the invention comprises at least one array of microneedles. An array of microneedles may include a mixture of microneedles having, for example, various lengths, diameters, cross-sectional shapes, and spacing between the microneedles. Each possibility represents a separate embodiment of the present invention. According to some embodiments, the length of the microneedles of the invention is typically between about 0.05 and 1 mm, preferably between 10 microns (urn) and 500 microns (urn), and more preferably between 30 and 200 microns (urn). Each possibility represents a separate embodiment of the present invention. The length of the microneedles may be selected according to the particular application or treated tissue. Each possibility represents a separate embodiment of the present invention. For certain applications it may be desirable to use microneedles of slightly greater dimensions. Thus, according to some embodiments, the length of the microneedles of the invention is above 1 mm. According to additional embodiments, the length of the microneedles of the invention is up to 2 mm.

According to some embodiments, microneedles longer than 1 mm may be used to deliver the skin augmentation composition subcutaneously. According to some embodiments, microneedles may be used to deliver the skin augmentation composition to areas having deep wrinkles and/or skin deficiency. Each possibility represents a separate embodiment of the present invention. According to some embodiments, microneedles longer than 1 mm may be used to deliver the skin augmentation composition to areas having deep wrinkles and/or skin or sub cutis deficiency. Each possibility represents a separate embodiment of the present invention.

According to some embodiments, the applicator of the invention comprises microneedles having various lengths. According to some embodiments, the applicator of the invention comprises microneedles having variable lengths and/or variable degrees of thickness. Each possibility represents a separate embodiment of the present invention. According to some embodiments, the applicator of the invention comprises microneedles having variable lengths and/or variable degrees of thickness in correlation to the location of the microneedles on the substrate. Each possibility represents a separate embodiment of the present invention. According to some embodiments, the applicator of the invention comprises microneedles having variable lengths in correlation to the location in which they are configured to be situated within the area to be treated. Each possibility represents a separate embodiment of the present invention.

According to some embodiments, microneedles configured to be situated at a deeper point of a line, wrinkle or fold to be treated are longer than microneedles configured to be situated at a superficial point of the line, wrinkle or fold to be treated. In a non-limiting example, microneedles configured to be situated closer to the margins of a line, wrinkle or fold to be treated are shorter than microneedles configured to be situated in the center of the line, wrinkle or fold to be treated. According to some embodiments, microneedles situated at the center of the microneedle array are longer than microneedles situated near the margins of the microneedle array. An applicator comprising microneedles having variable lengths may be able to more precisely and uniformly fill a line, wrinkle or fold.

According to some embodiments, the applicator of the invention comprises microneedles having variable degrees of thickness in correlation to the location in which they are configured to be situated within the area to be treated. According to some embodiments, microneedles configured to be situated at a deeper point of a line, wrinkle or fold to be treated are thicker than microneedles configured to be situated at a superficial point of the line, wrinkle or fold to be treated.

FIG. 1A schematically illustrates a top view of applicator 100 according to some exemplary embodiments. According to the embodiments shown in FIG. 1A, applicator 100 includes a substrate 102 shown herein in the form of a rectangular patch, but may have any other form, such as but not limited to, a square, a circle, a strip or any other form. Substrate 102 is preferably made of a flexible material, such as, but not limited to, medical plastic, rubber or latex and is preferably configured to adapt to the curvature of the skin surface. Substrate 102 includes two surfaces: an inner surface 104 and an outer surface 106. Inner surface 104 is configured to be placed proximal to the skin (for example to adhere to the skin). Inner surface 104 includes microneedles array 108.

Figure 2A:
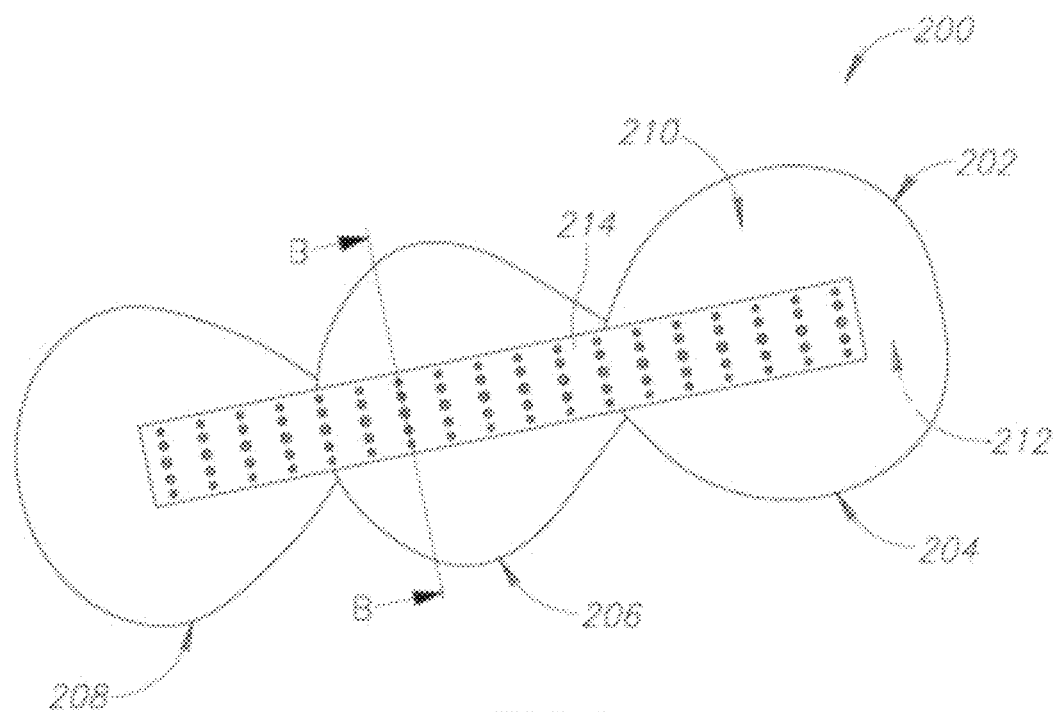
FIG. 2A schematically shows an applicator, according to some embodiments of the invention, in the form of a strip having several segments.

FIG. 2A schematically illustrates a top view of applicator 200 according to some exemplary embodiments. According to the embodiments shown in FIG. 2A, applicator 200 includes substrate 202 in the form of a strip composed of several segments 204, 206, and 208, but can have any other form, such as but not limited to, a rectangle, a square, a circle or any other form. Substrate 202 is preferably made of a flexible material, such as, but not limited to, medical plastic, rubber or latex and is preferably configured to adapt to the curvature of the skin surface. Segments 204, 206, and 208 are preferably configured to flexibly move relative to each other. Substrate 202 includes two surfaces: inner surface 210 and outer surface 212. Inner surface 210 is configured to be placed proximal to the skin (for example to adhere to the skin). Inner surface 210 includes microneedles array 214.

Figure 3:
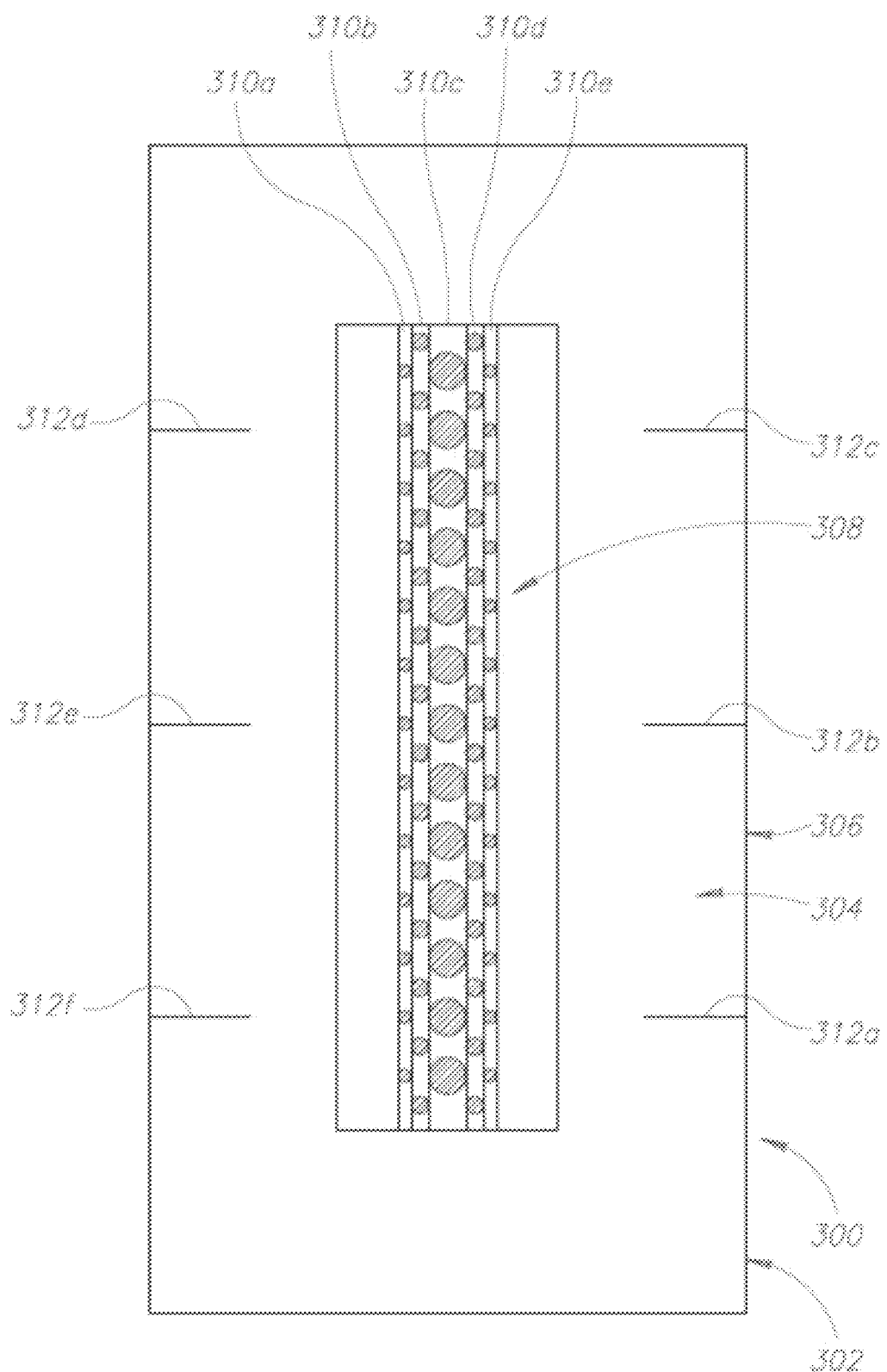
FIG. 3 schematically shows an applicator, according to some embodiments of the invention, in the form of a patch comprising microneedles of various degrees of thickness and having markings indicating the location of the microneedles on the applicator.

FIG. 3 schematically illustrates a top view of applicator 300 according to some exemplary embodiments, showing surface 304 of substrate 302. Surface 304 is intended for being placed proximal to the skin of a subject, while surface 306 is intended to face away from the subject. Surface 304 comprises microneedle array 308. Microneedle array 308 comprises five microneedle rows 310a, 310b, 310c, 310d, 310e, the microneedles being attached to or integrally formed with surface 304. Each possibility represents a separate embodiment of the present invention. Microneedles in microneedle row 310c, situated at the center of array 308 are thicker than microneedles 310b and 310d which are in turn thicker than microneedles 310a and 310e, situated closer to the ends/margins of array 308. According to some embodiments, thick microneedles are configured to deliver a larger amount of skin augmentation composition than thin microneedles. According to some embodiments, thick microneedles are configured to deliver a large amount of skin augmentation composition to the center/deep region of a wrinkle, line or the like to be treated, requiring higher augmentation than the ends and/or margins of a wrinkle, line or the like. According to other embodiments, thin microneedles are configured to deliver a low amount of skin augmentation composition to the ends and/or margins of a wrinkle, line or the like.

According to the embodiment depicted in FIG. 3, other than the part comprising microneedle array 308, substrate 302 is substantially transparent Substrate 302 comprises markings 312a, 312b, 312c, 312d, 312e, 312f indicating the location of microneedle array 308 on surface 304. According to some embodiments, markings 312a, 312b. 312c. 312d, 312e, 312f assist in correct placement of applicator 300 on the skin of a subject. According to some embodiments, markings 312a, 312b, 312c, 312d, 312e, 312f are on surface 304 and/or on surface 306. Each possibility represents a separate embodiment of the present invention.

As used herein, the term "microneedles" refers to protruding structures designed to pierce the skin and facilitate delivery of various types of compounds. According to some embodiments, microneedles facilitate delivery of the composition of the invention to dermal and/or sub-dermal compartments of the skin. Each possibility represents a separate embodiment of the present invention. According to some embodiments, subcutaneous delivery of a skin augmentation composition can be achieved by the applicator of the invention if the microneedles comprised in the applicator are longer than the thickness of the skin to be treated. According to some embodiments, the length of the microneedles comprised in the applicator of the invention is configured to allow dermal and/or subcutaneous delivery of a skin augmentation composition. Each possibility represents a separate embodiment of the present invention.

According to some embodiments, the length of the microneedles comprised in the applicator of the invention is configured to allow delivery of skin augmentation composition to the dermis and/or lower layers of the skin. According to some embodiments, the length of the microneedles' base section is comprised in the applicator, configured to allow delivery of skin augmentation composition to the dermis and/or lower layers of the skin. Each possibility represents a separate embodiment of the present invention. According to some embodiments, the microneedles comprised in the applicator of the invention are configured to allow delivery of a skin augmentation composition to the dermis and/or lower layers of the skin without delivery of skin augmentation composition to the epidermis layer of the skin. Each possibility represents a separate embodiment of the present invention. According to some embodiments, the length of the microneedles comprised in the applicator of the invention is configured not to allow delivery of skin augmentation composition to the epidermis. According to some embodiments, the length of the microneedle base is configured not to allow delivery of a skin augmentation composition to the epidermis layer of the skin. According to some embodiments, long microneedles enable delivery of skin augmentation composition to subcutaneously and/or to deep layers of the skin, such as, but not limited to, the hypodermis. Each possibility represents a separate embodiment of the present invention.

According to some embodiments, each microneedle according to the invention comprises the skin augmentation composition and a skeleton made of a rigid material. According to some embodiments, the rigid material is selected from a group consisting of: metal, plastic, a ceramic material, silicone and a combination thereof. Each possibility represents a separate embodiment of the present invention. According to some embodiments, the rigid material is biocompatible. According to some embodiments, the rigid material is biodegradable. According to some embodiments, the rigid material is rigid as to enable the microneedles to be propelled into the skin of the subject. According to some embodiments the rigid material is a metal. According to some embodiments, each microneedle according to the invention comprises the skin augmentation composition and a metal skeleton. According to some embodiments, the metal is selected from the group consisting of: stainless steel, titanium, iron, gold, silver, platinum and a combination and/or alloy thereof. Each possibility represents a separate embodiment of the present invention. According to some embodiments, rigid material is preferably a material approved by the US Food and Drug Association (FDA) for implantation and/or parenteral delivery. Each possibility represents a separate embodiment of the present invention.

According to some embodiments, the skeleton of the microneedles is removed from the subject upon removal of the applicator from the subject According to some embodiments, upon removal of the applicator of the invention from the skin of the subject the skeletons of the microneedles are removed while at least part of the composition of the invention remains within the skin or subcutaneous region of the subject's skin. Each possibility represents a separate embodiment of the present invention. According to some embodiments, upon removal of the applicator of the invention from the skin of the subject at least part of the biocompatible ceramic remains within the skin or subcutaneous region of the subject's skin, while the microneedles' skeletons are removed. Each possibility represents a separate embodiment of the present invention.

According to some embodiments, the skeleton of each microneedle comprises a sharp tip section, a base and a middle section connecting the sharp tip section and the base. As used herein, the terms "sharp tip section", "tip section" and "tip" are used interchangeably. According to some embodiments, the tip section, the base and the middle section of the skeleton are integrally formed. According to some embodiments, the tip section, the base and the middle section of the skeleton are made of a unitary piece of material. According to some embodiments, the tip section, the base and the middle section of the skeleton are attached to each other.

According to some embodiments, the sharp tip section of the microneedle's skeleton is the most proximal part of the microneedle. As used herein, the proximal side of the microneedle refers to the microneedle's side which is closest to the subject and farthest from the substrate of the applicator. The base part and the sharp tip section of the microneedle's skeleton are on opposing ends of the microneedle's skeleton. As used herein, the base of the microneedle refers to the side of the microneedle which is farthest from the subject and closest to the substrate's surface intended for being placed proximal to the skin of a subject. According to some embodiments, the base of the microneedle's skeleton is the base of the microneedle.

According to some embodiments, the sharp tip section of the microneedle's skeleton is configured to penetrate the skin of a subject. According to some embodiments, the sharp tip section is of any shape which enables it to penetrate the skin of a subject. According to some embodiments, the sharp tip section has a shape selected from the group consisting of:

a cone, a pyramid, a triangular pyramid and a polygonal pyramid. Each possibility represents a separate embodiment of the present invention. According to some embodiments, the sharp tip section is attached to the middle section of the microneedle's skeleton. According to some embodiments, the sharp tip section is integrally formed with the middle section of the microneedle's skeleton.

According to some embodiments, the diameter of the sharp tip section is larger than the diameter of the skin augmentation composition. According to some embodiments, the diameter of the sharp tip section is larger than the diameter of the microneedle's middle part. According to some embodiments, the largest diameter of the sharp tip section is larger than the largest diameter of the skin augmentation composition. According to some embodiments, the largest diameter (or cross section area) of the sharp tip section is the same as the largest diameter (or cross section area) of the skin augmentation composition. According to some embodiments, the largest diameter (or cross section area) of the sharp tip section is larger than the largest diameter (or cross section area) of the microneedle's middle part. As used herein, the diameter of the sharp tip section refers to the largest distance that can be formed between two opposite parallel lines tangent to the boundary of a cross section through the sharp tip section, wherein the cross-section is parallel to the substrate. According to some embodiments, the middle part of the microneedle comprises the middle section of the microneedle's skeleton and the augmentation composition. According to some embodiments, the middle part of the microneedle comprises the middle section of the microneedle's skeleton and the augmentation composition.

According to some embodiments, the sharp tip section punctures the skin of the subject enabling the insertion of the skin augmentation composition. According to some embodiments, a sharp tip section having a larger diameter than the diameter of the skin augmentation composition enables the formation of a skin puncture large enough for the skin augmentation composition to enter into the skin without spillage of the composition outside the body or within the epidermis. Each possibility represents a separate embodiment of the present invention.

According to some embodiments, the base of the microneedles does not comprise the skin augmentation composition. According to some embodiments, the skeleton's base has a shape selected from the group consisting of: a cylinder, a rectangular box, a cuboid, a triangular box and a polygonal box. Each possibility represents a separate embodiment of the present invention. According to some embodiments, the skeleton's base is configured to confer stability to the microneedle. According to some embodiments, the base of the microneedle is configured to prevent the skin augmentation composition from being delivered to the epidermis.

According to some embodiments, the microneedle's base is attached to the substrate. According to some embodiments, the microneedle's base is attached to the substrate's surface intended for being placed proximal to the skin of a subject. According to some embodiments, the microneedle's base is integrally formed with the substrate. According to some embodiments, the microneedle's base is integrally formed with the substrate's surface intended for being placed proximal to the skin of a subject. According to some embodiments, the microneedle's base and the substrate are made of a unitary piece of material. According to some embodiments, the microneedle's base and the substrate's surface intended for being placed proximal to the skin of a subject are made of a unitary piece of material.

According to some embodiments, the length of the base is equal or higher than the thickness of the epidermis at a treated area. Each possibility represents a separate embodiment of the present invention. According to some embodiments, a base having a length equal or higher than the thickness of the epidermis at the treated area prevents delivery of the skin augmentation composition to the epidermis. Preventing delivery of a skin augmentation composition to the epidermis may prevent wasting material, enhance the augmentation effect of the composition or prevent inflammation and/or infection of the treated site. Each possibility represents a separate embodiment of the present invention.

According to certain embodiments, the length of the base is equal or higher than the combined thickness of the epidermis and dermis of the treated area. According to some embodiments, microneedles having a base at least as long as the combined thickness of the epidermis and dermis of the treated area are configured to prevent delivery of the skin augmentation composition to the dermis and the epidermis. According to some embodiments, microneedles having a base at least as long as the combined thickness of the epidermis and dermis of the treated area are configured to deliver the skin augmentation composition subcutaneously. Without wishing to be bound by mechanism, varying the length of the base may determine the skin and/or subcutaneous layer into which the composition is delivered.

According to some embodiments, all the microneedles on the same applicator have the same base length. According to some embodiments, the applicator of the invention comprises microneedles having variable base lengths. According to some embodiments, the length of the base is variable in correlation to the location in which each microneedle is configured to be situated at within a treated area. According to some embodiments, the applicator of the invention comprises microneedles having variable base lengths in correlation to the location of the microneedles on the substrate. According to some embodiments, the applicator of the invention comprises microneedles having variable base lengths in correlation to the thickness of the epidermis and/or dermis at the location each microneedle is configured to be positioned at. Each possibility represents a separate embodiment of the present invention. According to some embodiments, the applicator of the invention comprises microneedles having variable lengths in correlation to the location in which they are configured to be situated within the area to be treated.

According to some embodiments, microneedles configured to be placed at a treatment area having a thick epidermis have a longer base than microneedles configured to be placed at a treatment area having a thin epidermis. It is to be noted that, according to some embodiments, an applicator configured to be placed on a treated area having an epidermis and/or dermis with varying thickness levels may comprise microneedles having bases of varying lengths corresponding to the varying thickness levels. Each possibility represents a separate embodiment of the present invention.

According to some embodiments, microneedles located at the center of a microneedle array comprise a longer base than microneedles located near the edges of the microneedle array. According to some embodiments, microneedles configured to be situated closer to the margins of a line, wrinkle or fold to be treated are comprise a shorter base than microneedles configured to be situated in the center of the line, wrinkle or fold to be treated. According to some embodiments, a microneedle having a long base is configured to deliver the skin augmentation composition to a deeper skin or subcutaneous layer than a microneedle having a short base. Each possibility represents a separate embodiment of the present invention.

According to some embodiments, a diameter of the base is smaller than a diameter of the sharp tip section. According to some embodiments, the largest diameter of the base is smaller than the largest diameter of the sharp tip section. According to some embodiments, the diameter of the base is equal to the diameter of the skin augmentation composition. According to some embodiments, the diameter of the base is equal to the diameter of the microneedle's middle part. As used herein, the diameter of the base refers to the largest distance that can be formed between two opposite parallel lines tangent to the boundary of a cross section through the base of the microneedle, wherein the cross section is parallel to the substrate.

According to some embodiments, the middle section of the microneedle's skeleton is the part of the skeleton connecting between the sharp tip section and the base of the skeleton. According to some embodiments, the skin augmentation composition at least partly surrounds the middle section of the microneedle's skeleton. According to some embodiments, the middle part of the microneedle is the part of the microneedle comprised in between the sharp tip section of the microneedle's skeleton and the base of the microneedle's skeleton. According to some embodiments, the middle part of the microneedle comprises the middle section of the microneedle's skeleton and the augmentation composition According to some embodiments, the middle section of the microneedle skeleton may be in any form suitable for providing the microneedle with rigidity and providing support for the skin augmentation composition. According to some embodiment, the middle section of the skeleton is in the form of a longitudinal core extending substantially from the center of the sharp tip section to the center of the base. According to some embodiment, the middle section of the skeleton comprises a longitudinal core extending substantially from the center of the sharp tip section to the center of the base. As used herein, the term "longitudinal core" refers to a longitudinal piece of a rigid, non-biodegradable, compatible material extending substantially through the center of the microneedle middle part. According to some embodiments, the longitudinal core may be of any shape, such as, but not limited to, a cone, a cylinder, a pyramid, a rectangular box, a triangular box, a polygonal box and the like. According to some embodiments, the longitudinal core has the same dimensions throughout the length of the microneedle's middle part. According to some embodiments, the skeleton's middle section is integrally formed with the sharp tip section. According to some embodiment, the skeleton's middle section is integrally formed with the leakage stopper. According to some embodiments, the skeleton's middle section extends through the base part and is at least partly inserted into the substrate. According to some embodiments, the skeleton's middle section extends through the base part and is at least partly inserted into the substrate perpendicularly. Without wishing to be bound by any mechanism, a skeleton's middle section in the form of a longitudinal core inserted through the base of the skeleton and into the substrate in the form of a cross confers substantial stability to the microneedle. According to some embodiments, the middle section of the skeleton is integrally formed with the microneedle skeleton's base. As used herein, the term "extension", "skeleton extension", "middle section extension", "middle part extension" and "microneedle extension" are used interchangeably and relate to an extension of the middle part of the microneedle's skeleton through the base of the skeleton and at least partly into the substrate of the applicator.

According to some embodiments, the skin augmentation composition at least partly surrounds the middle part of the microneedle's skeleton. According to some embodiments, the skin augmentation composition at least partly surrounds the longitudinal core. According to some embodiments, the skin augmentation composition surrounds the longitudinal core. According to some embodiments, the skin augmentation composition surrounding the skeleton's middle section may form any shape, such as, but not limited to: a cylinder, a rectangular box, a triangular box, a polygonal box and the like.

As used herein, the diameter of the skin augmentation composition refers to the largest distance that can be formed between two opposite parallel lines tangent to the boundary of a cross section through the middle part of the microneedle, wherein the cross section is parallel to the substrate. According to some embodiments, the diameter of the skin augmentation composition refers to the largest distance that can be formed between two opposite parallel lines tangent to the boundary of a cross section through the skin augmentation composition. According to some embodiments, the diameter of the skin augmentation composition refers to the largest distance that can be formed between two opposite parallel lines tangent to the boundary of a cross section through the skin augmentation composition and middle section of the microneedle's skeleton.

According to some embodiments, the microneedle's skeleton further comprises a leakage stopper. According to some embodiments, the leakage stopper is situated between the sharp tip section and the middle section of the microneedle's skeleton. According to some embodiments, the leakage stopper is integrally formed with the sharp tip section and/or the middle section of the skeleton. Each possibility represents a separate embodiment of the present invention. According to some embodiments, the leakage stopper is integrally formed with the sharp tip section. According to some embodiments, the leakage stopper is attached to the sharp tip section.

According to some embodiments, the leakage stopper is configured to prevent leakage of the skin augmentation composition from the skin of the subject following extraction of the microneedle from the skin of the subject. According to some embodiments, the leakage stopper facilitates sliding of the augmentation composition into the treated tissue upon extraction of the microneedles from the skin of the subject. According to some embodiments, the leakage stopper prevents pushing the augmentation composition out of the skin of the subject upon extraction of the microneedles from the skin of the subject. According to some embodiments, the skin augmentation composition at least partly surrounds the leakage stopper. According to some embodiments, the skin augmentation composition at least partly surrounds the middle section of the composition and at least partly surrounds the leakage stopper.

According to some embodiment, the leakage stopper is in a shape selected from the group consisting of: a cone, a pyramid, a triangular pyramid and a polygonal pyramid. Each possibility represents a separate embodiment of the present invention. According to some embodiments, the leakage stopper is in a shape selected from the group consisting of: a cone, a pyramid, a triangular pyramid and a polygonal pyramid: wherein the base of the cone, pyramid, triangular pyramid or polygonal pyramid is attached or integrally formed with the sharp tip section of the microneedle's skeleton. Each possibility represents a separate embodiment of the present invention. According to some embodiments, the skin augmentation composition slides against the leakage stopper and into the treated area concomitantly with extraction of the microneedles from the skin of the subject. In a non-limiting example, the leakage stopper is in the form of a cone, wherein the augmentation composition slides against the cone and into the treated skin upon extraction of the microneedles from the skin. According to some embodiments, extraction of the microneedles from the skin results from pulling the applicator away from the skin of the subject.

Figure 1B:
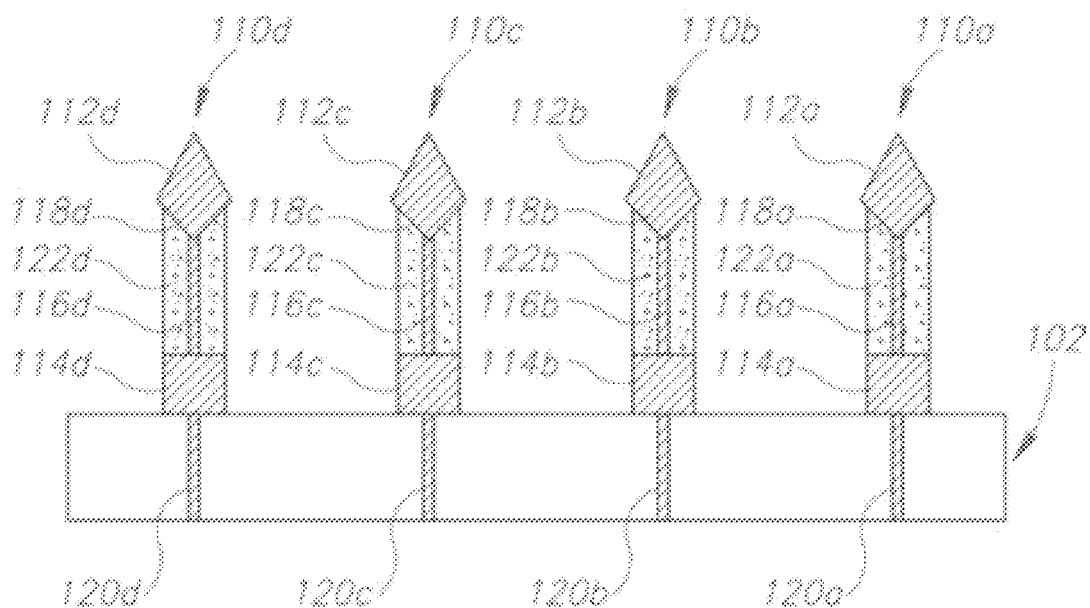
FIG. 1B shows a cross section along line A-A of the applicator of FIG. 1A, according to some embodiments of the invention.

FIG. 1B shows a cross section along line A-A of applicator 100 of FIG. 1A, according to some embodiments of the invention. Substrate 102 of applicator 100 comprises microneedles 110a. 110b, 110c and 110d. According to some embodiments, microneedles 110a, 110b, 110c and 110d are configured to deliver a composition according to embodiments of the invention to undesired lines, wrinkles, depressed scars or folds of a subject's face. According to the embodiment depicted in FIG. 1B, microneedles 110a, 110b. 110c and 110d on substrate 102 have substantially the same length. According to other embodiments, microneedles 110a and 110d, situated near the margins of substrate 102, may have the same length while microneedles 110b and 110c, situated at the center of substrate 102 may have the same length and be longer than microneedles 110a and 110d. Microneedle 110a includes a skeleton comprising three sections: a sharp tip section 112a configured to penetrate the skin of a subject, a base 114a located on the opposing end of the skeleton, and a middle section 116a connecting base 114a and sharp tip section 112a. Base 114a, sharp tip section 112a and middle section 116a are attached to each other and/or are integrally formed with each other. Each possibility represents a separate embodiment of the present invention. Bases 114a, 114b, 114c and 114d of microneedles 110a, 110b, 110c and 110d are in the form of a cylinder but may have other shapes, such as, but not limited to a rectangular box, a cuboid, a triangular box, a polygonal box and the like. Base 114a is attached to or integrally formed with substrate 102a. Each possibility represents a separate embodiment of the present invention. The skeleton of microneedle 110a further comprises leakage stopper 118a in the form of a cone, situated in between sharp tip section 112a and middle section 116a.

It is to be noted that leakage stoppers 118a, 118b, 118c and 118d of microneedles 110a, 110b, 110c and 110d are not limited to the form of a cone and may have forms such as, but not limited to, a cone, a pyramid, a triangular pyramid, a polygonal pyramid and the like. Leakage stopper 118a is integrally formed with sharp tip section 112a such that the base of the cone forming leakage stopper 118a is integrally formed with the base of the cone forming sharp tip section 112a. Middle section 116a is in the form of a longitudinal core extending substantially from the center of sharp tip section 112a to the center of base 114a. Microneedle 110a further comprises skin augmentation composition 122a surrounding middle section 116a. Skin augmentation composition 122a together with middle section 116a constitutes the middle part of microneedle 110a. Leakage stopper 118a is configured to prevent leakage of skin augmentation composition 122a following extraction of microneedle 110a from the skin of a subject.

It is to be understood that bases 114b, 114c, 114d, sharp tip sections 112b, 112c, 112d, middle sections 116b, 116c, 116d, leakage stoppers 118b. 118c, 118d and augmentation compositions 122b, 122c, 122d of microneedles 110b, 110c, 110d, respectively, and substrate 102 relate to each other essentially as described for the corresponding elements of microneedle 110a.

Middle section 116a sends extension 120a through base 114a and into substrate 102. Middle part 116a and extension 120a are perpendicular to base 114a and substrate 102. According to some embodiments, the perpendicular insertion of middle section 116a and extension 120a into base 114a and substrate 102, respectively, confers stability to microneedle 110a. According to the embodiment depicted in FIG. 1B, extension 120d of microneedle 110d is thicker than extensions 120b and 120c of microneedles 110b and 110c which are in turn thicker than extension 120a of microneedle 110a. According to some embodiments, different microneedles within the same applicator comprise extensions having different thickness levels. According to some embodiments, a microneedle comprising a thick extension is more stable than a microneedle than a thin extension. As used herein, a stable microneedle refers to a microneedle firmly attached to and/or integrally formed with the substrate.

Figure 2B:
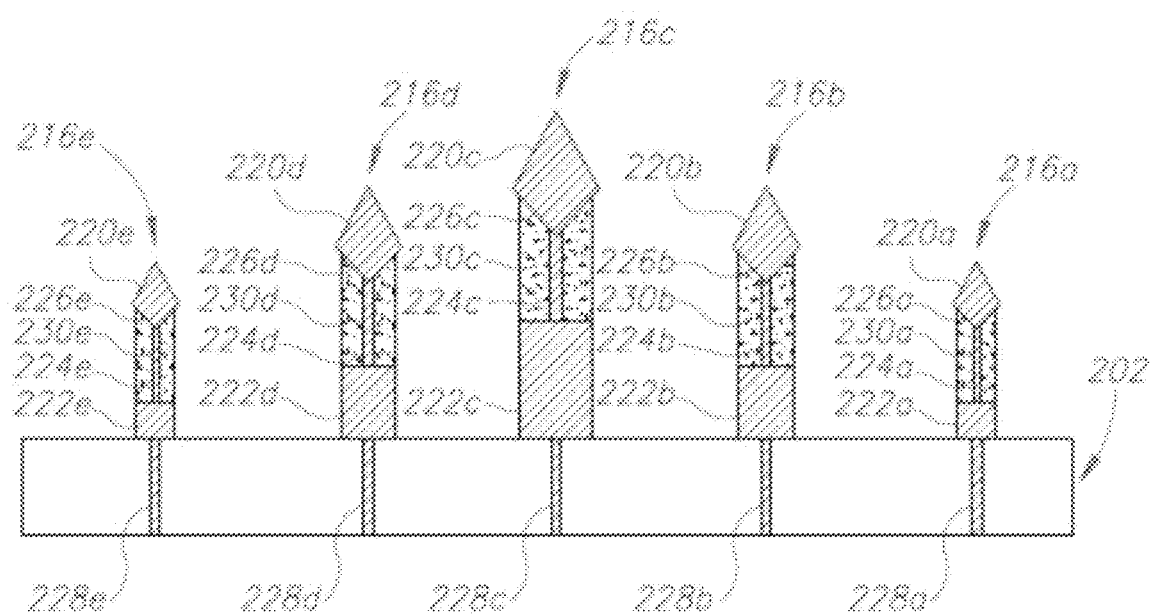
FIG. 2B shows a cross section along line B-B of the applicator of FIG. 2B, according to some embodiments of the invention.

FIG. 2B shows a cross section along line B-B of applicator 200 of FIG. 2A, according to some embodiments of the invention. Substrate 202 comprises microneedles 216a, 216b, 216c, 216d, 216e. According to some embodiments, microneedles 216a, 216b, 216c, 216d, 216e are configured to deliver skin augmentation composition 230a. 230b, 230c. 230d, 230e to undesired lines, wrinkles, depressed scars or folds of a subject's face. According to some embodiments, microneedles 216a and 216e are shorter than microneedles 216b and 216d which are in turn shorter than microneedle 216c. According to some embodiments, microneedles 216a and 216e are configured to deliver augmentation composition 230a and 230e to the ends and/or margins of a wrinkle, line or the like to be treated, microneedle 216c is configured to deliver augmentation composition 230c to the center/deep region of the a wrinkle, line or the like to be treated. Each possibility represents a separate embodiment of the present invention. According to some embodiments, applicators configured to be applied to areas having thinner skin (such as, but not limited to, near the eyes comprise shorter microneedles than applicators configured to be applied to areas having thicker skin (such as, but not limited to, nasolabial folds.

According to some embodiments, microneedle 216a includes a skeleton comprising three sections: a sharp tip section 220a configured to penetrate the skin of a subject, a base 222a located on the opposing end of the skeleton, and a middle section 224a connecting base 222a and sharp tip section 220a. Base 222a, sharp tip section 220a and middle section 224a are attached to each other and/or are integrally formed with each other. Each possibility represents a separate embodiment of the present invention. Bases 222a, 222b, 222c, 222d, 222e of microneedles 216a, 216b, 216c, 216d, 216e are in the form of a cylinder but may have other shapes, such as, but not limited to a rectangular box, a cuboid, a triangular box, a polygonal box and the like. Base 222a is attached to or integrally formed with substrate 202. Each possibility represents a separate embodiment of the present invention. The skeleton of each one of microneedles 216a further comprises leakage stopper 226a in the form of a cone, situated in between sharp tip section 220a and middle section 224a. It is to be noted that leakage stoppers 226a. 226b, 226c, 226d, 226d of microneedles 216a, 216b, 216c, 216d, 216e are not limited to the form of a cone and may have forms such as, but not limited to, a cone, a pyramid, a triangular pyramid, a polygonal pyramid and the like. Leakage stopper 226a is integrally formed with sharp tip section 220a such that the base of the cone forming leakage stopper 226a is integrally formed with the base of the cone forming sharp tip section 220a. Middle section 224a is in the form of a longitudinal core extending substantially from the center of sharp tip section 220a to the center of base 222a. Microneedles 216a further comprises skin augmentation composition 230a surrounding middle section 224a. Skin augmentation composition 230a together with middle section 224a constitutes the middle part of microneedle 216a. Leakage stopper 226a is configured to prevent leakage of skin augmentation composition 230a following extraction of microneedles 216a from the skin of a subject. Middle section 224a sends extension 228a through base 222a and into substrate 202. Middle part 224a and extension 228a are perpendicular to base 222a and substrate 202. According to some embodiments, the perpendicular insertion of middle section 224a and extension 228a into base 222a and substrate 202, respectively, confers stability to microneedle 216a.

It is to be understood that bases 222b, 222c, 222d, 222e, sharp tip sections 220b, 220c, 220d, 220e, middle sections 224b, 224c, 224d, 224e, leakage stoppers 226b, 226c, 226d, 226e, extensions 228b, 228c, 228d, 228e and augmentation compositions 230b, 230c, 230d, 230e of microneedles 216b, 216c, 216d, 216e, respectively, and substrate 202 relate to each other essentially as described for the corresponding elements of microneedle 216a.

Base 222c of microneedle 216c is longer than bases 222b and 222d of microneedles 216b and 216d, which are in turn longer than bases 222a and 222e of microneedles 216a and 216e. According to some embodiments, the applicator comprises microneedles having bases of various lengths. According to some embodiments, long microneedle bases, such as base 222c of microneedle 216c, ensure delivery of augmentation composition such as 230c to deep skin layers or subcutaneously without delivery to shallower layers of the skin. Each possibility represents a separate embodiment of the present invention.

Figure 4A:
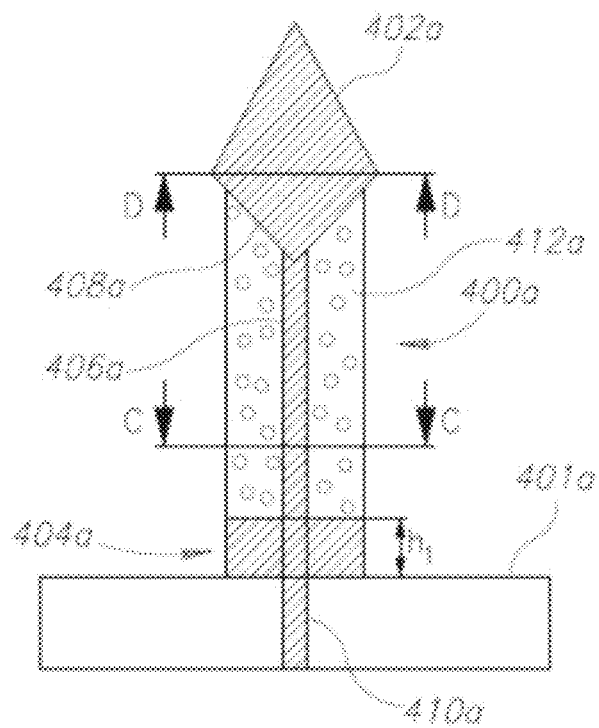
FIGS. 4A, 4B and 4C schematically show microneedles, according to some embodiments of the invention.

FIG. 4A schematically shows microneedle 400a on substrate 401a, according to some embodiments of the invention. According to some embodiments, microneedle 400a includes a skeleton comprising three sections: a sharp tip section 402a configured to penetrate the skin of a subject located at the proximal-most end of the skeleton, a base 404a located on the opposing end of the skeleton, and a middle section 406a connecting base 404a and sharp tip section 402a. Base 404a, sharp tip section 402a and middle section 406a are attached to each other and/or are integrally formed with each other. Each possibility represents a separate embodiment of the present invention. Base 404a is in the form of a cylinder but may have other shapes, such as, but not limited to a rectangular box, a cuboid, a triangular box, a polygonal box and the like. Base 404a is attached to or integrally formed with substrate 401a. Each possibility represents a separate embodiment of the present invention. The skeleton of microneedle 400a further comprises leakage stopper 408a in the form of a cone, situated in between sharp tip section 402a and middle section 406a. Leakage stopper 408 is in the form of a cone but may have different forms such as, but not limited to a pyramid, triangular pyramid and the like.

Sharp tip section 402a is in the form of a cone, but may have a different form, such as, but not limited to a pyramid, a triangular pyramid or a polygonal pyramid. Leakage stopper 408a is integrally formed with sharp tip section 402a such that the base of the cone forming leakage stopper 408a is integrally formed with the base of the cone forming sharp tip section 402a. Middle section 406a is in the form of a longitudinal core extending substantially from the center of sharp tip section 402a to the center of base 404a. Middle section 406a sends extension 410a through base 404a and into substrate 401a. Middle part 116a and extension 410a are perpendicular to base 404a and substrate 401a. According to some embodiments, the perpendicular insertion of middle section 406a and extension 410a into base 404a and substrate 401a, respectively, confers stability to microneedle 400a. Microneedle 400a further comprises skin augmentation composition 412a surrounding middle section 406a. The skin augmentation composition 412a together with middle section 406a constitutes the middle part of microneedle 400a. Leakage stopper 408a is configured to prevent leakage of skin augmentation composition 412a following extraction of microneedle 400a from the skin of a subject. According to some embodiments, skin augmentation composition 412a comprises hydroxyapatite beads of about 40 µm and polyethylene glycol having a molecular weight of 20-50 kDa.

Figure 4B:
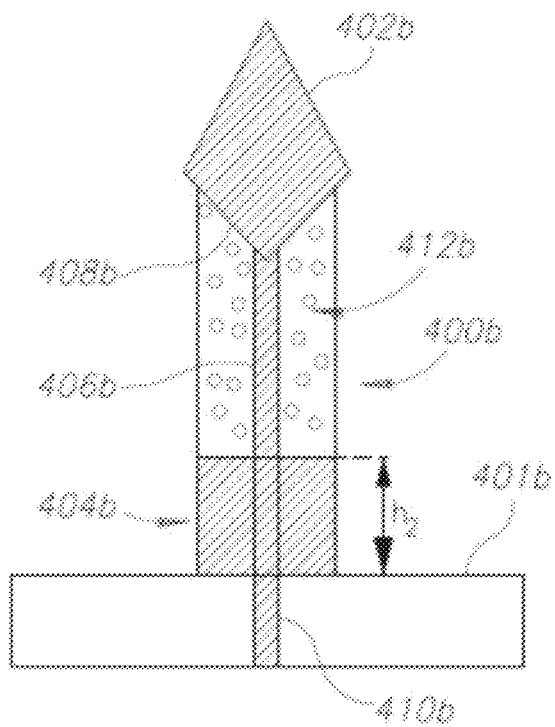
Figure 4C:
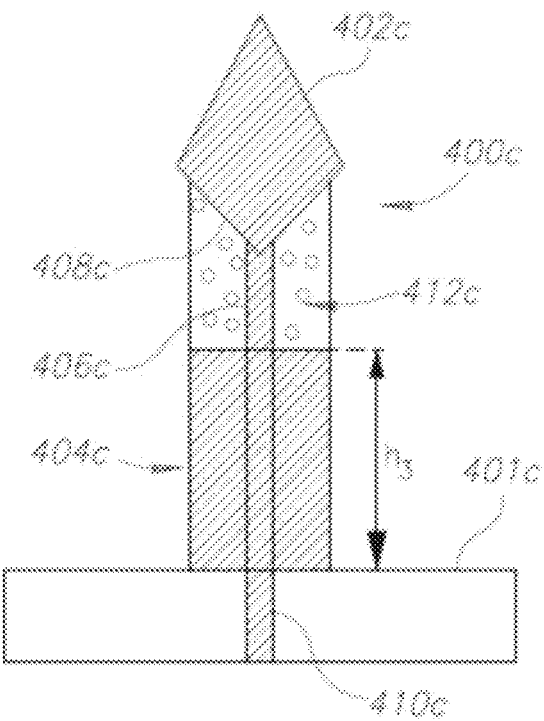
Figure 4E:
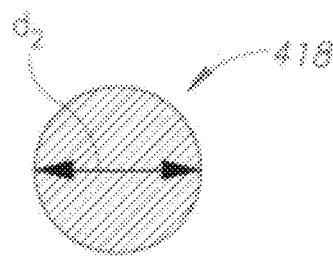
FIG. 4E shows a cross section along line D-D of the applicator of FIG. 4A, according to some embodiments of the invention.
Figure 4D:
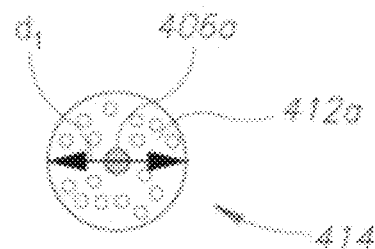
FIG. 4D shows a cross section along line C-C of the applicator of FIG. 4A, according to some embodiments of the invention.

FIG. 4D shows cross section 414 along line C-C of the middle part of microneedle 400a. Cross section 414 shows middle part 406a of the microneedle's skeleton and skin augmentation composition 412a. Line (d1) represents the diameter of cross section 414. It is to be noted that line (d1) represents the diameter of the middle part of microneedle 400a at its widest part. FIG. 4E shows cross section 418 along line D-D of the sharp tip section 402a. Line (d2) represents the diameter of cross section 418. It is to be noted that line (d2) represents the diameter of sharp tip section 402a at its widest part. As can be seen in FIG. 4D and FIG. 4E, according to the embodiment depicted in FIG. 4A, diameter (d2) of sharp tip section 402 is larger than diameter (d1) of the middle part of microneedle 400. According to some embodiments, a microneedle having a sharp tip section with a larger diameter than the diameter of the microneedle's middle part enables insertion of the microneedle into the skin of a subject without spillage of the skin augmentation composition outside the body. According to some embodiments, a microneedle having a sharp tip section with the same diameter (or cross section area) as the diameter (or cross section area) of the microneedle's middle part enables insertion of the microneedle into the skin of a subject without spillage of the skin augmentation composition outside the body.

FIG. 4B and FIG. 4C depict microneedles 400b and 400c, respectively, according to some embodiments of the invention. Sharp tip sections 402b, 402c, middle sections 406b, 406c, leakage stoppers 408b, 408c, extensions 410b, 410c and augmentation compositions 412b, 412c of microneedles 400b, 400c, respectively, and substrates 401b, 401c relate to each other essentially as described for the corresponding elements of microneedle 400a. Microneedles 400b and 400c are of the same length of microneedle 400a depicted in FIG. 4A.

Base 404b of microneedle 400b and base 404c of microneedle 400c have lengths h2 and h3, respectively, which are higher than length h of base 404a depicted in FIG. 4A as part of microneedle 400a. Length h3 of Base 404c is higher than length h2 of base 404b. According to some embodiments, a longer skeleton base is configured to prevent delivery of skin augmentation composition to shallow skin layers, such as, but not limited to, the epidermis. According to some embodiments, different skin areas require different lengths of microneedle bases due to differences in thickness of skin layers, such as, but not limited to, the epidermis. In a non-limiting example, microneedle 400c may be used to treat a skin area having a thick epidermal layer, while microneedles 400a or 400b may be used to treat a skin area having a thinner epidermal layer.

Figure 5A:
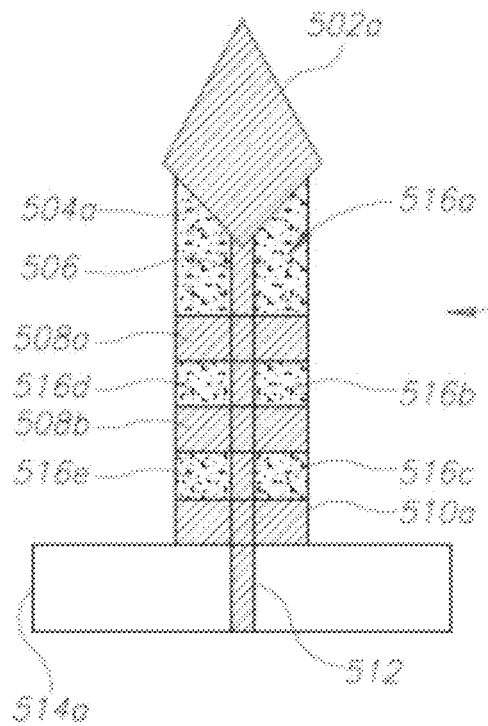
FIGS. 5A, 5B, 5B' and 5C schematically show microneedles, according to some embodiments of the invention.
Figure 5B:
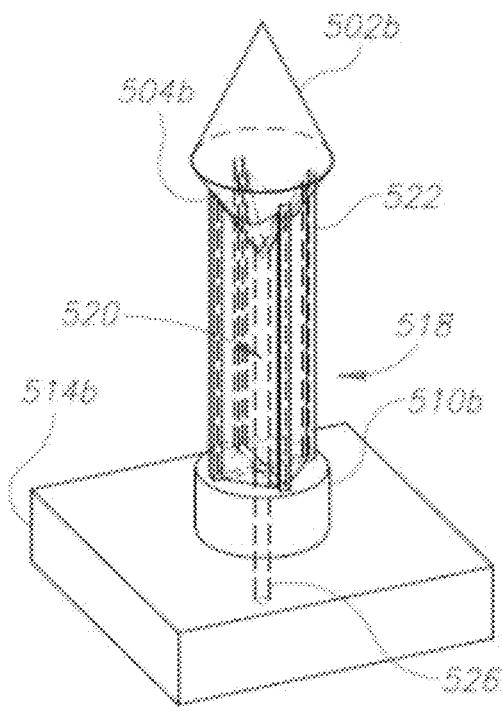
Figure 5B:
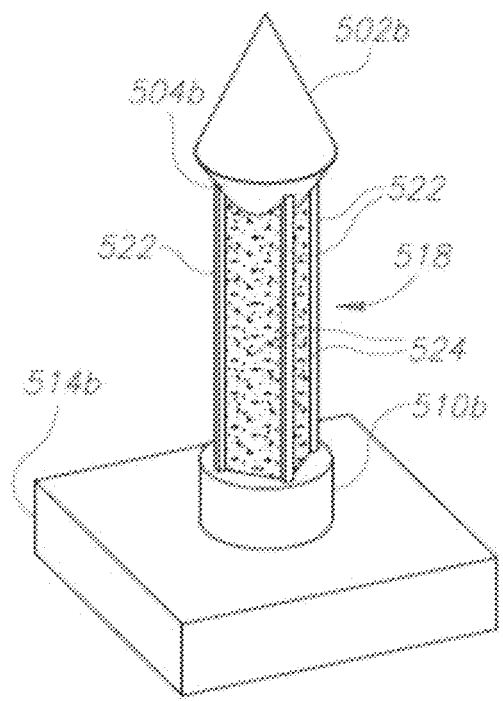
Figure 5C:
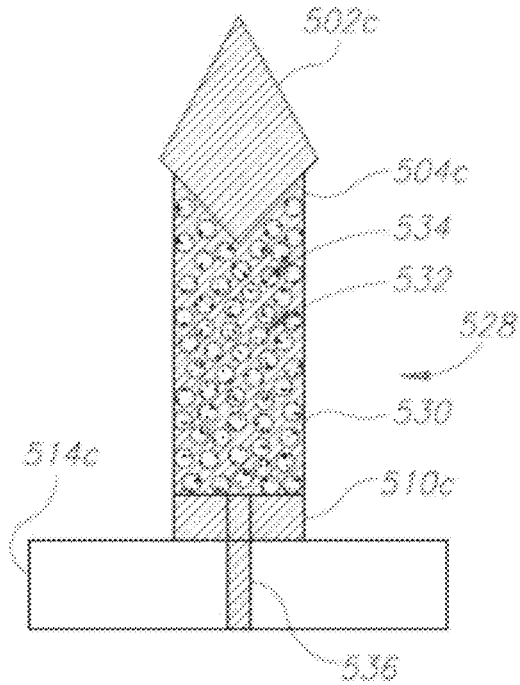

FIGS. 5A-5C show different microneedles, according to various embodiments of the present invention. FIG. 5A shows microneedle 500 on substrate 514a, according to some embodiments of the invention. Microneedle 500 comprises a skeleton composed of: sharp tip section 502a integrally formed with leakage stopper 504a, base 510a and a middle section composed of longitudinal core 506 and discs 508a. 508b around longitudinal core 506. Longitudinal core 506 is attached to or integrally formed with leakage stopper 504a. Each possibility represents a separate embodiment of the present invention. Microneedle 500 further comprises skin augmentation composition 516a, 516b, 516c. 516d, 516e surrounding longitudinal core 506, in between discs 508a, 508b and between disc 508b and base 510a. Longitudinal core 506 sends extension 512 through base 510a and into substrate 514a. Longitudinal core 506 is attached to or integrally formed with base 510a.

It is to be understood that substrates 514b, 514c, as well as sharp tip sections 502b. 502c, leakage stoppers 504b. 504c and bases 510b. 510c of microneedles 518 and 528, as depicted in FIGS. 5B, 5B' and 5C, are essentially identical to corresponding elements 514a, 502a, 504a, 510a of FIG. 5A.

FIG. 5B shows another embodiment of a microneedle according to the present invention. FIG. 5B' shows an internal view of the microneedle of FIG. 5B. The skeleton's middle section of microneedle 518, as shown in FIGS. 5B and 5B', comprises a narrow longitudinal core 520 and several longitudinal flaps 522 extending outwards from longitudinal core 520. Longitudinal flaps 522 are attached to or integrally formed with leakage stopper 504b. Each possibility represents a separate embodiment of the present invention. Longitudinal flaps 522 are attached to or integrally formed with base 510b. Each possibility represents a separate embodiment of the present invention. According to the embodiment depicted in FIG. 5B, skin augmentation composition 524 is situated in between longitudinal flaps 522. As depicted in FIG. 5B', narrow longitudinal core 520 sends narrow extension 526 through base 510b and into substrate 514b.

The skeleton's middle section of microneedle 528, as shown in FIG. 5C, is composed of a rigid material 530 having a plurality of cavities 532. According to the embodiment depicted in FIG. 5C, skin augmentation composition 534 is situated at least partly within cavities 532. According to some embodiments, rigid material 530 is attached to or integrally formed with base 510c. Each possibility represents a separate embodiment of the present invention. According to some embodiments, rigid material 530 is attached to or integrally formed with leakage stopper 504c. Each possibility represents a separate embodiment of the present invention. Rigid material 530 sends extension 536 through base 510c and into substrate 514c.

Figure 6B:
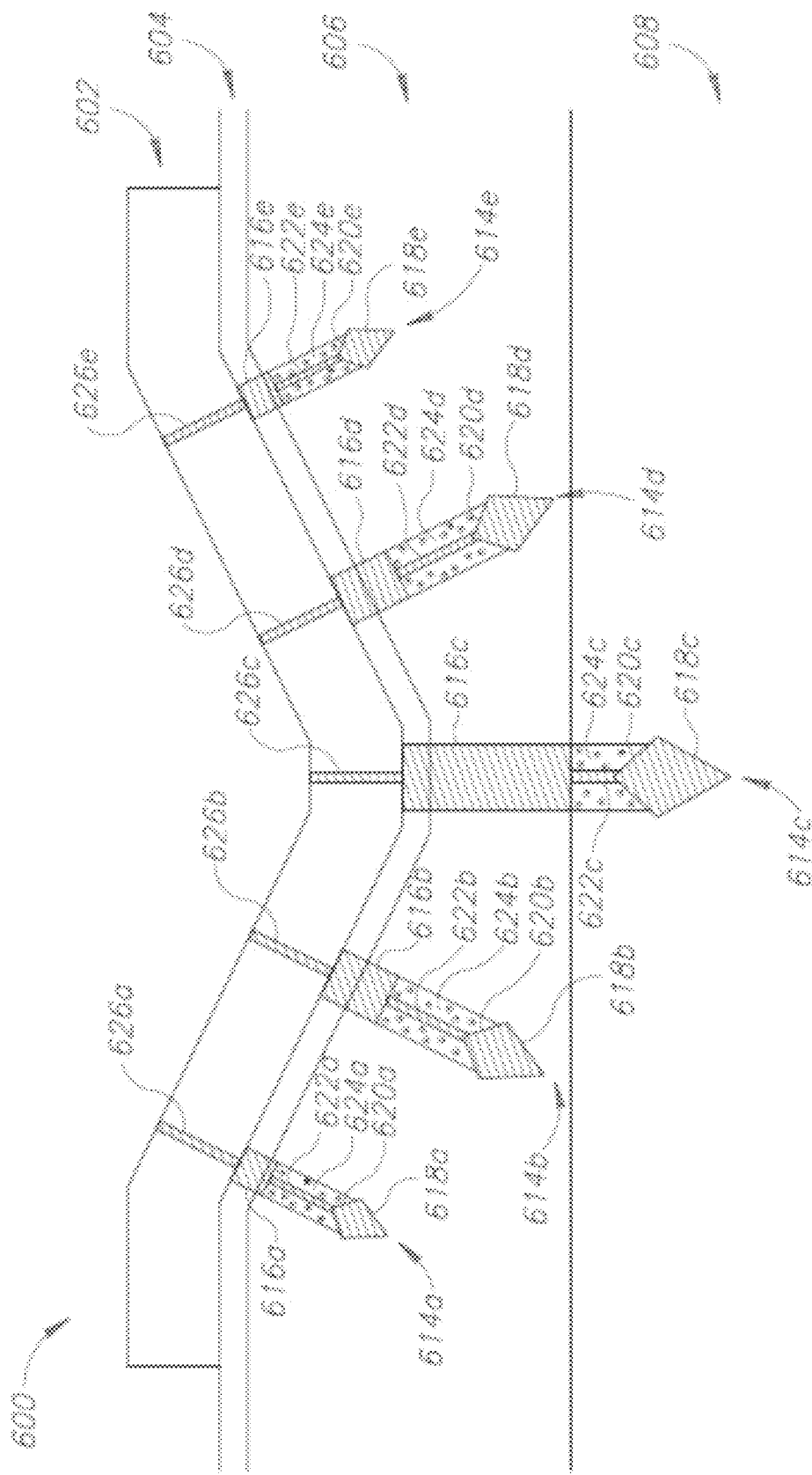

FIGS. 6A-D show treatment of a deep skin line or deficiency using the applicator of the invention, according to several embodiments. As depicted in FIG. 6A, applicator 600 is positioned over and moved towards skin deficiency 610. Skin deficiency 610 may be a deficiency in skin, sub-cutaneous layers or a combination thereof. Applicator 600 comprises substrate 602 and microneedles 614a, 614b. 614c. 614d, 614e. Microneedles 614a and 614e are of the same length and are shorter than microneedles 614b and 614d, which have the same length and are in turn shorter than microneedle 614c. Applicator 600 is positioned over skin deficiency 610 such that longer microneedles 614b, 614c, 614d, located substantially in the center of substrate 602, are positioned over the deepest point 612 of skin deficiency 610. Shorter microneedles 614a and 614e are positioned over the shallower parts of skin deficiency 610. According to some embodiments, long microneedles 614c are configured to deliver skin augmentation composition 624c to deeper skin or sub-cutaneous layers, such as, but not limited to, the hypodermis 608. According to some embodiments, an applicator such as applicator 600 having microneedles 614a, 614b, 614c, 614d, 614e of different lengths is configured for a more uniform augmentation of a deep and/or non-uniformly shaped skin deficiency such as skin deficiency 610. Each possibility represents a separate embodiment of the present invention. According to some embodiments, skin deficiency 610 is a nasolabial fold.

Each one of microneedles 614a, 614b, 614c. 614d. 614e comprises a skeleton comprising three sections: base 616a, 616b, 616c, 616d, 616e, sharp tip section 618a, 618b, 618c. 618d, 618e configured to penetrate the skin of a subject and integrally formed with leakage stopper 620a, 620b, 620c, 620d, 620e, and middle section 622a, 622b, 622c, 622d, 622e connecting base 616a, 616b. 616c, 616d. 616e and leakage stopper 620a, 620b, 620c, 620d, 620e. Each one of middle sections 622a, 622b, 622c, 622d, 622e sends extension 626a, 626b, 626c, 626d, 626e through bases 616a, 616b, 616c, 616d, 616e and into substrate 602. Each one of microneedles 614a, 614b, 614c, 614d, 614e further comprises skin augmentation composition 624a, 624b, 624c, 624d. 624e surrounding middle section 622a, 622b, 622c, 622d. 622e. Leakage stoppers 620a, 620b, 620c, 620d. 620e are configured to prevent leakage of skin augmentation composition 624a, 624b, 624c, 624d, 624e following extraction of microneedles 614a, 614b, 614c, 614d, 614e from the skin of a subject.

Bases 616a and 616e of microneedles 614a and 616e, respectively, are of the same length and are shorter than bases 616b and 616d of microneedles 614b and 616d which have the same length and are in turn shorter than base 616c of microneedle 614c. Base 616c is long and configured to prevent delivery of skin augmentation composition 624c to the epidermis 604 and dermis 606 layer, thus microneedle 614c delivers skin augmentation composition 624c to deep layers, such as, but not limited to, the hypodermis 608. Bases 616a, 616b, 616d, 616e are configured to prevent delivery of skin augmentation composition 624a, 624b, 624d, 624e to the epidermis 604 and superficial layers, thus microneedles 614a, 614b, 614d, 614e deliver skin augmentation composition 624a. 624b, 624d, 624e to sub-epidermal layers, such as, but not limited to, the dermis 606. According to some embodiments, the length of the microneedle's base is directly correlated to the thickness of the epidermis and/or other superficial layers to be penetrated by the microneedle. Each possibility represents a separate embodiment of the present invention. According to some embodiments, the length of the microneedle's base is directly correlated to the depth of the dermal or sub-dermal layer to which the composition of the invention is to be delivered. Each possibility represents a separate embodiment of the present invention. According to some embodiments, a microneedle configured to deliver the composition of the invention to a subdermal layer comprises a longer microneedle base than a microneedle configured to deliver the composition to the dermis. According to some embodiments, the length of the microneedle's base is at least as long as the thickness of the epidermis and/or other layers to be penetrated by the microneedle. According to some embodiments, the microneedle's base is longer than the thickness of the epidermal layer to be penetrated by the microneedle. According to some embodiments, the applicator comprises microneedles having different lengths of microneedle base in correlation to the position of the microneedle on the substrate.

FIG. 6B depicts applicator 600 following application to skin deficiency 610. As can be seen in FIG. 6B, substrate 602 is flexible and, following application, conforms to the contours of skin deficiency 610. Following application, microneedles 614a, 614b, 614c, 614d, 614e penetrate through the epidermis 604. Microneedles 614a, 614b, 614d, 614e penetrate into the dermis 606, while longer microneedle 614c penetrates into lower layer 608, such as, but not limited to, the hypodermis. The length of bases 616a. 616b, 616d, 616e is longer than the thickness of epidermis 604, thus preventing delivery of skin augmentation composition 624a, 624b, 624d, 624e to the epidermis 604. Base 616c is as long as the thickness of epidermis 604 and dermis 606 together, thus preventing delivery of skin augmentation composition 624c to the epidermis 604 and the dermis 606.

Figure 6C:
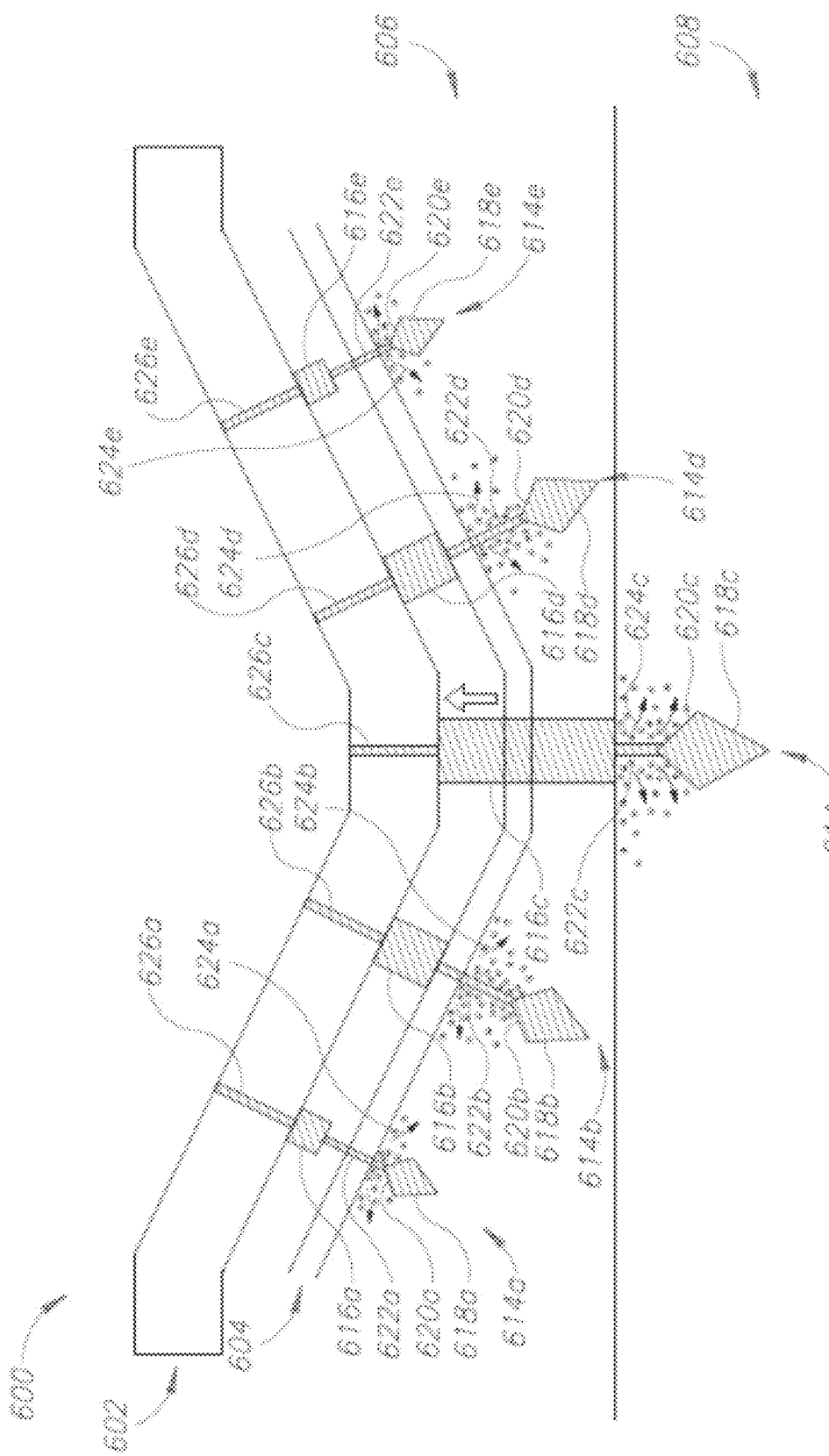

FIG. 6C depicts applicator 600 in the process of being removed from skin deficiency 610 following treatment according to some embodiments of the present invention. As can be seen in FIG. 6C, during extraction of microneedles 614a, 614b, 614c, 614d, 614e from the skin, at least part of skin augmentation composition 624a, 624b, 624c, 624d. 624e slides over leakage stoppers 620a, 620b, 620c, 620d, 620e of microneedles 614a, 614b, 614c, 614d, 614e and into the skin of the subject. According to some embodiments, only the part of skin augmentation composition 624a, 624b, 624c, 624d. 624e that did not undergo biodegradation in the skin of the subject during application slides over leakage stoppers 620a, 620b, 620c. 620d. 620e of microneedles 614a, 614b, 614c, 614d, 614e and into the skin or sub-cutis of the subject.

As can be seen in FIG. 6D, after applicator 600 has been extracted from the skin of the subject, augmentation composition 624a, 624b, 624d. 624e remains within the dermis 606 and augmentation composition 624c remains within the hypodermis 608 such that skin deficiency 610 has been augmented. Following extraction of applicator 600 from the skin of the subject, substrate 602 regains its original shape and comprises only the skeletons of microneedles 614a, 614b, 614c, 614d, 614e.

Figure 7A:
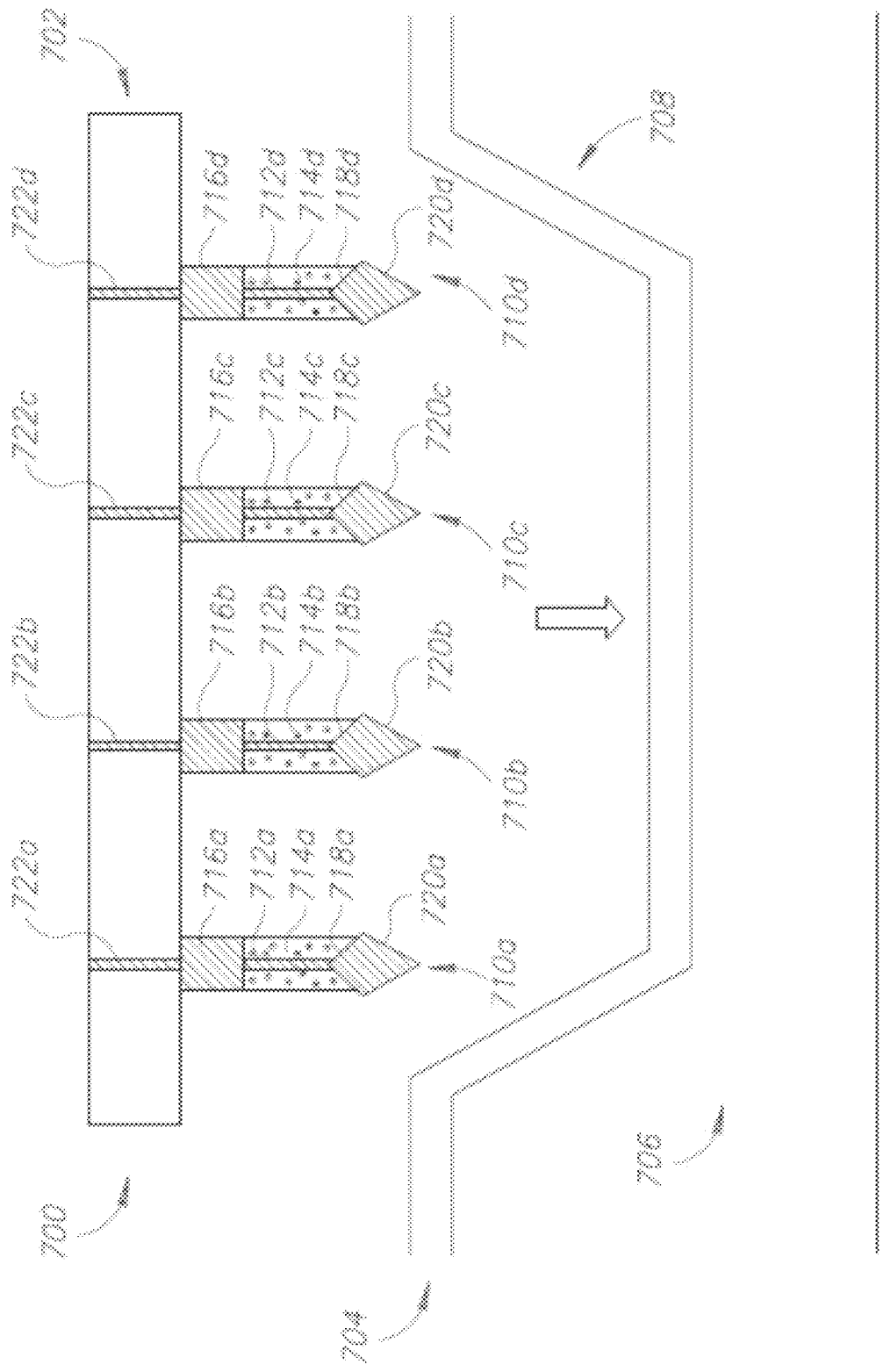

FIGS. 7A-D show treatment of a shallow skin line or deficiency using the applicator of the invention, according to several embodiments. As depicted in FIG. 7A, applicator 700 is positioned over and moved towards skin deficiency 708. Applicator 700 comprises substrate 702 and microneedles 710a, 710b, 710c, 710d. Microneedles 710a. 710b, 710c. 710d of applicator 700 are all of substantially the same length and are configured to deliver augmentation composition 714a, 714b, 714c, 714d to the dermis 706 of the treated subject.

Each one of microneedles 710a, 710b, 710c, 710d comprises a skeleton comprising three sections: base 716a, 716b, 716c, 716d, sharp tip section 720a, 720b, 720c, 720d configured to penetrate the skin of a subject and integrally formed with leakage stopper 718a, 718b, 718c, 718d, and middle section 712a, 712b. 712c, 712d connecting base 716a, 716b. 716c, 716d and leakage stopper 718a, 718b, 718c, 718d. Each one of middle sections 712a, 712b, 712c, 712d sends extension 722a, 722b, 722c, 722d through bases 716a, 716b, 716c, 716d and into substrate 702. Each one of microneedles 710a, 710b, 710c, 710d further comprises skin augmentation composition 714a, 714b, 714c, 714d surrounding middle section 712a, 712b, 712c, 712d. Leakage stoppers 718a, 718b, 718c, 718d are configured to prevent leakage of skin augmentation composition 714a, 714b, 714c, 714d following extraction of microneedles 710a, 710b, 710c, 710d from the skin of a subject.

Figure 7B:
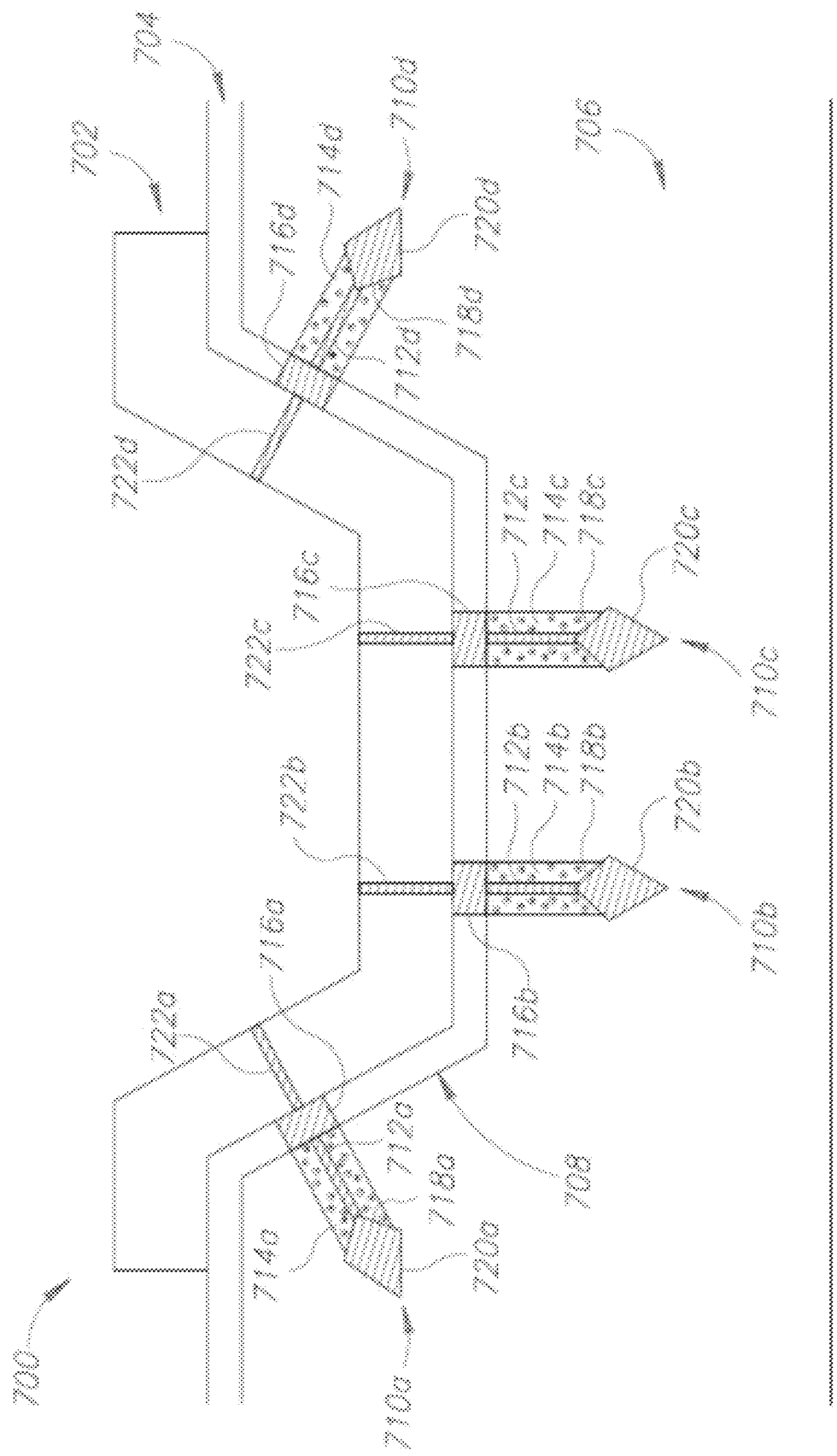

FIG. 7B depicts applicator 700 following application to the skin deficiency 708. As can be seen in FIG. 7B, substrate 702 is flexible and, following application, conforms to the contours of skin deficiency 708. Following application, microneedles 710a, 710b, 710c, 710d penetrate through the epidermis 704 and enter into the dermis 706. According to some embodiments, base 716a, 716b, 716c, 716d of microneedles 710a. 710b, 710c, 710d is as long as the thickness of epidermis 704, thus preventing delivery of augmentation composition 714a, 714b, 714c, 714d to the dermis 704.

Figure 7C:
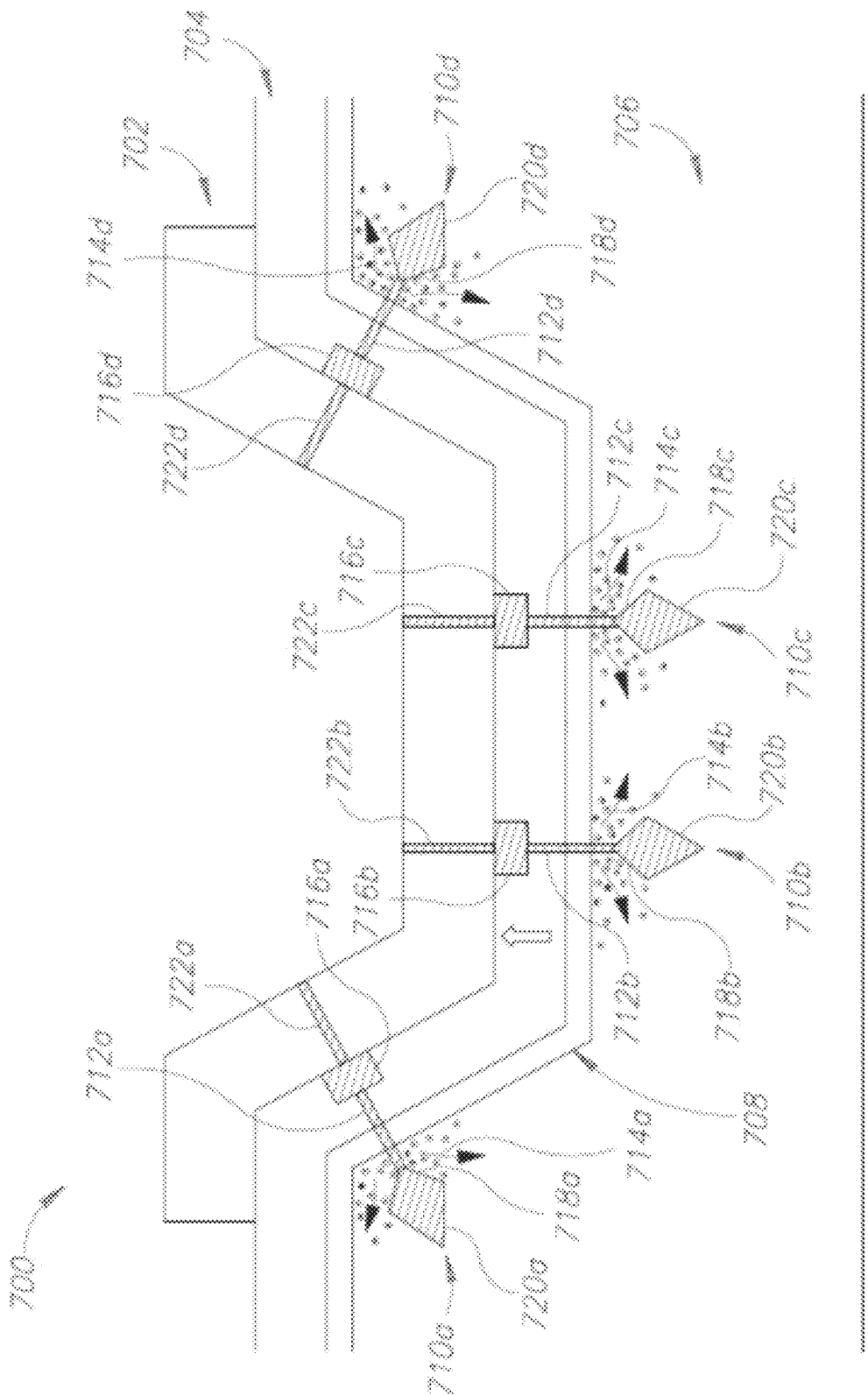

FIG. 7C depicts applicator 700 in the process of being removed from skin deficiency 708 following treatment according to some embodiments of the present invention. As can be seen in FIG. 7C, during extraction of microneedles 710a, 710b, 710c, 710d from the skin, at least part of augmentation composition 714a, 714b, 714c, 714d slides over leakage stopper 718a, 718b, 718c, 718d of microneedles 710a, 710b, 710c, 710d and into the dermis 706.

As can be seen in FIG. 7D, after applicator 700 has been extracted from the skin of the subject, at least part of augmentation composition 714a, 714b, 714c, 714d remains within the dermis 706 such that skin deficiency 708 has been augmented. According to some embodiments, only the biocompatible ceramic material that was present in composition 714a, 714b, 714c, 714d remains within the dermis 706. Following extraction of applicator 700 from the skin of the subject, substrate 702 regains its original shape and comprises only the skeletons of microneedles 710a, 710b. 710c. 710d.

FIGS. 8A-E depict a manufacturing procedure for microneedles, according to some embodiments of the present invention. As shown in FIG. 8A, first half-mold 800 is loaded with a microneedle skeleton 801 comprising sharp tip section 802, leakage stopper 804, middle section 806, base 808 and extension 810. Sharp tip section 802 may be attached to or integrally formed with leakage stopper 804. According to some embodiments, extension 810 is the direct continuation of middle section 806 protruding through base 808. First half-mold 800 is configured to delineate half of the middle part of the final needle to be produced. According to the embodiment depicted in FIG. 8A only base 808 and leakage stopper 804 of microneedle skeleton 801 are in direct contact with first half-mold 800. According to some embodiments, extension 810, sharp tip section 802 and part of leakage stopper 804 protrude from first half-mold 800. According to some embodiments, at least part of base 808 protrudes from first half-mold 800. First half-mold 800 is depicted having a rectangular shape but may have any shape which best suits production of microneedles according to the depicted embodiments. As shown in FIG. 8B, augmentation composition 812 is deposited on microneedle skeleton 801 such that it covers middle section 806 and part of leakage stopper 804. As shown in FIG. 8C, second half-mold 814 is fitted onto first half-mold 800 and microneedle skeleton 801 onto which augmentation composition has been deposited. When fitted around microneedle skeleton 801 onto which augmentation composition had been deposited, first half-mold 800 and second half-mold 814 are configured to delineate the middle part of the microneedle such that the augmentation composition in the resulting microneedle will surround middle section 806 and at least part of leakage stopper 804. First half-mold 800 and second half-mold 814 are configured to shape the middle part of the produced microneedle to a desired shape. According to some embodiments, first half-mold 800 and second half-mold 814 are configured to partly interlock into each other. As seen in FIG. 8D, augmentation composition 812 which defines the middle part of the produced microneedle, is in the shape of a cylinder following removal of second half-mold 814, but may be in other shapes, such as a polygonal box, as provided by first half-mold 800 and second half-mold 814. FIG. 8E depicts the final microneedle as produced according to the embodiments of FIGS. 8A-E. Extension 810 may be inserted into a substrate of an applicator according to the present invention. Extension 810 may be cut to fit a substrate according to the present invention, either before or after being inserted into the substrate.

According to other embodiments not shown, first half-mold 800 is loaded with microneedle skeleton 801 followed by deposition of augmentation composition 812 onto part of middle section 806 and leakage stopper 804 such that only the parts of middle section 806 and leakage stopper 804 that are within first half-mold 800 are filled with augmentation composition 812. Excess augmentation composition 812 may be removed. After augmentation composition 812 that has been deposited within first half-mold 800 has dried, additional augmentation composition may be added on top of the dried augmentation composition followed by fitting of second half-mold 814 onto first half-mold 800. After the augmentation composition has fully dried, first half-mold 800 and second half-mold 814 may be removed, resulting in the final microneedle, as depicted in FIG. 8E.

According to another aspect, the present invention provides a method for manufacturing a microneedle for administration of a skin augmentation composition to a skin and/or sub-cutis of a subject, the method comprises: producing a microneedle skeleton of a rigid material, said skeleton comprising: a sharp tip section located on one end of said skeleton, said sharp tip section being configured to penetrate a skin of a subject; a base on an opposing end of said skeleton; and a middle section connecting between said sharp tip section and said base; and depositing a skin augmentation composition on said skeleton such that said composition at least partly surrounds said middle section and a diameter of said sharp tip section is larger than a diameter of said augmentation composition; wherein said composition comprises at least one biocompatible ceramic material.

According to some embodiments, depositing the skin augmentation composition according to the method for manufacturing of the present invention comprises preventing deposition of the skin augmentation composition around the base and sharp tip section.

According to some embodiments, the method for manufacturing of the present invention further comprises placing the microneedle skeleton in a mold prior to depositing the skin augmentation composition, wherein the mold is configured to shape the skin augmentation composition around at least part of the middle section. According to some embodiments, the mold is further configured to prevent deposition of the skin augmentation composition around the base and sharp tip section.

According to some embodiments, the present invention provides a method of manufacturing the microneedles of the invention, the method comprises depositing a skin augmentation composition around at least part of the middle section of the microneedle such that the sharp tip section and the base of the microneedle remain devoid of skin augmentation composition. According to some embodiments, the method of manufacturing further comprises depositing the skin augmentation composition around at least part of a leakage stopper.

According to some embodiments, the method of manufacturing comprises loading a microneedle skeleton on a mold such that the mold is configured to shape the skin augmentation composition around at least part of the middle section, and wherein the mold is configured not to deposit the skin augmentation composition around the base and sharp tip section of the microneedle. According to some embodiments, the mold is configured to shape the skin augmentation composition around at least part of the middle section and at least part of the leakage stopper. According to some embodiments, the mold is composed of a plurality of parts, such as, but not limited to a first and a second half molds.

According to another aspect, the present invention provides a method for delivering a skin augmentation composition to a site of skin defect or deficiency, comprising placing at the site an applicator configured for administration of a skin augmentation composition to a skin of a subject, the applicator comprising a substrate and an array of microneedles; wherein the substrate has a generally flattened structure having two opposing surfaces, wherein one surface is intended for being placed proximal to the skin of a subject and the other surface facing away from the skin of the subject; wherein the array of microneedles is located on the surface proximal to the skin of the subject, the array comprising a multiplicity of microneedles, wherein each of the microneedles comprises:
  a skeleton made of a rigid material, the skeleton comprises:
    a sharp tip section located on one end of the skeleton, the sharp tip section being configured to penetrate a skin of a subject;
    a base on an opposing end of the skeleton; and
    a middle section connecting between the sharp tip section and the base; and
  a skin augmentation composition comprising at least one biocompatible ceramic material, wherein the augmentation composition at least partly surrounds the middle section, such that a diameter of the sharp tip section is larger than a diameter of the augmentation composition.

According to another aspect, the present invention provides a method for filling an undesired fold, wrinkle, line or depressed area in a subject, comprising placing at the site of the fold, wrinkle, line or depressed area an applicator configured for administration of a skin augmentation composition to a skin of a subject, the applicator comprising a substrate and an array of microneedles; wherein the substrate has a generally flattened structure having two opposing surfaces, wherein one surface is intended for being placed proximal to the skin of a subject and the other surface facing away from the skin of the subject; wherein the array of microneedles is located on the surface proximal to the skin of the subject, the array comprising a multiplicity of microneedles, wherein each of the microneedles comprises:
  a skeleton made of a rigid material, the skeleton comprises:

a sharp tip section located on one end of the skeleton, the sharp tip section being configured to penetrate a skin of a subject;
a base on an opposing end of the skeleton; and
a middle section connecting between the sharp tip section and the base; and
a skin augmentation composition comprising at least one biocompatible ceramic material, wherein the augmentation composition at least partly surrounds the middle section, such that a diameter of the sharp tip section is larger than a diameter of the augmentation composition.

According to some embodiments, the present invention provides a method for delivering a skin augmentation composition to a site of skin defect or deficiency, comprising placing at the site an applicator configured for administration of a skin augmentation composition to a skin of a subject, the applicator comprising a substrate and an array of microneedles; wherein the substrate has a generally flattened structure having two opposing surfaces, wherein one surface is intended for being placed proximal to the skin of a subject and the other surface facing away from the skin of the subject; wherein the array of microneedles is located on the surface proximal to the skin of the subject, the array comprising a multiplicity of microneedles, wherein each of the microneedles comprises:
a skeleton made of a rigid material, the skeleton comprises:
a sharp tip section located on one end of the skeleton, the sharp tip section being configured to penetrate a skin of a subject;
a base on an opposing end of the skeleton; and
a middle section connecting between the sharp tip section and the base; and
a skin augmentation composition comprising hydroxyapatite beads and/or particles or a salt or derivative thereof, wherein the augmentation composition at least partly surrounds the middle section, such that a diameter (or cross section area) of the sharp tip section is larger-than—or equal to—a diameter (or cross section area) of the augmentation composition or the same diameter. Each possibility represents a separate embodiment of the present invention.

According to some embodiments, undesired fold, wrinkle, line or depressed area refers to undesired fold, wrinkle, line or depressed area in skin, in sub-cutaneous layers or a combination thereof. Each possibility represents a separate embodiment of the present invention. According to some embodiments, skin defect or deficiency refers to a defect or a deficiency in skin, in sub-cutaneous layers or a combination thereof. Each possibility represents a separate embodiment of the present invention. According to some embodiments, the method of the invention comprises placing at the site an applicator configured for administration of a skin augmentation composition to a skin of a subject or to sub-cutis layers of a subject or a combination thereof. Each possibility represents a separate embodiment of the present invention.

According to some embodiments, the present invention provides a method for filling an undesired fold, wrinkle, line or depressed area in a subject, comprising placing at the site of the fold, wrinkle, line or depressed area an applicator configured for administration of a skin augmentation composition to a skin of a subject, the applicator comprising a substrate and an array of microneedles; wherein the substrate has a generally flattened structure having two opposing surfaces, wherein one surface is intended for being placed proximal to the skin of a subject and the other surface facing away from the skin of the subject; wherein the array of microneedles is located on the surface proximal to the skin of the subject, the array comprising a multiplicity of microneedles, wherein each of the microneedles comprises:
a skeleton made of a rigid material, the skeleton comprises:
a sharp tip section located on one end of the skeleton, the sharp tip section being configured to penetrate a skin of a subject;
a base on an opposing end of the skeleton; and
a middle section connecting between the sharp tip section and the base; and
a skin augmentation composition comprising hydroxyapatite beads and/or particles and/or a salt or derivative thereof, wherein the augmentation composition at least partly surrounds the middle section, such that a diameter of the sharp tip section is larger than a diameter of the augmentation composition. Each possibility represents a separate embodiment of the present invention.

According to some embodiments, the present invention provides an applicator configured for administration of a skin augmentation composition to a skin and/or sub-cutis of a subject for use in filling an undesired fold, wrinkle, line or depressed area in a subject, the applicator comprising a substrate, wherein the substrate has a generally flattened structure having two opposing surfaces, wherein one surface is intended for being placed proximal to the skin of a subject and the other surface facing away from the skin of the subject; and an array of microneedles, wherein the array of microneedles is located on the surface proximal to the skin of the subject, the array comprising a multiplicity of microneedles, wherein each of the microneedles comprises:
a skeleton made of a rigid material, the skeleton comprises:
a sharp tip section located on one end of the skeleton, the sharp tip section being configured to penetrate a skin of a subject;
a base on an opposing end of the skeleton; and
a middle section connecting between the sharp tip section and the base; and
a skin augmentation composition comprising at least one biocompatible ceramic material, wherein the augmentation composition at least partly surrounds the middle section, such that a diameter of the sharp tip section is larger than a diameter of the augmentation composition.

According to some embodiments, the methods of the invention are useful for delivering a skin augmentation composition to a site of skin defect or deficiency. According to some embodiment, the site of skin defect or deficiency is undesired lines, wrinkles folds and the like in the skin of a subject. According to some embodiment, the site of skin defect or deficiency is undesired lines, wrinkles folds and the like in the facial skin of a subject. According to some embodiments, the methods of the invention are useful for filling an undesired fold, wrinkle, line or depressed area in a subject. Each possibility represents a separate embodiment of the present invention.

As used herein, the terms "placing" and "administering" are used interchangeably and refer to locating the applicator of the invention at a desired site. According to some embodiments, following administration, the microneedles penetrate the treatment area and the composition of the invention is delivered to the target site. In a non-limiting example, placing the applicator over a forehead wrinkle results in insertion of the microneedles to the skin of the subject and delivery of the composition of the invention to the dermal and/or sub-dermal layer. According to some embodiments, following placing the applicator on the skin of a subject, the microneedles penetrate the skin and the biodegradable polymer and/or salt undergo biodegradation, thus releasing the biocompatible ceramic which remains in the subject following removal of the applicator.

According to some embodiments, the site of skin defect or deficiency is the site of a scar. According to some embodiments, the terms "treated area" and "treatment area" are interchangeable and refer to a site of skin or sub cutis defect or deficiency, or a combination thereof. Each possibility represents a separate embodiment of the present invention. According to some embodiments, the site of skin or sub cutis defect or deficiency is the site of a depressed scar. Each possibility represents a separate embodiment of the present invention. According to some embodiments, the methods of the invention are useful in augmentation of scars. According to other embodiments, the methods of the invention are useful in filling skin and/or sub cutis scar tissue. Each possibility represents a separate embodiment of the present invention. As used herein, the term "normal skin" refers to a healthy skin and/or a young looking skin.

Non-limiting examples of a site of skin or sub cutis defect or deficiency which may be treated by the applicator of the invention, according to some embodiments, may comprise: delicate forehead, cheek, neck, nasal-bridge and lip wrinkles, nasolabial folds, marionette lines, depressed scars, lips, area of malar bones and a combination thereof. Each possibility represents a separate embodiment of the present invention.

According to some embodiments, the applicator is placed at a site of skin defect or deficiency or at undesired lines, wrinkles folds for at least 1, 2, 3, 5, 6, 7, 8, 9, 10, 11, 12 hours. Each possibility represents a separate embodiment of the present invention. According to some embodiments, the applicator is placed at a site of skin defect or deficiency or at undesired lines, wrinkles folds for at least a full night. As used herein, a full night is between 6-10 hours. According to some embodiments, the applicator is placed at a site of skin defect or deficiency or at undesired lines, wrinkles folds for at least 24 hours. Each possibility represents a separate embodiment of the present invention. According to some embodiments, the applicator is placed at a site of skin defect or deficiency or at undesired lines, wrinkles folds for at least 1, 2, 3, 5, 6, 7 days. Each possibility represents a separate embodiment of the present invention. According to some embodiments, the applicator is placed at a site of skin defect or deficiency or at undesired lines, wrinkles folds for a period of time sufficient for the degradation of the biodegradable carrier. Typically, the applicator is placed at a site of skin defect or deficiency or at undesired lines, wrinkles folds for 24-72 hours.

According to some embodiments, the skin augmentation composition is a slow-releasing skin augmentation composition. As used herein, the term "slow-releasing skin augmentation composition" refers to a composition configured for slow-release of a skin augmentation material and/or of a drug and/or of a toxin. Each possibility represents a separate embodiment of the present invention. In a non-limiting example, the applicator of the invention comprising a slow-releasing skin augmentation material is placed on the face of the subject for several days. According to this non-limiting example, the applicator may induce slow release and slow delivery of the skin augmentation material, thus achieving a more efficient augmentation of the target site.

According to some embodiments, the subject places the applicator of the invention at a desired site. According to some embodiments, the applicator of the invention remains at a desired site for a desired time period through the use of an adhesive. As used herein, the adhesive is inert, biologically compatible and enables easy removal of the applicator of the invention. According to some embodiments, the adhesive is resistant to water. According to some embodiments, the adhesive is located only on part of the inner surface of the substrate. According to some embodiments, the applicator of the invention is resistant to water. According to some embodiments, the applicator is shaped like an adhesive bandage so that it may be placed inconspicuously on the subject's face for a desired time. According to some embodiments, the applicator of the invention may be affixed to the treatment area using external fixation aid such as, but not limited to, a bandage, a handkerchief and the like.

According to some embodiments, the applicator is removed following a desired time period. According to some embodiments, the desired time period depends on the types of microneedles and skin augmentation compositions used in the applicator, on the amount of composition used, on the site of treatment, on the desired effect and a combination thereof. Each possibility represents a separate embodiment of the present invention.

According to some embodiments, following removal of the applicator, at least part of the skin augmentation composition remains at the site of administration while the microneedles' skeletons are removed with the applicator. According to some embodiments, following removal of the applicator, at least part of the biocompatible ceramic remains at the site of administration while the microneedles' skeletons are removed with the applicator.

According to some embodiments, the invention provides a kit comprising at least one of the applicators of the invention and instructions for use of the applicator. According to some embodiments, the applicators, methods and kits of the invention may be used by the subject without needing assistance from a medical care giver. According to some embodiments, the applicators, methods and kits of the invention do not require surgical intervention. According to some embodiments, the methods of the invention are used to fill undesired lines, wrinkles, depressed scars and folds in the face of a subject without use of surgical intervention or needles. Each possibility represents a separate embodiment of the present invention.

According to some embodiments, the method of the invention would have to be repeated several times in order to fill a site of skin defect or deficiency. According to other embodiments, a single use of the applicator of the invention is sufficient to fill a site of skin defect or deficiency. According to some embodiments, the dimensions and/or shape of the site of skin defect or deficiency determine how many times the applicator of the invention would have to be used at the same site of skin defect or deficiency in order to achieve the desired filling. Each possibility represents a separate embodiment of the present invention. In a non-limiting example, a deep and/or wide and/or irregularly shaped skin defect or deficiency may require several repetitions of the method of the invention and/or several applicators of the invention and/or a longer application time for proper filling of the skin defect or deficiency. Each possibility represents a separate embodiment of the present invention.

As used herein, the terms "subject", "a subject in need thereof" and "a patient in need thereof" are used interchangeably and refer to a subject in need of skin or sub cutis augmentation or a combination thereof. According to some embodiments, the subject is a subject having undesired lines, wrinkles, and folds such as, but not limited to, elderly people. According to other embodiments, the subject is a subject having a scar in need of augmentation or filling. In a non-limiting example, a subject is a subject having facial wrinkles which he or she would like to have filled for a healthier and fuller looking facial skin. Of note, a subject may have normal looking skin and wish to use the applicator/method of the invention in order achieve an appearance of fuller skin at a desired area, such as, but not limited to, the cheeks and lips.

As used herein, the term "about" refers to +/−10%, preferably +/−5%, most preferably +/−1%. Each possibility represents a separate embodiment of the present invention.

As used herein, the terms "sub cutaneous" and "sub cutis" are used interchangeably. It is to be understood that the applicator and/or the microneedles of the invention are configured for administration of a skin augmentation composition to skin or to sub-cutaneous layers or to a combination thereof. It is to be understood that the methods of the invention provide augmentation or filling of skin or sub cutaneous layers or a combination thereof.

According to some embodiments, the present invention provides a use of the applicator of the invention for augmentation of skin in a subject in need thereof. According to some embodiments, the present invention provides a use of the applicator of the invention for the filling of an undesired fold, wrinkle, line or depressed area in the skin of a subject in need thereof.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

EXAMPLES

Example 1. Treatment of Delicate Forehead Wrinkles

An applicator comprising a substrate in the form of a strip, comprises an array of microneedles with a skin augmentation composition, such as RADIESSE®. The applicator is placed on a delicate forehead wrinkle and adheres to the subject's face using an adhesive surface comprised in the substrate's surface which is proximal to the skin. The applicator is kept on the skin of the subject for a time period as desired by the user, the caregiver or as instructed by the instructions of the applicator.

Example 2. Treatment of a Nasolabial Fold

An applicator comprising a substrate in the form of a patch is placed on a nasolabial fold. The microneedles of the applicator comprise skeletons having a cylindrical base, a middle section in the form of a cylindrical longitudinal core and a conical sharp tip section. The skeleton further comprises a leakage stopper in the form of a cone, integrally formed with the sharp tip section. The middle section of the skeleton of each microneedle is surrounded by a skin augmentation composition. The skin augmentation composition comprises hydroxyapatite beads (40 μm), polyethylene glycol (40 kDa) and beads of magnesium sulfate. The applicator adheres to the subject's face using an adhesive surface comprised in the substrate's surface which is proximal to the skin. The applicator is kept on the skin of the subject for a time period as desired by the user, the caregiver or as instructed by the instructions of the applicator. The applicator is removed along with the skeletons of the microneedles, while the skin augmentation composition remains within the treated area.

Example 3. Preparation of an Augmentation Composition Comprising Hydroxyapatite

Hydroxyapatite (100 gr) is dispersed in molten polyethylene glycol (PEG 20000) using vigorous stirring. Next, a concentrated magnesium sulfate solution is prepared by dissolving 30 gr of magnesium sulfate in hot water and the hot solution is added to the molten PEG solution with constant mixing. The mixture is mixed until cooled to a paste.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. It is to be understood that further trials are being conducted to establish clinical effects.

According to some embodiments, the present invention provides, a microneedle-based applicator for delivery of a skin augmentation composition to the skin of a subject, the composition comprising at least one biocompatible filler material. The applicators of the invention provide an efficient, comfortable and easy-to-use delivery system for skin augmentation compositions. The present invention further provides delivery methods of skin augmentation compositions to the skin of a subject. The methods of the invention enable, inter alia, filling of undesired folds, wrinkles, or lines in a subject's skin. In certain embodiments, the methods of the invention enable a subject to use the applicators and methods of the invention without the help of a trained medical professional. According to other embodiments, the applicators of the invention may be supplied as disposable strips or patches.

Reference is now made to FIGS. 9A-9C and 10A-10C, which schematically demonstrate a microneedle 1100, according to some embodiments of the invention. According to some embodiments of the invention, a microneedle 1100 is provided, configured for administration of a biocompatible medical composition to a dermis layer and/or hypodermis layer of a subject, the microneedle comprising:

a rigid rod section 1110 having at least one open cavity 1111 along its length, the cavity is configured to temporarily accommodate a biocompatible medical composition there-within;

a rigid sharp tip 1120, at one end of the rod, configured to allow penetration of at least a part of the rod to a dermis layer and/or hypodermis layer of a subject.

In certain embodiments, the material of the microneedle is an absorbable material configured to be absorbed in the dermis layer or hypodermis layer or in both dermis layer and hypodermis.

In certain embodiments, the shape of the cross-section area of the rod is selected from: rectangular, triangular, circular, oval, polygonal, and any combination thereof. In certain embodiments, the shape of the cross-section area of the base 1121 of the sharp tip is similar or larger than the cross section of the rigid rod.

Figures 15A, 15B:
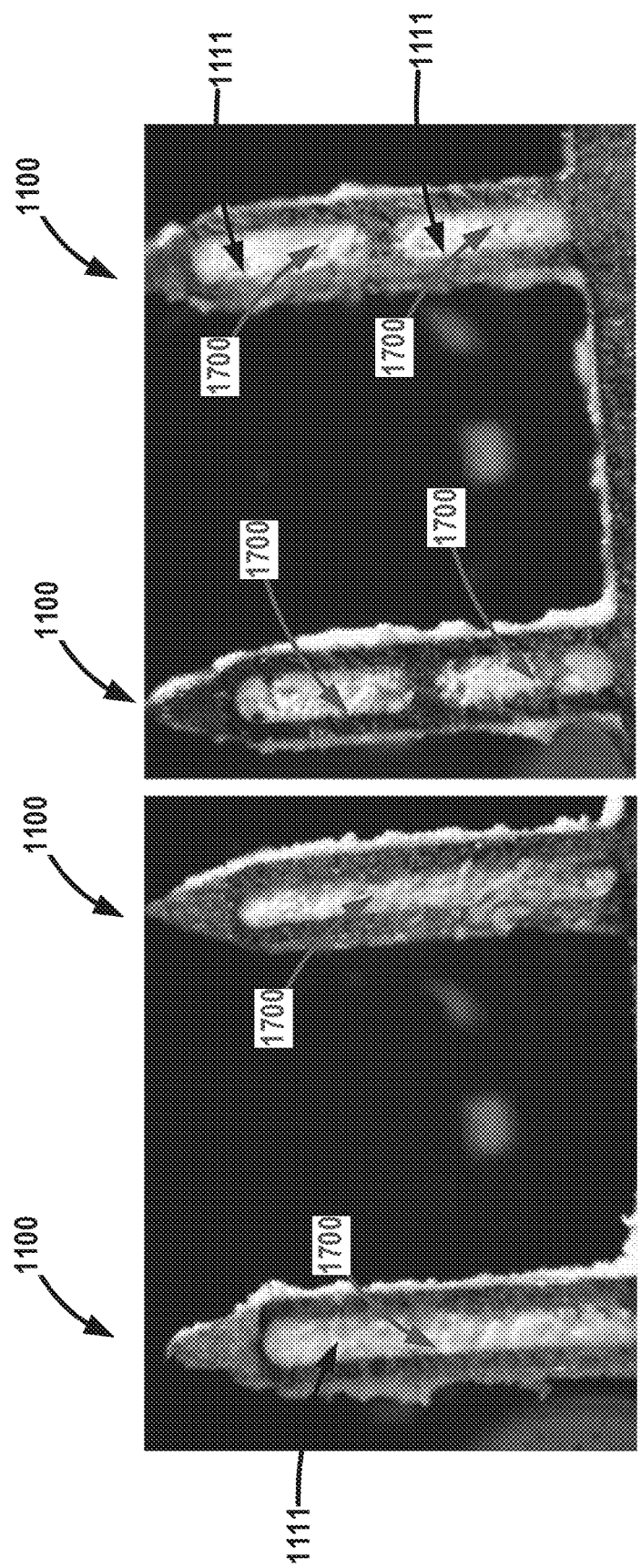
FIGS. 15A and 15B demonstrate the rigid skeletons of the microneedles, filled with the biocompatible medical compositions according to some embodiments of the invention.

In certain embodiments, and as demonstrated in FIGS. 15A and 15B, the cavity comprises the biocompatible medical composition 1700. In certain embodiments, the biocompatible medical composition is solid and/or semi-solid at room temperature and is dissolvable upon contact with liquid in the dermis layer and/or hypodermis layer.

In certain embodiments, the biocompatible medical composition is configured to at least partially separate from the cavity and the microneedle, when in dermis and/or hypodermis environment. In certain embodiments, the biocompatible medical composition comprises at least one of: skin augmentation composition, botulinum composition, medical pigment composition, steroids and any combination thereof.

In certain embodiments, the biocompatible medical composition comprises:
  at least one of: skin augmenting material, botulinum material, medical pigment material, steroids and any combination thereof; and
  at least one dispersant material, configured to disperse the at least one of: skin augmenting material, botulinum material steroids, and medical pigment material, upon contact with the dermis layer and/or the hypodermis layer.

In certain embodiments, the dispersant material is configured to promote diffusion and/or solubility in water and/or water solution, and is selected from: water-soluble polymer, polyethylene glycol (PEG), polyethylene oxide (PEO), polyoxyethylene (POE), glycerin, magnesium sulfate, salt, and any combination thereof.

In certain embodiments, the microneedle further comprises a rigid base section 1130, at the second end of the rod. In certain embodiments, the length (b) of the base section is at least 30 µm.

In certain embodiments, the sharp tip section and/or the base section substantially devoid of the biocompatible medical composition and/or dispersant. According to some embodiments, the sharp tip section and the base section of the microneedle are configured to remain devoid of the skin augmentation composition, and to prevent delivery of the skin augmentation composition to the epidermis or to the epidermis and upper dermis.

In certain embodiments, at least two microneedles are connected via their base section 1130 to a rigid connecting bar 1140. In some embodiments at least two microneedles are manufactured as one rigid element, which includes the connecting bar 1140 and the microneedle/s 1100 thereon, as demonstrated in FIG. 10A-10C.

Figure 9C:
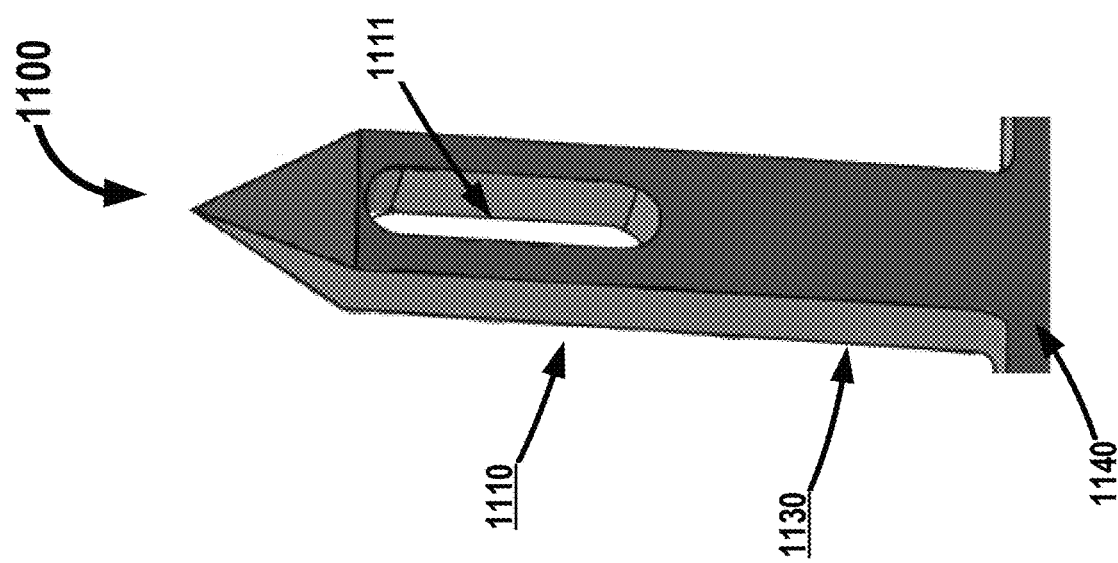
FIGS. 9A, 9B and 9C schematically demonstrate the rigid skeletons of the microneedles, according to some embodiments of the invention.
Figure 9B:
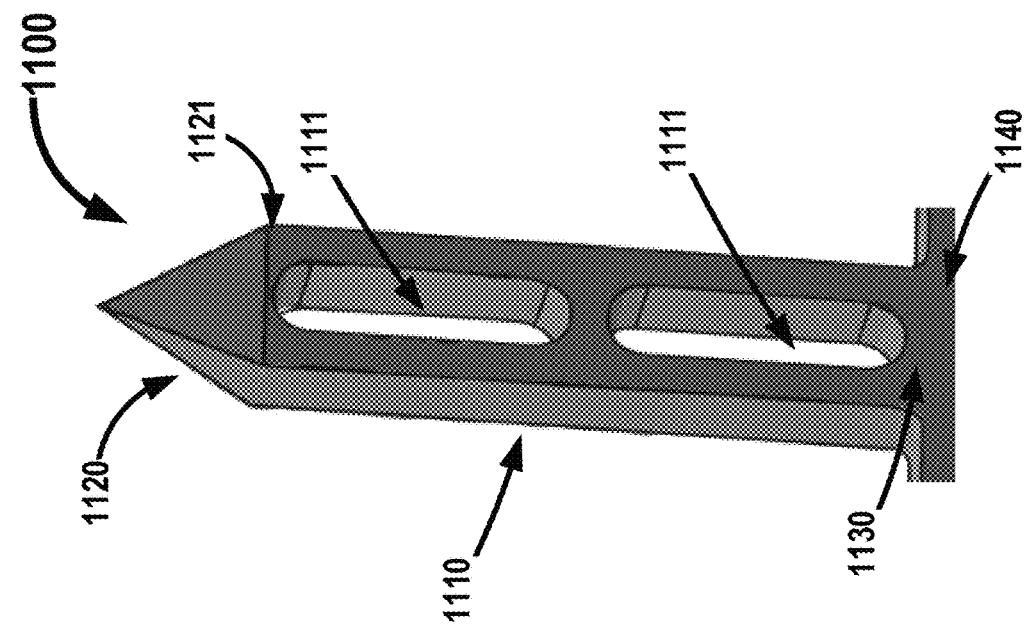
Figure 9A:
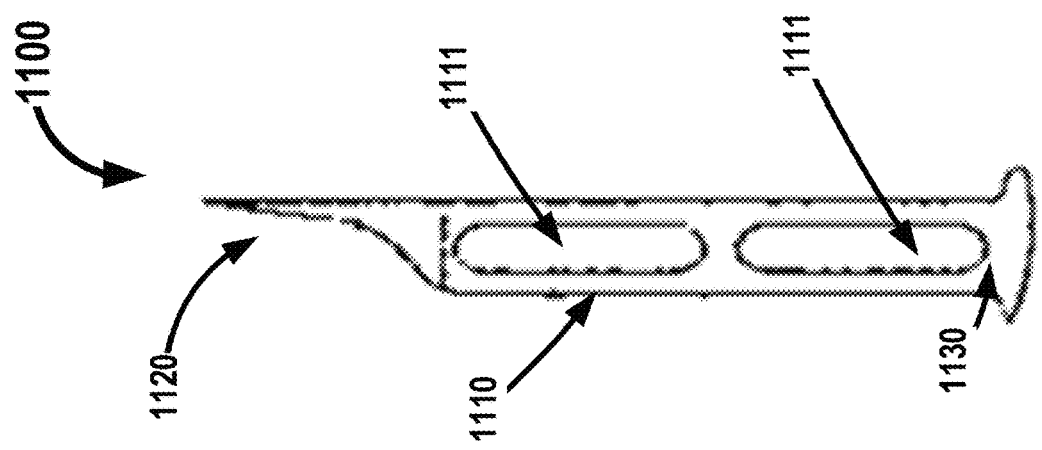

In certain embodiments, for the case of mass-production, it is preferred to manufacture microneedle/s 100 having a rectangular configuration, as demonstrated in FIGS. 9B and 9C. In certain embodiments, it is preferred to manufacture the microneedle/s together the rigid connecting bar, having a rectangular configuration (with rectangular cross-sections), as demonstrated in FIG. 10C.

Figure 10B:
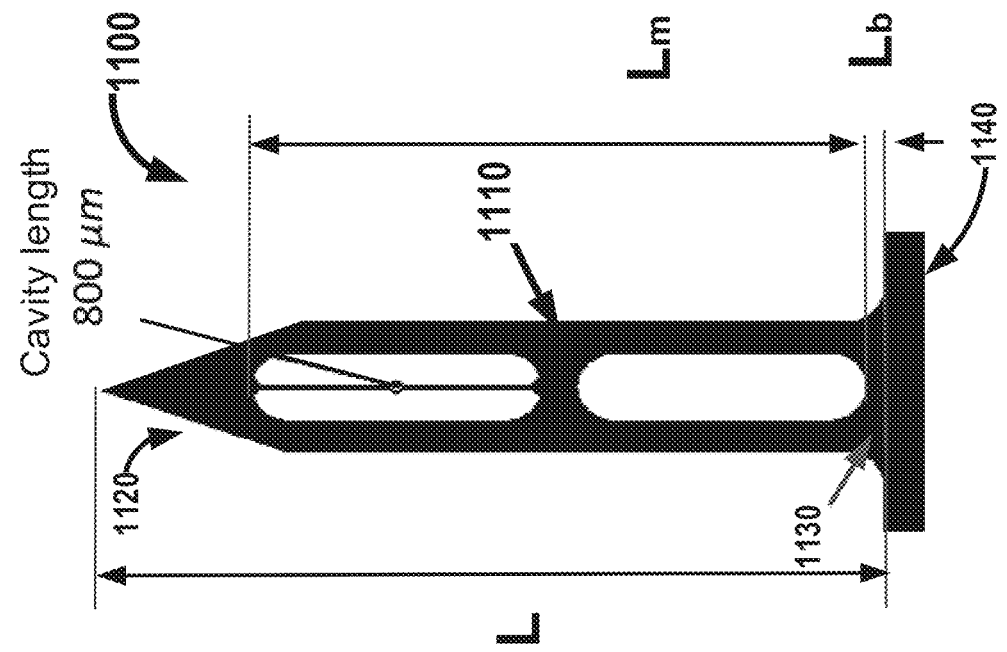
FIGS. 10A and 10B schematically demonstrate the rigid skeletons of the microneedles, according to some embodiments of the invention, indicating certain length measurements.
Figure 10A:
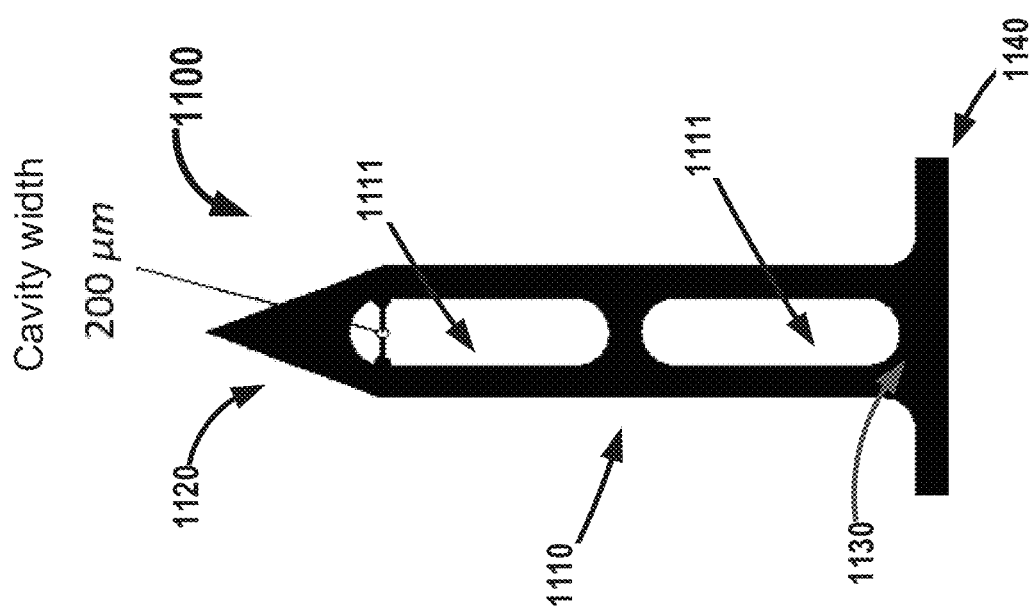
Figure 10C:
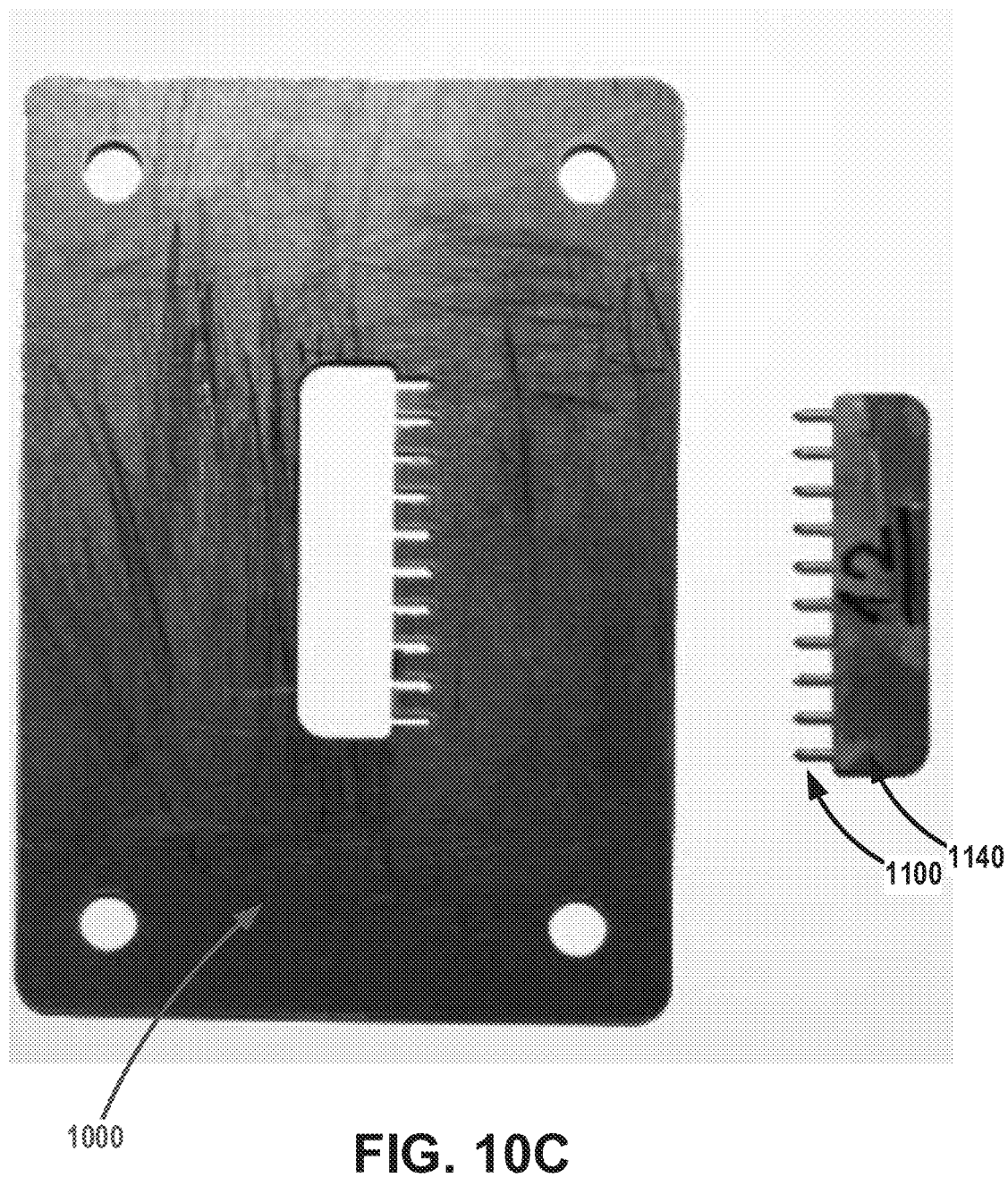
FIG. 10C demonstrates a manufacturing method for the microneedle/s together a rigid connecting bar, having rectangular configurations.
Figure 11A:
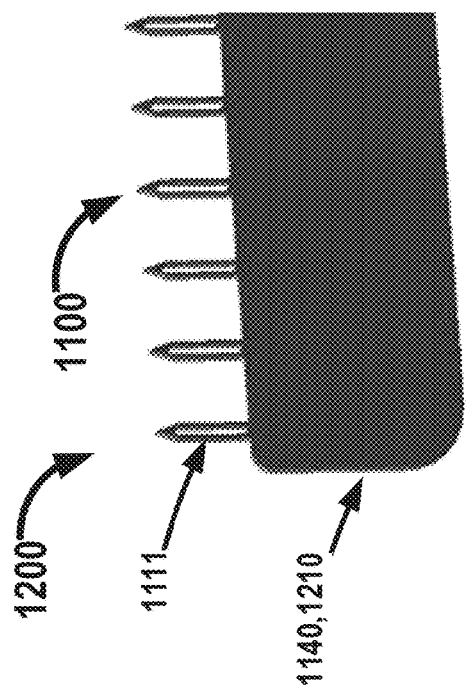
FIGS. 11A, 11B, 11C and 11D demonstrate applicators having the rigid skeletons of the microneedles according to some embodiments of the invention, arranged in a single line in an applicator, according to some embodiments of the invention.
Figure 11B:
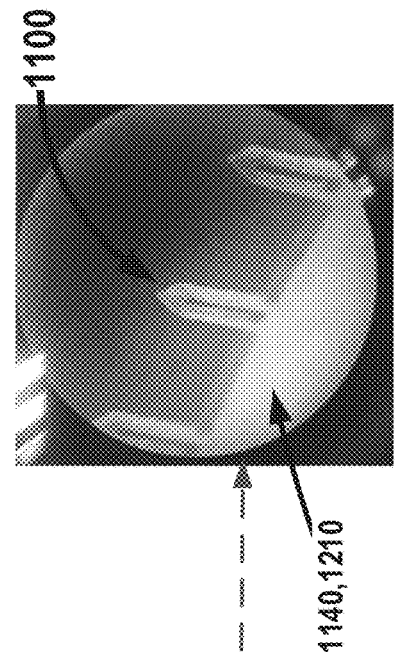
Figure 11C:
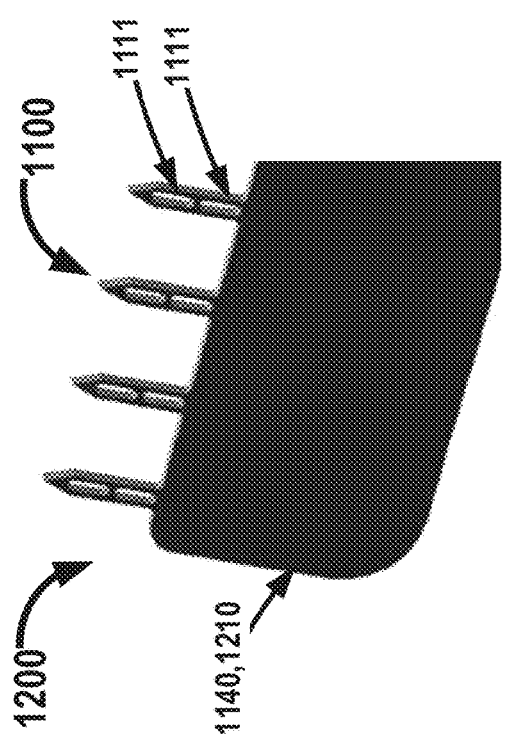
Figure 11D:
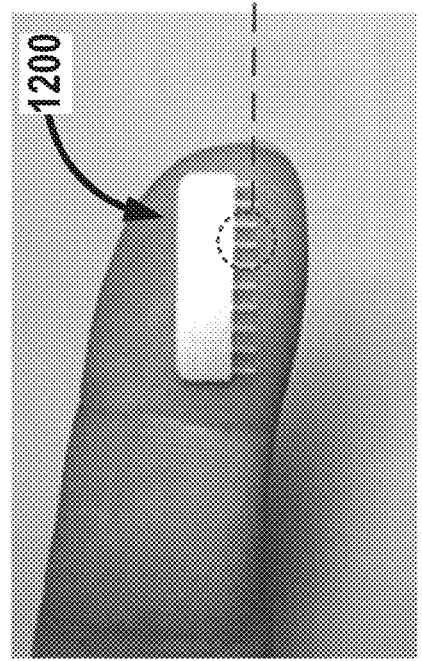
Figure 12:
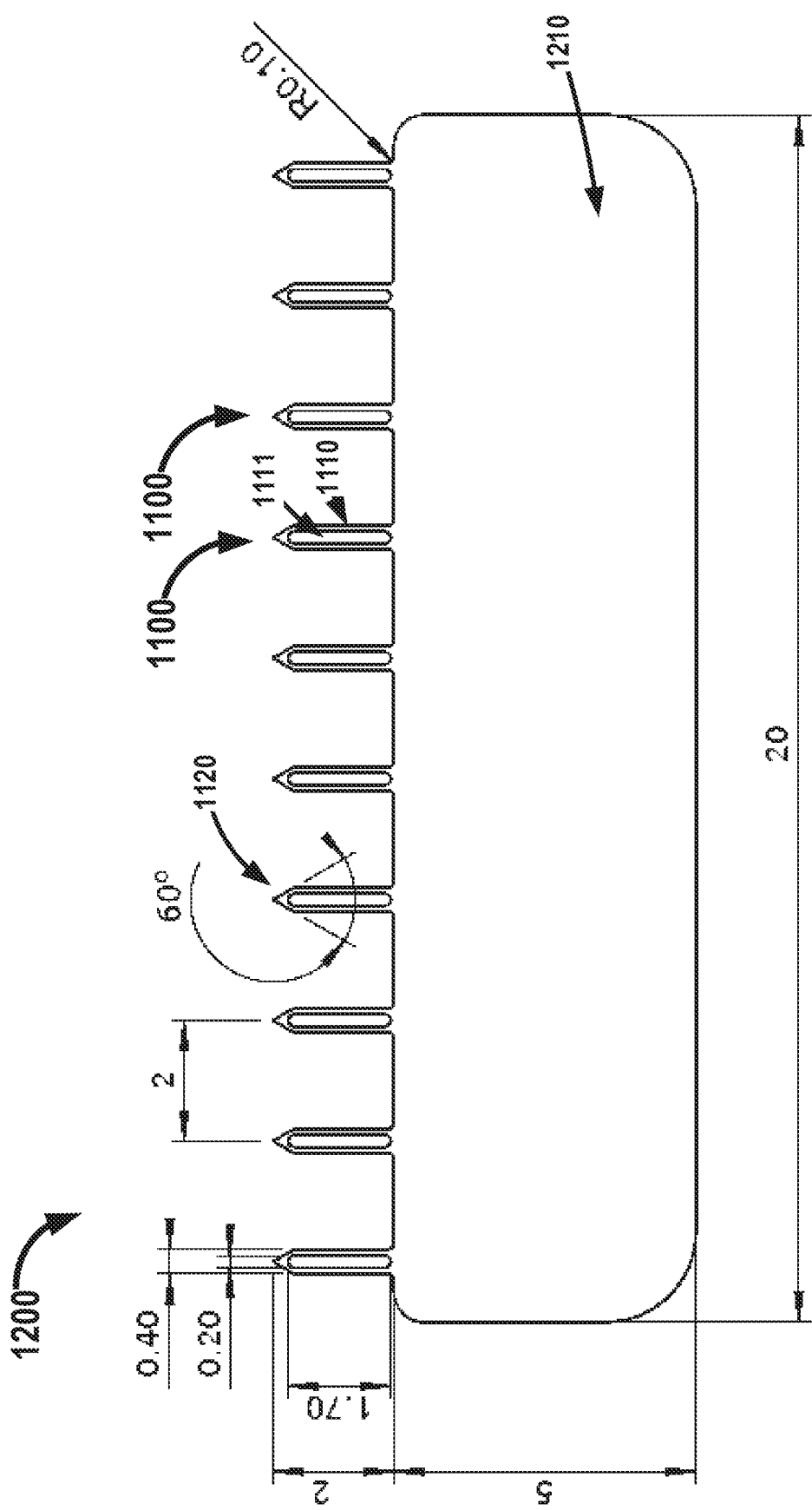
FIG. 12 schematically demonstrates an applicator, according to some embodiments of the invention, indicating certain lengths (in millimeters mm) and angle measurements.

According to some embodiments, and as demonstrate in FIG. 10C, a method is provided configured for manufacturing the applicator according any one of the above mentioned embodiments, the method comprising:
  cutting and/or carving at least one applicator from a sheet of a rigid material; and
  spreading the biocompatible medical composition onto the cavity/ies of the microneedles rod sections, such that cavities are filled.

According to some embodiments, in a case where an applicator is kept in the sheet template after the cutting/carving, a step of removing the applicator/s out of sheet is provided after the step of spreading the biocompatible medical composition.

According to some embodiments, in a case where the step of cutting or carving the at least one applicator is provided such that the cut/curved applicator is out of the sheet, the method further comprising a step of returning the cut/curved applicator/s back to the sheet template, before spreading the composition, and then removing the cut/curved applicator/s out again after the spreading step.

According to some embodiments, the manufacturing of the applicator can be by pouring the melted rigid material into an appropriate mold/s that is configured to provide the applicator according to any one of the above mentioned embodiments, and then cooling the rigid material. According to come embodiments the mold is configured to provide at least one of: the microneedles, the substrate, the whole applicator. In such embodiments, the step of spreading the biocompatible medical composition, onto the cavity/ies of the microneedles rod sections, is provided while the applicator is in the mold.

According to some embodiments, the applicator or at least the microneedles and/or the substrate can be manufactured by at least one method of: laser cutting, stamping, milling, punching, sintering, electron beam machining, electrochemical etching and any combination thereof. According to some embodiments, the cavity/ies are carved after the production of the microneedle, by any of the above methods.

According to some embodiments, the perpendicular attachment of the microneedle to the substrate can be by: mechanical firm support, chemical bonding, adhesive materials and any combination thereof.

According to some embodiments, the microneedles cavities can be loaded with the augmentation material before and/or after their attachment to the substrate. According to some embodiments, in the case of loading the augmentation material before the attachment of the microneedles to the substrate, the augmentation material is to be dried and mechanically stable before the attachment of the microneedles to the substrate.

According to some embodiments, the attachment positioning of the needles to the substrate can be made in any array configuration, as long as they are perpendicular to the surface.

According to some embodiments, the method further comprising a step of removing any excessive composition from at least one of: the substrate, the tip section, the base section, and the outer surface of the rigid rod, while leaving the composition within the cavity/ies.

According to some embodiments, the method further comprising a step of providing the biocompatible medical composition with:
  at least one of: skin augmenting material, botulinum material, medical pigment material, steroids, and any combination thereof; and at least one dispersant material in a frozen state, configured to disperse by melting while in the tissue, at least one of the: skin augmenting material, botulinum material, steroids, and medical pigment material, upon contact with the dermis layer and/or the hypodermis layer.

According to some embodiments, the method further comprising a step of connecting together at least two applicators with having a single microneedles' row, to provide an applicator with multiple microneedle rows.

According to some embodiments, the method further comprising a step of selecting the rigid material for manufacturing the applicators from a group consisting of: metal, plastic, polymeric, a ceramic material, a silicone, and an absorbable material configured to be absorbed in the dermis layer or hypodermis layer or in both dermis layer and hypodermis.

In certain embodiments, the base section is configured to be connected and/or anchored to a substrate 1310, as demonstrated in FIGS. 13 and 14. In certain embodiments, the base section is connected and/or anchored to a section of a substrate, such that the rod is about perpendicular to the section of the substrate.

The present invention provides, in one aspect, a microneedle 1100 for administering a skin augmentation composition to the dermis layer or hypodermis layer of human facial or neck skin, the microneedle comprising:

a. a skin augmentation composition 1700, demonstrated for example in FIGS. 15A-15B; the skin augmentation composition comprising at least one biocompatible skin augmenting material, and at least one biocompatible dispersant, which disperses the skin augmenting material upon contact with the dermis layer or hypodermis layer; and b. a skeleton made of a rigid material, the skeleton comprises:

i. a base section 1130 on one end of the skeleton; in certain embodiments, the base section having a height of at least about 30 μm (micron, micrometer); in certain embodiments, the base section substantially devoid of a skin augmenting material;

ii. a middle section 1110 connected to the base section at one end; in certain embodiments, the middle section having a height of between about 35 μm to about 2500 μm; the middle section is configured to accommodate the skin augmentation composition; wherein the middle section is configured to at least partly expose the accommodated skin augmentation composition to the outer surface of the microneedle; and iii. a sharp tip section 1120 connected to the middle section at the other end and configured to penetrate human facial or neck skin; in certain embodiments, the base 1121 of the tip section having a cross-section area same or larger than the cross-section area of the middle section; in certain embodiments, the tip section substantially devoid of a skin augmenting material.

In certain embodiments, the terms "middle section" and "rod", as used herein, are alternatively used, having similar construction.

In certain embodiments, the skin augmentation composition is solid or semi-solid at room temperature, configured to dissolve upon contact with liquid. In certain embodiments, the term "semi-solid" as used herein, refers to material, or a composition of materials, having a gel like or paste like consistency.

The term "dispersant" as used herein refers to any material, which (a) absorbs fluids found in the dermis or hypodermis layers, (b) dissolves in fluids found in the dermis or hypodermis layers, (c) releases the skin augmenting material into the dermis or hypodermis, and/or (d) prevents flocculation of the particles of the skin augmenting material when administered to the dermis layer or hypodermis layer of human facial or neck skin. Each possibility represents a separate embodiment of the invention. According to the IUPAC definition, flocculation is "a process of contact and adhesion whereby the particles of dispersion form larger-size clusters". Flocculation is synonymous with agglomeration and coagulation/coalescence.

In certain embodiments, the dispersant prevents flocculation of the particles of the skin augmenting material when administered to the dermis layer or hypodermis layer of human facial or neck skin. In certain embodiments, the dispersant dissolves in fluids found in the dermis or hypodermis layers and releases the skin augmenting material from the microneedles into the dermis or hypodermis. In certain embodiments, the dispersant dissolves in fluids found in the dermis or hypodermis layers, releases the skin augmenting material into the dermis or hypodermis, and prevents flocculation of the particles of the skin augmenting material when administered to the dermis layer or hypodermis layer of human facial or neck skin. In certain embodiments, the dispersant dissolves in fluids found in the dermis or hypodermis layers, releases the skin augmenting material into the dermis or hypodermis, and prevents flocculation of the particles of the skin augmenting material when administered to the dermis layer or hypodermis layer of human facial or neck skin. In certain embodiments, the dispersant absorbs fluids found in the dermis or hypodermis layers, dissolves in fluids found in the dermis or hypodermis layers, releases the skin augmenting material into the dermis or hypodermis, and prevents flocculation of the particles of the skin augmenting material when administered to the dermis layer or hypodermis layer of human facial or neck skin.

According to some embodiments of the present invention, a skin augmentation application method is provided, by propelling the provided microneedle/s 1100 of the present invention into the dermis layer or hypodermis layer of human facial or neck skin, thereby enabling the liquids being either biological fluids normally found in the tissues, or pre-administered fluids (such as fluids of local anesthesia) to make contact with the skin augmentation composition of the present invention, and thereby allowing the dispersant to create a dispersion of the particles of the skin augmenting material in the biological liquids found in the dermis or hypodermis, or both.

In certain embodiments of the provided method, the liquids found in the dermis layer or hypodermis layer of human facial or neck skin are biological fluids or biocompatible fluids. In certain embodiments, the biological fluids are intracellular fluids (ICF) or extracellular fluids (ECF). In certain embodiments, the biocompatible fluids are biological fluids administered to the dermis layer or hypodermis layer of human facial or neck skin. In certain embodiments, the biocompatible fluids are non-biological fluids administered to the dermis layer or hypodermis layer of human facial or neck skin. In certain embodiments, the biocompatible fluids are fluids which do not elicit any undesirable and/or toxic local or systemic effects when administered to the dermis layer or hypodermis layer of human facial or neck skin. In certain embodiments, the biocompatible fluids comprise an agent for local anesthetic. In certain embodiments, the agent for local anesthetic is lidocaine. In certain embodiments, the biocompatible fluids include steroids. In certain embodiments, the biocompatible fluids are administered prior to the use of a microneedle or applicator as described above. In certain embodiments, the biocompatible fluids are administered during the use of a microneedle or applicator as described above. In certain embodiments, the biocompatible fluids are administered after the use of a microneedle or applicator as described above.

In certain embodiments of the provided method, the skin augmentation composition is devoid or substantially devoid of liquids. In certain embodiments, the skin augmentation composition comprises up to 5% by weight of liquids. In certain embodiments, the dispersant is water-soluble, water-degradable, or both.

In certain embodiments of the provided method, the skin augmentation composition is solid at room temperature, where the skin augmenting material is solid at room temperature and the dispersant is solid at room temperature. In certain embodiments, the skin augmentation composition is solid at room temperature, where the skin augmenting material is semi-solid at room temperature and the dispersant is solid at room temperature. In certain embodiments, the skin augmentation composition is solid at room temperature, where the skin augmenting material is solid at room temperature and the dispersant is semi-solid at room temperature. In certain embodiments, the skin augmentation composition is solid at room temperature, where the skin augmenting material is semi-solid at room temperature and the dispersant is semi-solid at room temperature. In certain embodiments, the skin augmentation composition is semi-solid at room temperature, where the skin augmenting material is solid at room temperature and the dispersant is solid at room temperature. In certain embodiments, the skin augmentation composition is semi-solid at room temperature, where the skin augmenting material is semi-solid at room temperature and the dispersant is solid at room temperature. In certain embodiments, the skin augmentation composition is semi-solid at room temperature, where the skin augmenting material is solid at room temperature and the dispersant is semi-solid at room temperature. In certain embodiments, the skin augmentation composition is semi-solid at room temperature, where the skin augmenting material is semi-solid at room temperature and the dispersant is semi-solid at room temperature.

In certain embodiments, the skin augmentation composition substantially consists of the biocompatible skin augmenting material and the biocompatible dispersant.

In certain embodiments, the skin augmentation composition comprising at least about 25% by weight of at least one biocompatible skin augmenting material, and at least about 1% by weight of at least one biocompatible dispersant. In certain embodiments, the skin augmentation composition comprises about 50% to about 75% by weight of the biocompatible skin augmenting material, and about 25% to about 50% by weight of the biocompatible dispersant. In certain embodiments, the skin augmentation composition comprises about 60% to about 65% by weight of the biocompatible skin augmenting material, and about 35% to about 40% by weight of the biocompatible dispersant. In certain embodiments, the skin augmentation composition comprises about 62.5% by weight of the biocompatible skin augmenting material, and about 37.5% by weight of the biocompatible dispersant.

In certain embodiments, the biocompatible dispersant disperses at least a portion of the skin augmenting material into the dermis layer, into the hypodermis layer, or into both the dermis layer and the hypodermis layer. In certain embodiments, the biocompatible dispersant disperses at least a portion of the skin augmenting material into both the dermis layer and the hypodermis layer.

In certain embodiments, the length ($L_b$) of the base section 1130 is between about 30 μm to about 60 μm, configured to enable the biocompatible dispersant to disperse at least a portion of the skin augmenting material into the dermis layer. In certain embodiments, the biocompatible dispersant further disperses at least a portion of the skin augmenting material into the hypodermis layer.

In certain embodiments, the length ($L_b$) of the base section 1130 is at least about 790 μm, configured to enable the biocompatible dispersant to disperse the skin augmenting material into the deep dermis layer and/or the hypodermis layer. In certain embodiments, the length of the base section 130 is between about 790 μm to about 820 μm, configured to enable the biocompatible dispersant to disperse the skin augmenting material into the deep dermis layer and/or the hypodermis layer.

In certain embodiments, the microneedle 1100 is between about 500 μm to about 7000 μm in height. In certain embodiments, the microneedle is between about 1000 μm to about 2500 μm in height. In certain embodiments, the microneedle is between about 1000 μm to about 1500 μm in height.

In certain embodiments, the microneedle's rigid material is selected from a group consisting of: metal, plastic, ceramic material, silicone, polymeric material and any combination thereof. In certain embodiments, the metal is stainless steel. In certain embodiments, the stainless steel is 304 stainless steel. In certain embodiments, the rigid material is an absorbable material in the tissue.

In certain embodiments, the base section 1130 has a shape selected from the group consisting of: a rectangular box, a cuboid, a cylinder, a triangular box and a polygonal box. In certain embodiments, the base section has a shape of a rectangular box or of a cylinder.

In certain embodiments, the middle section 1110 has a shape selected from the group consisting of a rectangular box, a cuboid, a cylinder, a triangular box and a polygonal box.

In certain embodiments, the middle section 1110 has a shape of one or more elongated boxes having elongated sidewalls and an elongated internal cavity 1111, each elongated box comprises open elongated sidewalls, for example 1-3 frames of an open window, configured to at least partly expose the skin augmentation composition to the outer environment of the microneedle. In certain embodiments, each elongated box comprises two opposing elongated sidewalls and two opposing elongated open sidewalls, as demonstrated at least in FIGS. 9B-9C. In certain embodiments, the height of each one of the elongated cavity is about 400 μm to about 800 μm and the width of each one of the elongated cavity is about 200 μm, as demonstrated in FIGS. 10A-10B. In certain embodiments, the skin augmentation composition is located in the elongated internal cavity 1111, between, near or attached to at least one elongated sidewall.

In certain embodiments, the middle section 1110 has a shape of one or more elongated cylinders (not shown), having elongated sidewalls and at least one elongated internal cavity, each elongated cylinder comprises an arcuate opening configured to at least partly expose the skin augmentation composition to the outer surface of the microneedle. In certain embodiments, each arcuate opening spans up to half of the circumference of the elongated sidewalls. In certain embodiments, the height of each one of the elongated cylinders is about 400 μm to about 2000 μm and the width of each one of the elongated cylinders is about 400 µm to about 1000 µm. In certain embodiments, the skin augmentation composition is located in the elongated internal cavity, between, near or attached to at least one elongated sidewall.

In certain embodiments, the middle section has a shape of one or more containers comprising the skin augmentation composition in at least one internal cavity, each container having perforated sidewalls configured to at least partly expose the skin augmentation composition to the outer surface of the microneedle.

In certain embodiments, the middle section has a shape of one or more containers comprising the skin augmentation composition in an elongated internal cavity, each container having perforated sidewalls configured to at least partly expose the skin augmentation composition to the outer surface of the microneedle.

In certain embodiments, the base 1121 of the sharp tip section 1120 has the same diameter or cross-section area as the total diameter or cross-section area (respectively) of the middle section and the skin augmentation composition. In certain embodiments, the base of the sharp tip section has a larger diameter or cross-section area than the total diameter or cross-section area (respectively) of the middle section and the skin augmentation composition. In certain embodiments, the base diameter (or respectively cross-section area) of the sharp tip section is about 5% to 20% larger than the total diameter (or respectively cross-section area) of the middle section and the skin augmentation composition. In certain embodiments, the sharp tip section comprises a tip having a 10° to a 60° angle. In certain embodiments, the sharp tip section has a shape selected from the group consisting of: a cone, a pyramid, a triangular pyramid and a polygonal pyramid.

In certain embodiments, the configuration of the microneedle 1100 is such that at least about 20% of the total volume of the needle is filled with the skin augmentation composition. In certain embodiments, at least about 40% of the total volume of the needle is filled with the skin augmentation composition. In certain embodiments, about 40% to about 50% of the total volume of the needle is filled with the skin augmentation composition.

In certain embodiments, the biocompatible skin augmenting material is calcium hydroxyapatite (or calcium hydroxylapatite) or hyaluronic acid. In certain embodiments, the biocompatible skin augmenting material is in the form of solid particles or solid spheres. In certain embodiments, at least 50% of the particles or spheres are about 10 µm to about 100 µm in diameter. In certain embodiments, at least 60% of the particles or spheres are about 15 µm to about 65 µm in diameter. In certain embodiments, at least 60% of the particles or spheres are about 25 µm to about 45 µm in diameter. In certain embodiments, at least 70% of the particles or spheres are about 25 µm to about 45 µm in diameter. In certain embodiments, about 10% of the particles or spheres are up to about 15 µm to about 35 µm in diameter. In certain embodiments, about 50% of the particles or spheres are up to about 35 µm to about 50 µm in diameter. In certain embodiments, about 90% of the particles or spheres are up to about 50 µm to about 70 µm in diameter. In certain embodiments, about 10% of the particles or spheres are up to about 26 µm in diameter. In certain embodiments, about 50% of the particles or spheres are up to about 41 µm in diameter. In certain embodiments, about 90% of the particles or spheres are up to 64 µm in diameter.

In certain embodiments, the biocompatible dispersant is a water-soluble polymer. In certain embodiments, the water-soluble polymer is polyethylene glycol (PEG), polyethylene oxide (PEO) or polyoxyethylene (POE). In certain embodiments, the water-soluble polymer has a molecular weight in the range of about 1000 to about 19000. In certain embodiments, the water-soluble polymer is PEG 12000. In certain embodiments, the biocompatible dispersant is glycerin, magnesium sulfate, salt, and any combination thereof.

In certain embodiments, no dispersant material is provided, in such cases, the water or solution, which allows the diffusion of the augmentation material can be provided from the treated tissue; in such cases the dispersing may take longer time.

Reference is now made to FIGS. 11A-11D, 12, 13 and 14, which demonstrate a skin applicator for administration of a biocompatible medical composition, according to some embodiments of the invention.

According to some embodiments of the invention, an application device 200,300 is provided configured for administration of a biocompatible medical composition to a dermis layer and/or hypodermis layer of a subject, the device comprising:
 a substrate 1210,1310, configured to be attached to the subject's skin; and
 at least one microneedle 1100, connected and/or anchored to the substrate, such that when the substrate is attached to the subject's skin, the at least one microneedle penetrates the dermis layer and/or hypodermis layer.

Figure 13:
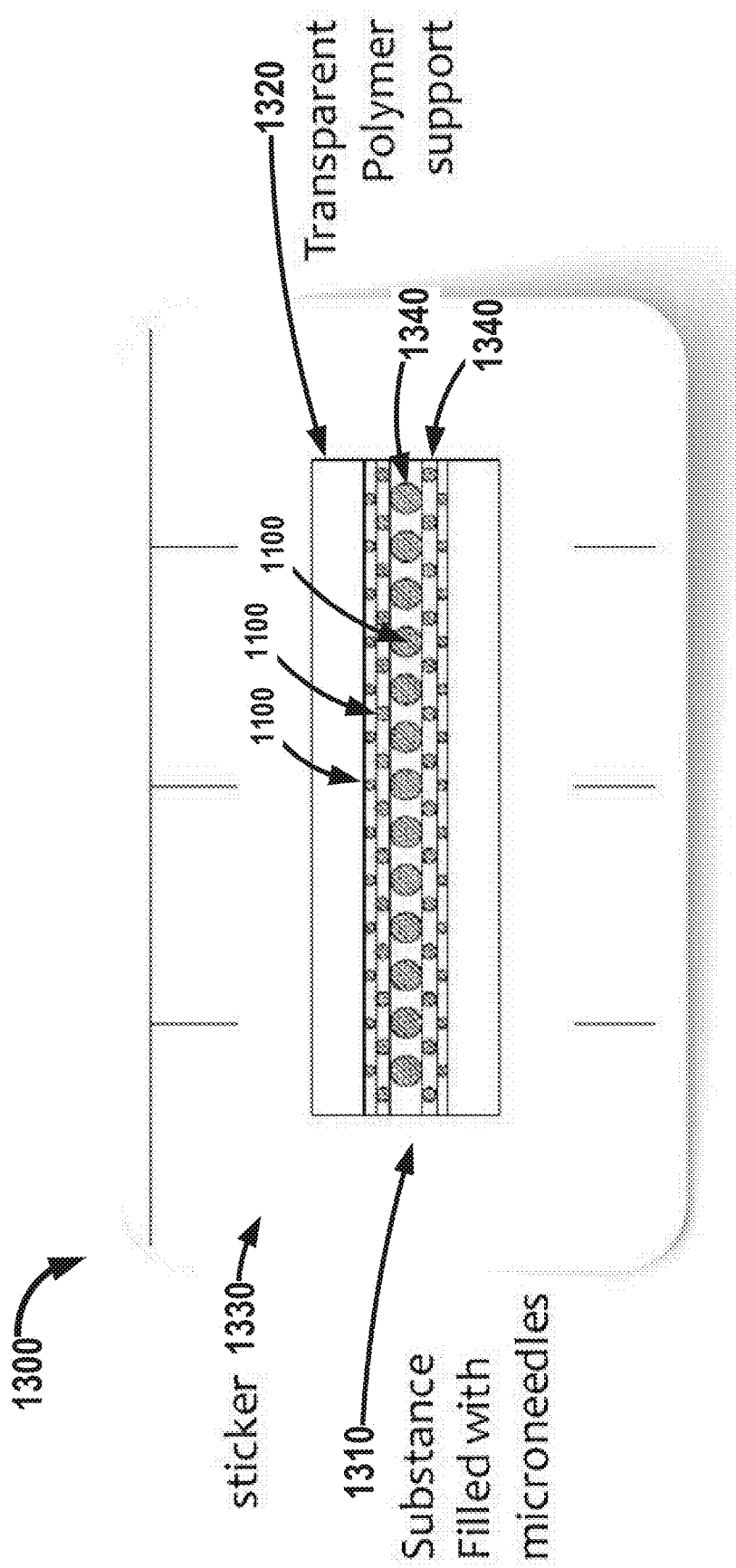
FIG. 13 schematically demonstrates an upper view of a patch applicator, according to some embodiments of the invention, including an array of multiple lines of different sizes of microneedles, according to some embodiments of the invention.

In certain embodiments, and as demonstrated in FIG. 13, at least a part of the substrate is transparent 1330. In certain embodiments some of the microneedles or all of them are attached and/or anchored to the substrate at its transparent section, such that a care giver can see their application on to the required skin area or line.

In certain embodiments, the substrate further comprises markings (not shown), on a surface of the substrate, which is opposite to the surface of the protruding microneedle/s. In certain embodiments, the markings configured to assist a care giver with the application of the microneedle/s.

In certain embodiments, the device 1200,1300 further comprising a plurality of the microneedles, arranged in a form selected from the group consisting of:
 at least one row (as demonstrated at least in FIGS. 11A-11D and 12),
 at least one array (as demonstrated in FIGS. 13 and 14),
 at least two segments 1340 (as demonstrated in FIGS. 13 and 14);
 and any combination thereof.

In certain embodiments, the segments of the microneedles, are configured to allow motion, one segment relative to another.

In certain embodiments, the segments of the microneedles, can be connected via a flexible or rigid connecting element 1610, configured to control the motion between the segments.

In certain embodiments, the plurality of the microneedles comprises various lengths (L) for the microneedles. In certain embodiments, the plurality of the microneedles comprises various cross-section area for the microneedles, for example in non-limited case of circular cross-section, the microneedles can have various diameters (demonstrated in FIG. 13).

In certain embodiments, the substrate comprises a rigid material, or a flexible material, or a combination of rigid and flexible materials. In certain embodiments, the substrate comprises an adhesive material, configured to attach at least a part of the substrate to the subject's skin. In certain embodiments, the substrate comprises a form of a strip or a patch.

According to some embodiments of the invention, a method for administrating a biocompatible medical composition to a dermis and/or hypodermis of a subject is provided; the method comprising:

providing at least one microneedle 1100, according to the various embodiments that are mentioned above, with a biocompatible medical composition; wherein the biocompatible medical composition is solid and/or semi solid at room temperature and is configured to dissolve and to be absorbed in the tissue when in contact with liquid environment of dermis layer and/or hypodermis layer;

inserting the at least one microneedle to the dermis layer and/or hypodermis layer of a subject; and optionally retracting the at least one microneedle from the dermis layer and/or hypodermis layer of the subject, after a predetermined time period.

In is noted that in certain embodiments, where the microneedles are made of a dissolvable material, which is configured to be absorbed in the dermis layer and/or hypodermis layer the step of retracting the microneedle/s is not needed, nor provided.

In certain embodiments, the step of providing microneedle/s with the biocompatible medical composition further comprises substantially devoid the tip section 1120 and/or the base section 1130 from including the biocompatible medical composition.

In certain embodiments, the method further comprising injecting an anesthetic material with water solution or water for injection to the treated area, about 1 minuet to about 30 minutes, prior to the insertion of the microneedle/s.

In certain embodiments, the step of inserting microneedle/s is provided via attaching an application device 1200,1300 to the skin of the treated area; the application device is according to the various embodiments that are mentioned above, which is configured with a substrate 1210,1310, and the at least one microneedle 1100. The attachment substrate 1210,1310 to the skin of the treated area inserts the microneedle/s to the dermis layer and/or to the hypodermis layer, according to the required treatment. Further according to these certain embodiments, the optional step of retracting comprises a retraction of the substrate 1210,1310, with the microneedle/s or without at least a part the microneedle/s 1100.

In certain embodiments, the method further comprises providing the biocompatible medical composition with:
at least one of: skin augmenting material, botulinum material, medical pigment material, steroids and any combination thereof; and
at least one dispersant material, configured to disperse the at least one of: skin augmenting material, botulinum material, medical pigment material, and steroids upon contact with the dermis layer and/or the hypodermis layer.

In certain embodiments, the dispersant material is configured to promote diffusion and/or solubility in water or water solution, and is selected from: water-soluble polymer, polyethylene glycol (PEG), polyethylene oxide (PEO), polyoxyethylene (POE), glycerin, magnesium sulfate, salt, and any combination thereof In certain embodiments, the predetermined time period is selected between about 0.5 to about 24 hours, optionally by providing the substrate with an adhesive material.

The present invention further provides, in another aspect, an applicator (demonstrated for example 1200 in FIGS. 11A-11D and 12, and 1300 in FIGS. 13 and 14) configured for administration of a skin augmentation composition to the dermis layer or hypodermis layer of facial or neck skin, comprising a microneedle as described above.

In certain embodiments, the applicator 1200,1300 comprises:
(a) a substrate 1210,1310 having a generally flattened structure having two opposing surfaces, wherein one surface is intended for being placed proximal to the skin of a subject and the other surface facing away from the skin of the subject; and
(b) at least one row and/or array of microneedles 1100 located on the surface intended for being placed proximal to the skin of the subject, the row/array comprising a multiplicity of microneedles as described above.

In certain embodiments, the distance between microneedles is selected between 0.5 mm and 2.5 mm.

In certain embodiments, and as demonstrated in FIGS. 11A-11D and 12, the applicator 1200 comprises a form of a strip. In certain embodiments, and as demonstrated in FIGS. 13 and 14, the applicator 1300 comprises a form of a patch.

The present invention further provides, in another aspect, an application method for filling an undesired fold, wrinkle, line or depressed area in the dermis layer or hypodermis layer of facial or neck skin of a subject, comprising attaching to the site of the fold, wrinkle, line or depressed area, a microneedle 1100 as described above or a at least one applicator 1200,1300 as described above.

In certain embodiments, the microneedle or applicator are kept attached to the site of the fold, wrinkle, line or depressed area, for about 0.5 to about 24 hours.

The present invention further provides, in another aspect, a microneedle as described above, or an applicator as described above, for use in filling an undesired fold, wrinkle, line or depressed area in the dermis layer or hypodermis layer of facial or neck skin.

The present invention further provides, in another aspect, a skin augmentation composition comprising about 25% to about 95% by weight of at least one biocompatible skin augmenting material, and about 1% to about 75% by weight of at least one biocompatible dispersant.

According to a further aspect, the present invention provides an applicator 1300 configured for administration of a skin augmentation composition to a skin of a subject, the applicator comprising:
a substrate 1310, wherein the substrate has a generally flattened structure having two opposing surfaces, wherein one surface is intended for being placed proximal to the skin of a subject and the other surface facing away from the skin of the subject; and
an array of microneedles 1100, wherein the array of microneedles is located on the surface proximal to the skin of the subject, the array comprising a multiplicity of microneedles, wherein each of the microneedles comprises:
(a) a skin augmentation composition 1700 comprising at least about 25% by weight of at least one biocompatible skin augmenting material, and at least about 1% by weight of at least one biocompatible dispersant, which disperses the skin augmenting material upon contact with the dermis layer or hypodermis layer; and
(b) a skeleton made of a rigid material, the skeleton comprises:
i. a base section 1130 on one end of the skeleton; in certain embodiments, the base section having a height of at least about 30 µm; in certain embodiments, the base section substantially devoid of a skin augmenting material;

ii. a middle section 1110 connected to the base section on one end; in certain embodiments, the middle section having a height of between about 35 µm to about 2500 µm; the middle section configured to temporarily accommodate the skin augmentation composition; in certain embodiments, the middle section and the skin augmentation composition are configured to at least partly expose the skin augmentation composition to the outer surface of the microneedle; and iii. a sharp tip section 1120 connected to the middle section on one end and configured to penetrate human facial or neck skin; in certain embodiments, the base 1121 of the tip having a cross-section area same or larger than the cross-section area of the middle section; in certain embodiments, the tip section substantially devoid of a skin augmenting material.

In certain embodiments, the skin augmentation composition is solid or semi-solid at room temperature.

In certain embodiments, the term "skin augmentation" refers to increasing the volume of the treated skin and/or skin layer. In certain embodiments, the term "skin augmentation" refers to increasing the apparent volume of the treated skin.

As used herein, the term "strip" refers to a longitudinal shape having a first end and a second end. In certain embodiments, the applicator comprises a first surface intended for being proximal to the skin and a second surface facing away from the skin. As used herein, the term "proximal" refers to a side which is close to the skin of a subject. As used herein, the term "proximal side" and "proximal part" are interchangeable. In certain embodiments, the terms "the proximal surface", "the surface intended for being placed proximal to the skin of a subject" and "the inner surface" are used interchangeably. As used herein, the terms "patient" and "subject" are used interchangeably.

In certain embodiments, the microneedles are located on at least part of the proximal surface of the applicator. In certain embodiments, at least part of the proximal surface of the substrate comprises an adhesive material (as demonstrated on FIG. 13, 1330), configured to be temporarily attached to the subject's skin. In certain embodiments, the microneedles are not co-localized with the adhesive on the proximal surface of the substrate. In certain embodiments, the microneedles are co-localized with the adhesive on the proximal surface of the substrate, for better temporary attachment of the microneedles to the skin. In certain embodiments, the microneedles are at least partially co-localized with the adhesive on the proximal surface of the applicator. As used herein, the term "co-localized" refers to being situated at the same two-dimensional coordinates.

In certain embodiments, the applicator's substrate 1310 is flexible. In certain embodiments, the applicator is adaptable to the outlines of a skin, which require augmentation. In a non-limiting example, the applicator of the provided invention can be applied to a subject's face such that it adapts to the outlines and contours of the face or neck. In certain embodiments, the method further comprises the step of applying the flexible applicator 1300 to a subject's face or neck, such that the applicator adapts to the outline of the face or neck and enables efficient delivery of the skin augmentation composition to the desired site. In certain embodiments, the applicator is curved (not shown). In certain embodiments, the applicator is curved so as to fit to the contours of a skin, which require augmentation. In certain embodiments, the applicator's substrate can be cut as needed to fit to the length of the treated area.

Figure 14:
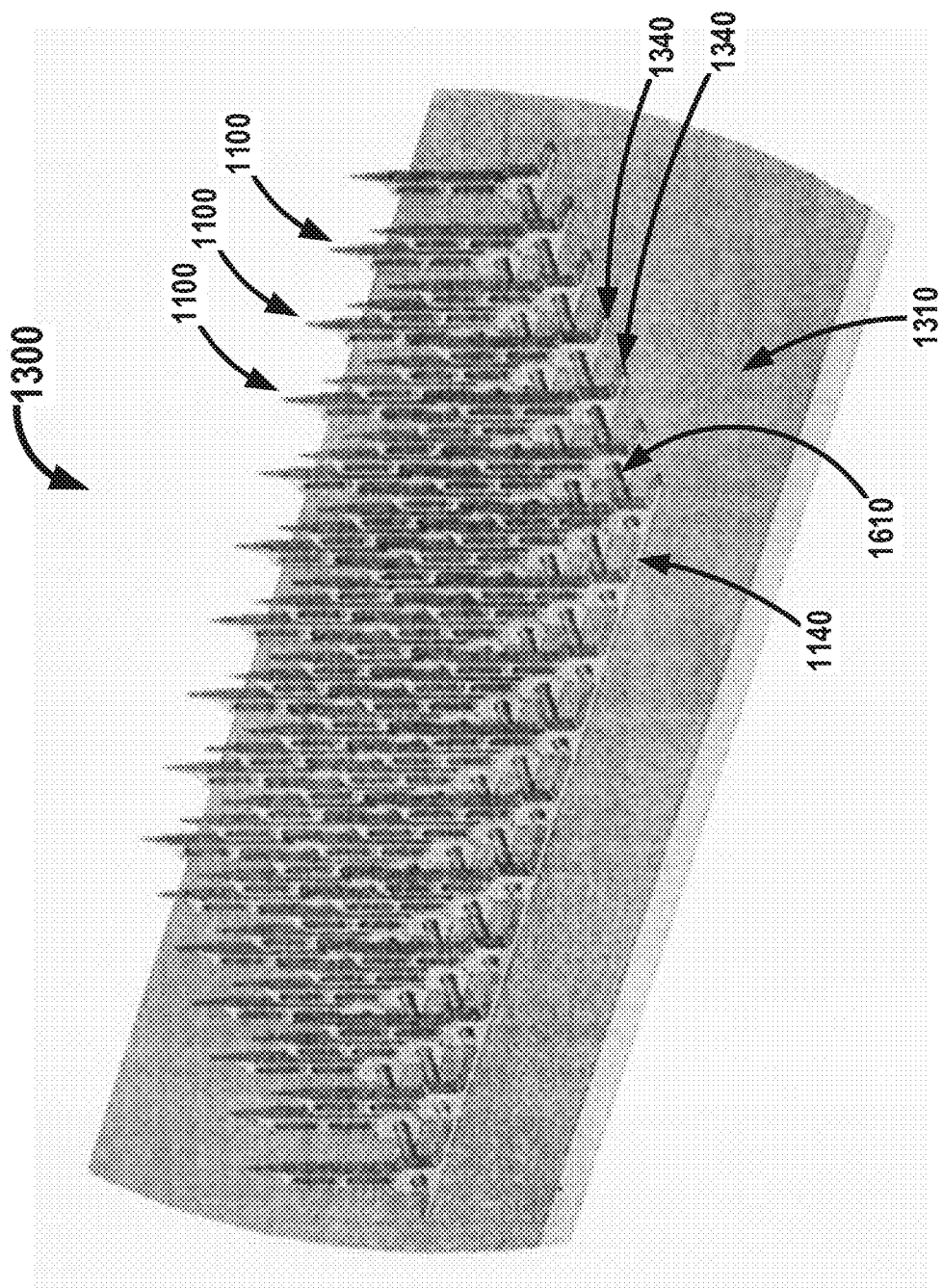
FIG. 14 schematically demonstrates an applicator, including an array of multiple identical microneedles, according to some embodiments of the invention.

In certain embodiments, the applicator comprises a plurality of segments 1340, as demonstrated in FIG. 14. In certain embodiments, the segments are configured to flexibly move one relative to one another. In certain embodiments, each segment comprises a row or an array of microneedles 1100, each comprising the skin augmentation composition. In certain embodiments, each segment 1340 comprises its own substrate thereby allowing the flexible motion one relative to one another. According to other embodiments, the applicator comprises a plurality of segments and a single array of microneedles. In certain embodiments, the segments are attached to one another. In certain embodiments, an applicator comprising a plurality of segments configured to flexibly move relative to one another enables precise placement of the applicator over the subject's undesired lines, wrinkles, depressed scars or folds, which are to be treated. In certain embodiments, the size and/or number of the segments varies so as to enable precise placement of the applicator over the lines, wrinkles, depressed scars or folds to be treated. In certain embodiments, the applicator comprises segments of different sizes.

In certain embodiments, the applicator is made of relatively flexible material to enable precise placement of the applicator over the lines, wrinkles, depressed scars or folds to be treated.

As used herein, the terms "a plurality of" and "a multiplicity of" are used interchangeably and refer to at least two. As used herein, the terms "made of" and "composed of" are used interchangeably.

In certain embodiments, the applicator 1200,1300 further comprises a removable shield or cover or sheath (not shown), configured to protect the microneedles prior to insertion into the facial or neck skin of a subject.

In certain embodiments, the applicator can be provided with any shape and size. In certain embodiments, the substrate can be provided with any shape and size. According to other embodiments, the applicator comprises a shape and size enabling efficient delivery of a skin augmentation composition to a subject in need thereof. In certain embodiments, the applicator comprises a shape and size, which fit treatment areas on a subject. Non-limiting examples are strips, which are configured to fit longitudinal lines or wrinkles, and patches, which are configured to fit larger skin folds, depressed scars or defects to be treated.

According to other embodiments, different applicators, are configured to comprise different amounts of skin augmentation composition. In certain embodiments, different microneedles within the same applicator comprise a different amount of skin augmentation composition. According to other embodiments, different applicators of the invention can comprise different numbers of microneedles. In certain embodiments, the microneedles comprised in the applicators of the inventions can be arranged in different conformations. In certain embodiments, the microneedles comprised in the applicators of the invention can be of different sizes. In certain embodiments, the microneedles comprised in the applicator of the invention are arranged as a single array. In certain embodiments, the microneedles comprised in the applicator of the invention are arranged as multiple arrays. In certain embodiments, the microneedles comprised in the applicator of the invention are arranged as multiple arrays, wherein each array is comprised in a different segment of the applicator. In certain embodiments, the spacing between each two microneedles in a microneedles array is selected between 0.1-2.5 mm. In certain embodiments, the spacing between each two microneedles in a microneedles' array is at least 0.1, 0.2, 0.3, 0.4, 0.5, 0.6, 0.7, 0.8, 0.9, 1, 1.2, 1.4, 1.6, 1.8, 2, 2.2, or 2.5 mm. In certain embodiments, the spacing between each two microneedles in the same microneedles array is at least a spacing, which enables flexibility of the applicator of the invention and/or adaptability of the applicator to the outlines of a skin, which require augmentation.

As used herein, the term "biodegradable" refers to a material which is naturally degraded when in a subject's body, by enzymatic activity, chemical dissolution or otherwise. As used herein, the term "biocompatible" refers to a material, which does not elicit any undesirable and/or toxic local or systemic effects when administered to a subject.

In certain embodiments, the applicator and/or substrate can be provided with any material known in the art, as long as it is able to support microneedles. In certain embodiments, the substrate is made of a non-biodegradable material. In certain embodiments, the substrate is made of a rigid material. Non-limiting examples of materials suitable for making the substrate are: a metal, a polymer, medical plastic, a rubber, latex or a combination thereof. In certain embodiments, suitable polymers for making the applicator include, for instance, polyethylene terephthalate, polyvinylchloride, polyethylene, polypropylene, polycarbonate, polyester, and so forth. In certain embodiments, at least part of the substrate is made of a rigid material. In certain embodiments, at least part of the substrate is made of a flexible material.

In certain embodiments, the substrate 1310 and the base 1130 of the microneedles are made of a non-biodegradable material. As used herein, the base of the microneedle refers to the base of the microneedle's skeleton. In certain embodiments, the skeleton of the microneedles and at least part of the substrate are made of a non-biodegradable material. In certain embodiments the base of the microneedles and at least part of the substrate are made of a unitary piece of a non-biodegradable material. In certain embodiments, the skeleton of the microneedles and at least part of the substrate are made of a unitary piece of a non-biodegradable material. In certain embodiments, the skeleton of the microneedle is attached to the substrate. In certain embodiments, the skeleton of the microneedle is attached to the surface of the substrate intended for being placed proximal to the skin of a subject. In certain embodiments, the skeleton of the microneedle is at least partly inserted into the substrate.

In certain embodiments, the middle section of the microneedle's skeleton passes through a tight-fitting opening in the skeleton's base and is at least partly inserted into the substrate or the substrate surface intended for being placed proximal to the skin of a subject. In certain embodiments, the middle section of the microneedle's skeleton passes through a tight-fitting opening in the skeleton's base and is at least partly inserted into the substrate or the substrate surface intended for being placed proximal to the skin of a subject, such that the middle section is perpendicular to the base and the substrate. In certain embodiments, the base section, the middle section and the tip section of the microneedle's skeleton and are made of one piece. In certain embodiments, the middle section 1110, the tip section 1120, the base section 1130 and the substrate 1210 and are made of one piece, as demonstrated for example in FIGS. 11A-11D and 12.

In certain embodiments, the middle part of the microneedle is the part of the microneedle comprised in between the sharp tip section of the microneedle's skeleton and the base of the microneedle's skeleton, comprising the middle section of the microneedle's skeleton and the augmentation composition.

In certain embodiments, the applicator is configured to be applied by a medical professional. In certain embodiments, the applicator is configured for self-application. It is accordingly to be understood that a subject may be able to use the applicator and methods of the invention without the help of a trained medical professional. In certain embodiments, the applicator is disposable after a single use. In certain embodiments, following removal of the applicator from the skin of the subject, the applicator is substantially devoid of blood or other bio-hazardous substances, following the use of the applicator. As used herein "substantially devoid" is devoid other than trace amounts of other material(s).

In certain embodiments, at least part of the applicator is substantially transparent. In certain embodiments, at least part of the substrate is substantially transparent, as demonstrated 1320 in FIG. 13. In certain embodiments, only the part of the applicator comprising the microneedles is substantially transparent. In certain embodiments, only the part of the substrate comprising the microneedles is substantially transparent. In certain embodiments, at least the part of the substrate not comprising an adhesive surface is substantially transparent. As used herein. "substantially transparent" refers to a material having an opacity level which enables seeing the skin to be treated through the material. In certain embodiments, using an applicator comprising a substrate, which is substantially transparent, according to the present invention, enables a care giver to see the site and the direction of skin defect or deficiency through the applicator and thus enables accurate placement of the applicator. In certain embodiments, at least part of the substrate and/or at least part of the microneedles are substantially transparent.

In certain embodiments, at least part of each microneedle is substantially transparent. In certain embodiments, at least part of the microneedle's skeleton is substantially transparent. In certain embodiments, the microneedle's skeleton is substantially transparent. In certain embodiments, at least the base of the microneedles is substantially transparent. In certain embodiments, at least the base of the microneedles and a part of the substrate are substantially transparent. In certain embodiments, at least part of the substrate is substantially transparent, and the microneedles are not substantially transparent. In certain embodiments, clearly visible microneedles, which are not substantially transparent, comprised in a substantially transparent substrate according to the invention, assist in placing the applicator accurately over the site of skin defect or deficiency.

In certain embodiments, the applicator further comprises a marking (not shown), configured for indicating the location of the array of microneedles on the substrate, for a none limiting example a ruler like marking. In certain embodiments, the marking indicates the location of the array of microneedles on the substrate is on the surface of the substrate facing away from the skin. In certain embodiments, the marking indicates the location of the array of microneedles on the substrate is on the surface proximal to the skin. In certain embodiments, the marking indicates the location of the array of microneedles on the substrate is both on the surface of the substrate facing away from the skin and the surface of the substrate proximal to the skin. In certain embodiments, the marking is in the form of dots, lines or the like, each dot representing the location of a single microneedle in the microneedle array. In certain embodiments, the marking delineates the general location of the entire microneedle array on the substrate. In certain embodiments, the marking indicates the location of the array of microneedles on the substrate assists in accurately placing the applicator over the site of skin defect or deficiency, thus delivering the skin augmentation composition to the exact site of skin defect or deficiency.

Non-limiting examples of a skin defect or deficiency, in certain embodiments of the present invention, are selected from the group consisting of: undesired lines, wrinkles, folds, depressed scars, areas of skin or sub cutis deficiency or a combination thereof.

As used herein, the terms "composition", "the composition of the invention" "augmentation composition", "a soft tissue augmentation composition" and "skin augmentation composition" are used interchangeably and refer to a composition comprising at least one biocompatible skin augmentation material. It is to be understood that a skin augmentation composition according to the present invention is suitable for filling of skin, dermal layer, hypodermal layer or a combination thereof.

As used herein, the terms "biocompatible skin augmentation material", "biocompatible soft tissue augmentation material", "biocompatible agent" and "biocompatible material" are used interchangeably. As used herein, the term "biocompatible material" refers to a biocompatible skin augmentation material. In certain embodiments, the biocompatible material is an inorganic ceramic material, such as, but not limited to, hydroxyapatite. In certain embodiments, the biocompatible material is water-insoluble. In certain embodiments, the biocompatible material is a calcium phosphate ceramic material. As used herein, the terms "hydroxyapatite", "hydroxylapatite", "calcium hydroxyapatite" and "calcium hydroxylapatite" are interchangeable. In certain embodiments, hydroxyapatite as used herein further refers to a salt or derivative of hydroxyapatite.

In certain embodiments, the skin augmenting material is at least 95% crystalline. In certain embodiments, the skin augmenting material is at least 95% crystalline by XRD method. In certain embodiments, the skin augmenting material is at least 98% pure. In certain embodiments, the skin augmenting material has a specific weight of 0.45 g/cm$^3$ to 0.65 g/cm$^3$. In certain embodiments, the skin augmenting material has a specific weight of 0.509 g/cm$^3$.

In certain embodiments, the hydroxyapatite is at least 95% crystalline. In certain embodiments, the hydroxyapatite is at least 95% crystalline by XRD method. In certain embodiments, the hydroxyapatite is at least 98% pure. In certain embodiments, the hydroxyapatite has a specific weight of 0.45 g/cm$^3$ to 0.65 g/cm$^3$. In certain embodiments, the hydroxyapatite has a specific weight of 0.509 g/cm$^3$.

A non-limiting example of a skin augmentation composition comprising a biocompatible ceramic material is RADIESSE® manufactured by Merz Aesthetics, comprising calcium hydroxylapatite beads suspended in a gel carrier that consists primarily of water, glycerin and sodium carboxymethylcellulose.

In certain embodiments, a biocompatible material is biodegradable. In certain embodiments, a biocompatible material is capable of undergoing biodegradation not less than 1, 2, 3, 4 weeks following administration to a subject. In certain embodiments, a biocompatible material is capable of undergoing biodegradation not less than 1, 2, 3, 4, 5, 6, 7, 8, 9, 10, 11, 12 months following administration to a subject. In certain embodiments, a biocompatible material is capable of undergoing biodegradation not less than 0.5, 1, 2, 3 years following administration to a subject. In certain embodiments, a biocompatible material is capable of undergoing biodegradation not less than few months following administration to a subject. In certain embodiments, a biocompatible material is capable of undergoing biodegradation not less than 12 months following administration to a subject. In certain embodiments, a biocompatible material is non-biodegradable.

In certain embodiments, the biocompatible material is in the form of beads and/or particles. In certain embodiments, the biocompatible material comprises beads and/or particles having the same or different sizes. In certain embodiments, the biocompatible material is in the form of beads and/or particles of a size suitable for the size of the treated area. In certain embodiments, applicators which contain large beads of a biocompatible material are suitable for treating deep and/or large lines, wrinkles or folds.

In certain embodiments, the biocompatible material comprises beads and/or particles having a size of up to 5, 10, 20, 30, 40, 50, 60, 70, 80, 90 or 100 micrometers (μm). In certain embodiments, the biocompatible material comprises beads and/or particles having a size of 25-45 μm. In certain embodiments, the biocompatible material comprises beads and/or particles having a size of 10-50 μm. In certain embodiments, the biocompatible material comprises beads and/or particles having a size of 5-20 μm. According to certain embodiments, the biocompatible material comprises beads and/or particles having a size of about 40 μm. In certain embodiments, the biocompatible material particles are of about 10-100 μm, preferably of about 40 μm.

In certain embodiments, the skin augmentation composition comprises at least 1, 2, 3, 4, 5, 10, 15, 25, 30, 40, 50, 60, 70, 80, 90 or 95 percent biocompatible material. In certain embodiments, the skin augmentation composition comprises at least 30% biocompatible material.

In certain embodiments, the composition of the invention comprises at least one biocompatible filler, at least one biodegradable carrier and at least one additional skin augmentation material. In certain embodiments, the composition of the invention comprises hydroxyapatite and at least one biodegradable carrier. In certain embodiments, the composition of the invention comprises hydroxyapatite and polyethylene glycol. In certain embodiments, the composition of the invention comprises hydroxyapatite, polyethylene glycol and magnesium sulfate.

In certain embodiments, the biodegradable carrier is selected from the group consisting of: water-soluble polymer, polyethylene glycol (PEG), polyethylene oxide (PEO), polyoxyethylene (POE), glycerin, carboxymethylcellulose, sterile water, magnesium sulfate, salt, and any combination thereof and a combination thereof.

In certain embodiments, the biodegradable carrier is a salt. In certain embodiments, the salt is a water-soluble salt. In certain embodiments, the salt is selected from the group consisting of: sodium sulfate, sodium chloride, magnesium sulfate, magnesium citrate, magnesium chloride and a combination thereof.

In certain embodiments, the biodegradable carrier is a biodegradable polymer. In certain embodiments, the biodegradable polymer is a polymer selected from the group consisting of: Polyethylene glycol (PEG), Polyglactin 910, Polyglecaprone 25, Polydioxanone, Lactomer 9-1, Glycomer 631, Polyglyconate and combinations thereof. In certain embodiments, the biodegradable carrier is magnesium sulfate and/or polyethylene glycol. In certain embodiments, PEG as used herein has a molecular weight between 10 and 50 kDa. In certain embodiments, a biodegradable carrier comprising PEG of 10-50 kDa has a thick paste consistency. In certain embodiments, the biodegradable carrier is Polyglactin 910 and/or magnesium sulfate.

In certain embodiments, the biodegradable carrier is degradable within 1, 2, 3, 4, 5, 6, 7, 8, 9, 10, 12 hours of inserting the microneedles into the skin of a subject. In certain embodiments, the biodegradable polymer is degradable within 1, 2, 3, 4, 5, 6, 7, 8, 9, 10, 12 hours of inserting the microneedles into the skin of a subject. In certain embodiments, the biodegradable carrier is degradable within 0.5, 1, 2, 3, 4, 5, 6, 7 days of inserting the microneedles into the skin of a subject. In certain embodiments, the biodegradable polymer is degradable within 0.5, 1, 2, 3, 4, 5, 6, 7 days of inserting the microneedles into the skin of a subject. In certain embodiments, the biodegradable carrier undergoes biodegradation within less than 7 days of inserting the microneedles into the skin of a subject, preferably less than 2 days, most preferably less than 1 day. In certain embodiments, rapid biodegradation of the biodegradable carrier within hours/days of introduction into the body of a subject results in uniform distribution of the biocompatible filler material and/or the skin augmentation material in the treated area, thus achieving uniform filing of the treated skin defect/deficiency. In certain embodiments, following insertion of the composition of the invention to the skin of the subject, the biodegradable carrier undergoes biodegradation and the biocompatible filler remains within the skin of a subject for at least several months, preferably up to a year, most preferably more than a year.

In certain embodiments, insertion of microneedles comprising the skin augmentation composition to the skin of a subject results in biodegradation of fast-degrading elements in the composition, thus resulting in release of the biocompatible filler into the treated area. In certain embodiments, the fast-degrading element is a biodegradable carrier such as, but not limited to, magnesium sulphate and/or polyethylene glycol. It is to be understood that, in certain embodiments, biodegradation of elements in the composition such as a biodegradable carrier assist in homogenous spreading of the biocompatible filler in the treated area. In certain embodiments, following biodegradation of fast-degrading elements, such as a biodegradable carrier, the biocompatible filler is transferred from the microneedle to the treated area. As used herein, fast-degrading elements refer to elements within the composition of the invention which undergo biodegradation within hours or up to 7 days from insertion of the microneedles of the invention into the skin of a subject. It is to be understood that a biocompatible filler is not a fast-degrading element of the composition of the invention. In certain embodiments, following administration of the applicator of the invention for a desired period of time, the applicator and the microneedles are removed from the subject, while at least part of the composition remains in the treated area.

In certain embodiments, the biodegradable carrier comprises water and/or carboxymethylcellulose and/or glycerin. In certain embodiments, the biodegradable carrier comprises water, glycerol and carboxymethylcellulose. In certain embodiments, the biodegradable carrier comprises carboxymethylcellulose.

In certain embodiments, the composition of the invention comprises a biocompatible filler material in the form of beads and/or particles surrounded by at least one biodegradable carrier. In certain embodiments, the composition of the invention comprises a biocompatible filler material in the form of beads and/or particles surrounded by at least one biodegradable polymer and/or glycerin and/or carboxymethylcellulose and/or water. In certain embodiments, the composition of the invention comprises a biocompatible filler material in the form of beads and/or particles surrounded by at least one salt. In certain embodiments, the composition of the invention comprises hydroxyapatite in the form of beads and/or particles surrounded by at least one biodegradable carrier.

In certain embodiments, beads or particles of a biocompatible filler material such as, but not limited to, hydroxyapatite, surrounded by a biodegradable carrier, homogeneously spread in the treated area upon degradation of the biodegradable carrier by dissolution, enzymatic activity and the like.

In certain embodiments, adding a biodegradable polymer to the composition of the invention results in a composition having a gel, a paste or a solid like consistency. In certain embodiments, adding carboxymethylcellulose to the composition of the invention results in a composition having a gel, a paste or a solid like consistency. In certain embodiments, a gel, a paste or a solid like composition is configured to be easily inserted into and kept in the middle part of the microneedles of the invention. In certain embodiments, addition of a salt to the composition of the invention assists in uniform dispersion of the biocompatible filler within the composition. In certain embodiments, an addition of a material that attracts water or water solution, like: glycerin, or salt, or polyethylene glycol (PEG), and other such materials or compounds, to the composition of the invention, results in water diffusion into the composition, thus assisting in uniform dispersion of the biocompatible filler within the composition and/or within the treated area.

As used herein, the terms "skin augmentation material" and "filler" refer to agents and compositions useful for augmentation of skin defects. In certain embodiments, a skin augmentation material is a dermal and/or hypodermal filler. Suitable skin augmentation materials according to the invention include, but are not limited to, proteins, polysaccharides, lipids, synthetic polymers and combinations thereof. In certain embodiments, a skin augmentation material according to the invention is any material known in the art which is suitable for filling undesired fold, wrinkle, depressed scar or line in a skin of a subject. In certain embodiments, a skin augmentation material according to the invention is any skin augmentation material which is configured to be delivered using microneedles. In certain embodiments, a biocompatible filler material is a skin augmentation material. According to certain embodiments, a skin augmentation material refers to a biocompatible, inert material. The term "Inert material" as used herein refers to a non-antigenic, non-carcinogenic, non-teratogenic, and non-migratory augmentation material.

In certain embodiments, skin augmentation materials include allogeneic products, xenogeneic products and synthetically derived products.

In certain embodiments, the composition of the invention further comprises at least one skin augmentation material selected from the group consisting of: a biodegradable natural substance, a biodegradable synthetic polymer, a non-biodegradable synthetic polymer, a non-biodegradable natural substance and combinations thereof.

In certain embodiments, a biodegradable natural substance is selected for example from the group consisting of: bovine collagen, porcine collagen, recombinant collagen, human collagen, gelatin, hyaluronic acid, hyaluronic acid derivative (in a liquid, semi-solid and solid states), dried acellular particulate dermal matrix, allogeneic fat and combinations thereof.

In certain embodiments, a biodegradable synthetic polymer is selected for example from the group consisting of:

poly-L-lactic acid, polyethylene oxide, carboxymethylcellulose and combinations thereof.

In certain embodiments, a non-biodegradable synthetic polymers is selected for example from the group consisting of: polymethyl methacrylate (PMMA), polymethyl methacrylate beads, silicones, silicone rubber, expanded polytetrafluoroethylene (ePTFE), polyacrylamide, polyalkylimide and combinations thereof.

In certain embodiments, the skin augmentation composition comprises at least one biocompatible filler material, a biodegradable carrier and at least one type of skin augmentation material selected from the group consisting of: a biodegradable natural substance, a biodegradable synthetic polymer, a non-biodegradable synthetic polymer and combinations thereof.

In certain embodiments, the skin augmentation composition comprises hydroxyapatite and at least one type of skin augmentation material other than hydroxyapatite. In certain embodiments, the skin augmentation composition comprises hydroxyapatite and at least one type of soft-tissue augmentation material selected from the group consisting of: a biodegradable natural substance, a biodegradable synthetic polymer, a non-biodegradable synthetic polymer, a non-biodegradable natural substance and combinations thereof. In certain embodiments, the skin augmentation composition comprises hydroxyapatite and at least one type of soft-tissue augmentation material selected from the group consisting of: a biodegradable natural substance, a biodegradable synthetic polymer, a non-biodegradable synthetic polymer and combinations thereof.

In certain embodiments, the composition of the invention comprises less than 50% weight percent water-soluble skin augmentation materials such as, but not limited to, collagen, hyaluronic acid and gelatine.

Skin augmentation materials, which are to be comprised in the composition of the invention are effective dermal fillers approved by the U.S. Food and Drug administration, including but not limited to fillers comprising structural proteins, polysaccharides or synthetic polymers. Exemplary embodiments of skin augmentation materials that are to be used include collagen, such as reconstituted bovine collagen products including, but not limited to, ZYDERM I®, ZYDERM II® and ZYPLAST® (Collagen Corporation); natural human collagen COSMODERM™ and COSMOPLAST™ (INAMED); and endogenous collagen from the subject, AUTOLOGEN® produced by Collagenesis. In certain embodiments, additional examples of dermal fillers can be selected from those comprising hyaluronic acid, including but not limited to, such products as HYLAFORM® gel manufactured by INAMED and Genzyme Corporations, derived from the rooster combs of domestic fowl; and RESTYLANE® manufactured by Medicis, a hyaluronic acid derivative derived from streptococcal bacterial fermentation. Hyaluronic acid according to the present invention includes both non-cross-liked and/or cross-linked hyaluronic acid derivatives as are well known in the art. "Hyaluronic acid", according to the present invention, includes solid and semi solid forms of Hyaluronic acid. In certain embodiments, collagen according to the invention is selected from the group consisting of: allogeneic collagen, xenogeneic collagen and a combination thereof. According to other embodiments, a skin augmentation material is human cadaveric dermis cultivated from a cadaver.

In certain embodiments, the composition of the invention further comprises a biologically active agent. In certain embodiments, the biologically active agent is selected from the group consisting of: an enzyme, a drug, a toxin and a combination thereof. In certain embodiments, the composition of the invention is devoid of any biologically active agents.

In certain embodiments the enzyme is collagenase for treating scars or keloids, hyaluronidase to treat Hyaluronic acid excess, or elastase for skin expansion.

In certain embodiments, the drug is an analgesic. In certain embodiments, when the applicator of the invention is used to deliver skin augmentation composition subcutaneously, at least one analgesic is co-delivered by the applicator of the invention together with the skin augmentation composition. In certain embodiments, the skin augmentation composition of the invention further comprises an analgesic. In certain embodiments, the methods of the invention further comprise administration of an analgesic. In certain embodiments, every analgesic known in the art can be used with the present invention, such as, but not limited to: lidocaine, paracetamol, non-steroidal anti-inflammatory drug (NSAID). COX-2 inhibitor, opiates or morphinomimetics. In certain embodiments, an analgesic which can be used with the present invention is lidocaine.

In certain embodiments, the drug is a drug known in the art to assist in filling undesired lines, wrinkles, folds and the like. In certain embodiments, examples of drugs which are suitable to be comprised in the composition of the invention include, but are not limited to, anti-psoriasis drugs, muscle relaxants and a combination thereof.

In certain embodiments, the drug is a drug for treatment or prevention of pathological scarring. In certain embodiments, the drug for treatment of pathological scarring is a corticosteroid. In certain embodiments, the corticosteroid is any corticosteroid known in the art for treatment of pathological scarring, such as, but not limited to triamcinolone.

In certain embodiments, the toxin is botulinum toxin. In certain embodiments, the composition of the invention comprises botulinum toxin. In certain embodiments, the composition of the invention comprises botulinum toxin type A, human albumin and sodium chloride. In certain embodiments, the applicator of the invention comprises botulinum toxin. In certain embodiments, the microneedles for administrating botulinum toxin should be longer to reach the mimics muscles that located under the hypodermis.

In certain embodiments, the skin augmentation composition of the invention further comprises a medical pigment. In certain embodiments, the microneedles of the invention further comprise a medical pigment. As used herein, the term "medical pigment" refers to a color material suitable for insertion into the skin of a subject. In certain embodiments, medical pigments have a regulatory approval for insertion into a skin of a subject. In certain embodiments, medical pigments are pigments known in the art to be suitable for micro-pigmentation treatments. In non-limiting examples, medical pigments suitable for use according to the present invention include, but are not limited to, pigments such as BIOCHROMADERM® (Biotic Phocea) or the Signature Series (Micro-Pigmentation Centre, Inc.). In certain embodiments, possible medical pigments for use with the applicator of the present invention can be selected from: pigments for scar camouflage, areola reconstruction, lip remodeling and any combination thereof.

In certain embodiments, a microneedle comprising a medical pigment is suitable for micro-pigmentation treatments. In certain embodiment, micro-pigmentation treatments are selected from the group consisting of: concealment of scars, concealment and/or blurring of skin pigmentation, nipple areola construction and/or augmentation, correction of freckles, lip coloring, eyebrow coloring and a combination thereof. In certain embodiments, the microneedles of the invention comprise a composition comprising a medical pigment. In certain embodiments, the applicator of the invention further comprises microneedles comprising a medical pigment without a biocompatible filler or a skin augmentation composition.

In certain embodiments of the invention, an array of microneedles can include one row of microneedles or more. In certain embodiments, an array of microneedles can include a mixture of microneedles having, for example, various lengths, diameters, cross-sectional shapes, and spacing between the microneedles. In certain embodiments, the length (L) of the microneedles of the invention is between about 0.05 and 2.5 mm, preferably between 100 μm and 500 μm, and more preferably between 60 and 2500 μm. In certain embodiments, the length of the microneedles is selected according to the particular application or treated tissue. For certain applications it is desirable to use microneedles of slightly greater dimensions. Thus, in certain embodiments, the length of the microneedles of the invention is above 1 mm. According to additional embodiments, the length of the microneedles of the invention is up to 7 mm.

In certain embodiments, microneedles longer than 1 mm are used to deliver the skin augmentation composition subcutaneously. In certain embodiments, microneedles are used to deliver the skin augmentation composition to areas having deep wrinkles and/or skin deficiency. In certain embodiments, microneedles longer than 1 mm are used to deliver the skin augmentation composition to areas having deep wrinkles and/or skin or sub cutis deficiency.

In certain embodiments, the applicator of the invention comprises microneedles having various lengths (L). In certain embodiments, the applicator of the invention comprises microneedles having variable lengths and/or variable degrees of thickness. In certain embodiments, the applicator of the invention comprises microneedles having variable lengths and/or variable degrees of thickness in correlation to the location of the microneedles on the substrate. In certain embodiments, the applicator of the invention comprises microneedles having variable lengths and thicknesses in correlation to the location in which they are configured to be situated within the area to be treated.

In certain embodiments, microneedles configured to be situated at a deeper point of a line, wrinkle or fold to be treated are longer than microneedles configured to be situated at a superficial point of the line, wrinkle or fold to be treated. In a non-limiting example, microneedles configured to be situated closer to the margins of a line, wrinkle or fold to be treated are shorter than microneedles configured to be situated in the center of the line, wrinkle or fold to be treated. In certain embodiments, microneedles situated at the center of the microneedle array are longer than microneedles situated near the margins of the microneedle array. In certain embodiments an applicator comprising microneedles having variable lengths is able to more precisely and uniformly fill a line, wrinkle or fold.

In certain embodiments, the applicator of the invention comprises microneedles having variable degrees of thickness in correlation to the location in which they are configured to be situated within the area to be treated. In certain embodiments, microneedles configured to be situated at a deeper point of a line, wrinkle or fold to be treated are thicker than microneedles configured to be situated at a superficial point of the line, wrinkle or fold to be treated.

As used herein, the term "microneedles" refers, in certain embodiments, to protruding structures designed to pierce the skin and facilitate delivery of various types of compounds.

In certain embodiments, microneedles facilitate delivery of the composition of the invention to dermal and/or hypodermal compartments of the skin. In certain embodiments, subcutaneous delivery of a skin augmentation composition can be achieved by the applicator of the invention if the microneedles comprised in the applicator are longer than the thickness of the skin to be treated. In certain embodiments, the length of the microneedles comprised in the applicator of the invention is configured to allow dermal and/or subcutaneous delivery of a skin augmentation composition.

In certain embodiments, the length of the microneedles comprised in the applicator of the invention is configured to allow delivery of skin augmentation composition to the dermis and/or lower layers of the skin. In certain embodiments, the microneedles comprised in the applicator of the invention are configured to allow delivery of a skin augmentation composition to the dermis and/or lower layers of the skin without delivery of skin augmentation composition to the epidermis layer of the skin. In certain embodiments, the length of the microneedles comprised in the applicator of the invention is configured not to allow delivery of skin augmentation composition to the epidermis. In certain embodiments, the length of the microneedle base is configured not to allow delivery of a skin augmentation composition to the epidermis layer of the skin. In certain embodiments, the length of the microneedle base is configured to allow delivery of a skin augmentation composition exactly in the histological level needed. In certain embodiments, long microneedles enable delivery of skin augmentation composition to subcutaneously and/or to deep layers of the skin, such as, but not limited to, the hypodermis.

In certain embodiments, the rigid material is biocompatible. In certain embodiments, the rigid material is biodegradable. In certain embodiments, the rigid material is rigid as to enable the microneedles to be propelled into the skin of the subject. In certain embodiments, the metal is selected from the group consisting of: stainless steel, titanium, iron, gold, silver, platinum and a combination and/or alloy thereof. In certain embodiments, rigid material is preferably a material approved by the US Food and Drug Association (FDA) for implantation and/or parenteral delivery.

In certain embodiments, the skeleton of the microneedles is removed from the subject upon removal of the applicator from the subject. In certain embodiments, upon removal of the applicator of the invention from the skin of the subject the skeletons of the microneedles are removed while at least part of the composition of the invention remains within the skin or subcutaneous region of the subject's skin. In certain embodiments, upon removal of the applicator of the invention from the skin of the subject at least part of the biocompatible filler remains within the skin or subcutaneous region of the subject's skin, while the microneedles' skeletons are removed.

In certain embodiments, the skeleton of each microneedle comprises a sharp tip section 1120, a base section 1130 and a middle section 1110 connecting the sharp tip section and the base section. As used herein, the terms "sharp tip section", "tip section" and "tip" are used interchangeably. In certain embodiments, the tip section, the base and the middle section of the skeleton are made of a unitary piece of material.

In certain embodiments, the sharp tip section of the microneedle's skeleton is the most proximal part of the microneedle. As used herein, the proximal side of the microneedle refers to the microneedle's side, which is closest to the subject and farthest from the substrate of the applicator. The base section part 1130 and the sharp tip section 1120 of the microneedle's skeleton are on opposing ends of the microneedle's skeleton. As used herein, the base section 1130 of the microneedle refers to the side of the microneedle which is farthest from the subject and closest to the substrate's surface intended for being placed proximal to the skin of a subject. In certain embodiments, the base section of the microneedle's skeleton is the base of the microneedle 1100.

In certain embodiments, the sharp tip section of the microneedle's skeleton is configured to penetrate the skin of a subject. In certain embodiments, the sharp tip section is of any shape, which enables it to penetrate the skin of a subject.

In certain embodiments, the base diameter or base cross-section area 1121 of the sharp tip section is larger than the diameter or cross-section area of the middle section 1110, with the skin augmentation composition (respectively). In certain embodiments, the base diameter or base cross-section area 1121 of the sharp tip section 1120 is same as the diameter or cross-section area of the middle section with skin augmentation composition. In certain embodiments, the base diameter or base cross-section area of the sharp tip section is larger than the diameter or base cross-section area of the microneedle's middle section 1110. In certain embodiments, the largest diameter or largest cross-section area of the sharp tip section 1120 is larger than the largest diameter or cross-section area of the middle section 1110, including the skin augmentation composition. In certain embodiments, the largest diameter or cross-section area of the sharp tip section 1120 is larger than the largest diameter or cross-section area of the microneedle's middle section 1110. In certain embodiments, they have the same diameter or cross-section area. As used herein, the base 1121 diameter of the sharp tip section refers, in certain embodiments, to the largest distance that can be formed between two opposite parallel lines tangent to the boundary of a cross section area through the sharp tip section, wherein the cross-section is parallel to the substrate. In certain embodiments, the middle section of the microneedle comprises the middle section of the microneedle's skeleton and the augmentation composition.

In certain embodiments, the sharp tip section 1120 punctures the skin of the subject enabling the insertion of the skin augmentation composition. In certain embodiments, a base 1121 of a sharp tip section 1120 having a diameter or cross-section area larger than the diameter or cross section area of the middle section having 1110 and the skin augmentation composition, enables the formation of a skin puncture large enough for the skin augmentation composition to enter into the skin without spillage of the composition outside the body or within the epidermis.

In certain embodiments, the skeleton's base section 1130 is configured to confer stability to the microneedle. In certain embodiments, the base section of the microneedle is configured to prevent the skin augmentation composition from being delivered to the epidermis.

In certain embodiments, the microneedle's base section 1130 is attached to the substrate 1210,1310. In certain embodiments, the microneedle's base section is attached to the substrate's surface intended for being placed proximal to the skin of a subject. In certain embodiments, the microneedle's base section and the substrate are made of a unitary piece of material. In certain embodiments, the microneedle's base section and the substrate's surface intended for being placed proximal to the skin of a subject are made of a unitary piece of material.

In certain embodiments, the length (b) of the base section 1130 is equal or higher than the thickness of the epidermis at a treated area. In certain embodiments, a base section having a length equal or higher than the thickness of the epidermis at the treated area, prevents delivery of the skin augmentation composition to the epidermis. In certain embodiments, preventing a delivery of a skin augmentation composition to the epidermis prevents wasting material, enhance the augmentation effect of the composition or prevent inflammation and/or infection of the treated site.

According to certain embodiments, the length ($L_b$) of the base section 1130 is equal or higher than the combined thickness of the epidermis and dermis of the treated area. In certain embodiments, microneedles having a base section at least as long as the combined thickness of the epidermis and dermis of the treated area are configured to prevent delivery of the skin augmentation composition to the dermis and the epidermis. In certain embodiments, microneedles having a base section at least as long as the combined thickness of the epidermis and dermis of the treated area are configured to deliver the skin augmentation composition subcutaneously or into the hypodermis. In certain embodiments, varying the length of the base section determines the depths of the skin and/or subcutaneous layer into which the composition is delivered.

In certain embodiments, all the microneedles on the same applicator have the same base section 1130 length ($L_b$). In certain embodiments, the applicator of the invention comprises microneedles having variable base section lengths. In certain embodiments, the length ($L_b$) of the base section 1130 is variable in correlation to the location in which each microneedle is configured to be situated at within a treated area. In certain embodiments, the applicator of the invention comprises microneedles having variable base section lengths in correlation to the location of the microneedles on the substrate. In certain embodiments, the applicator of the invention comprises microneedles having variable base section lengths in correlation to the thickness of the epidermis and/or dermis at the location each microneedle is configured to be positioned at. In certain embodiments, the applicator of the invention comprises microneedles having variable lengths in correlation to the location in which they are configured to be situated within the area to be treated.

In certain embodiments, microneedles configured to be placed at a treatment area having a thick epidermis have a longer base section 1130 than microneedles configured to be placed at a treatment area having a thin epidermis. It is to be noted that, in certain embodiments, an applicator configured to be placed on a treated area having an epidermis and/or dermis with varying thickness levels comprises microneedles having base sections of varying lengths corresponding to the varying thickness levels.

In certain embodiments, microneedles located at the center of a microneedle array comprise a longer base section 1130 than microneedles located near the edges of the microneedle array. In certain embodiments, microneedles configured to be situated closer to the margins of a line, wrinkle or fold to be treated are comprise a shorter base section than microneedles configured to be situated in the center of the line, wrinkle or fold to be treated. In certain embodiments, a microneedle having a long base section is configured to deliver the skin augmentation composition to a deeper skin or subcutaneous layer than a microneedle having a short base section.

In certain embodiments, a diameter or cross-section area of the base section 1130 is smaller than a diameter or cross section area of the sharp tip section 1120 (respectively). In certain embodiments, the largest diameter or cross-section area of the base section 1130 is smaller than the largest diameter or cross section area of the sharp tip section 1120. In certain embodiments, the diameter or cross-section area of the base section 1130 is equal to the diameter or cross-section area of the middle section 1110 including the skin augmentation composition. In certain embodiments, the diameter or cross-section area of the base section 1130 is equal to the diameter or cross-section area of the microneedle's middle part 1110. As used herein, the diameter of the base section refers, in certain embodiments, to the largest distance that can be formed between two opposite parallel lines tangent to the boundary of a cross section through the base section 1130 of the microneedle 1100, wherein the cross-section is parallel to the substrate.

In certain embodiments, the middle section 1110 of the microneedle skeleton is provided with any form suitable for providing the microneedle with rigidity and providing support for the skin augmentation composition. In certain embodiment, the middle section 1110 of the skeleton is in the form of a longitudinal core extending substantially from the center of the sharp tip section 1120 to the center of the base section 1130. In certain embodiment, the middle section 1110 of the skeleton comprises a longitudinal core extending substantially from the center of the sharp tip section 1120 to the center of the base section 1130. As used herein, the term "longitudinal core" refers to a longitudinal piece of a rigid, non-biodegradable, compatible material extending substantially through the center of the microneedle middle part. In certain embodiments, the longitudinal core can be provided with any shape, such as, but not limited to, a cone, a cylinder, a pyramid, a rectangular box, a triangular box, a polygonal box and the like. In certain embodiments, the longitudinal core has the same dimensions throughout the length of the microneedle's middle part. In certain embodiments, the skeleton's middle section 1110 extends through the base part 1130 and is at least partly inserted into the substrate. In certain embodiments, the skeleton's middle section extends through the base part and is at least partly inserted into the substrate perpendicularly. In certain embodiments, a skeleton's middle section in the form of a longitudinal core inserted through the base of the skeleton and into the substrate in the form of a cross confers substantial stability to the microneedle. As used herein, the term "extension", "skeleton extension". "middle section extension". "middle part extension" and "microneedle extension" are used interchangeably and relate to an extension of the middle part of the microneedle's skeleton through the base of the skeleton and at least partly into the substrate of the applicator.

In certain embodiments, the skin augmentation composition at least partly surrounds the middle section 1110 of the microneedle's skeleton. In certain embodiments, the skin augmentation composition at least partly surrounds the longitudinal core. In certain embodiments, the skin augmentation composition surrounds the longitudinal core. In certain embodiments, the skin augmentation composition which is accommodated and surrounding the skeleton's middle section can form any shape, such as, but not limited to: a cylinder, a rectangular box, a triangular box, a polygonal box and the like.

As used herein, the diameter of the skin augmentation composition refers, in certain embodiments, to the largest distance that can be formed between two opposite parallel lines tangent to the boundary of a cross section through the middle part of the microneedle, wherein the cross section is parallel to the substrate. In certain embodiments, the diameter of the skin augmentation composition refers to the largest distance that can be formed between two opposite parallel lines tangent to the boundary of a cross section through the skin augmentation composition. In certain embodiments, the diameter of the skin augmentation composition refers to the largest distance that can be formed between two opposite parallel lines tangent to the boundary of a cross section through the skin augmentation composition and middle section of the microneedle's skeleton.

In certain embodiments, the methods of the invention are useful for delivering a skin augmentation composition to a site of skin defect or deficiency. In certain embodiment, the site of skin defect or deficiency is undesired lines, wrinkles folds and the like in the skin of a subject. In certain embodiment, the site of skin defect or deficiency is undesired lines, wrinkles folds and the like in the facial skin of a subject. In certain embodiments, the methods of the invention are useful for filling an undesired fold, wrinkle, line or depressed area in a subject.

As used herein, the terms "placing" and "administering" are used interchangeably and refer to locating the applicator of the invention at a desired site. In certain embodiments, following administration, the microneedles penetrate the treatment area and the composition of the invention is delivered to the target site. In a non-limiting example, placing the applicator over a forehead wrinkle results in insertion of the microneedles to the skin of the subject and delivery of the composition of the invention to the dermal and/or sub-dermal layer. In certain embodiments, following placing the applicator on the skin of a subject, the microneedles penetrate the skin and the biodegradable polymer and/or salt undergo biodegradation, thus releasing the biocompatible filler which remains in the subject following removal of the applicator.

In certain embodiments, the site of skin defect or deficiency is the site of a scar. In certain embodiments, the terms "treated area" and "treatment area" are interchangeable and refer to a site of skin or sub cutis defect or deficiency, or a combination thereof. In certain embodiments, the site of skin or sub cutis defect or deficiency is the site of a depressed scar. In certain embodiments, the methods of the invention are useful in augmentation of scars. According to other embodiments, the methods of the invention are useful in filling skin and/or sub cutis scar tissue. As used herein, the term "normal skin" refers to a healthy skin and/or a young looking skin.

Non-limiting examples of a site of skin or sub cutis defect or deficiency which can be treated by the applicator, in certain embodiments of the invention, comprise: delicate forehead, cheek, neck, nasal-bridge and lip wrinkles, nasolabial folds, marionette lines, depressed scars, lips, area of malar bones and a combination thereof. In certain embodiments, the applicator is configured for treatment of static face areas, such as but not limited to, the forehead.

In certain embodiments, the applicator is placed at a site of skin defect or deficiency or at undesired lines, wrinkles folds for at least 1, 2, 3, 5, 6, 7, 8, 9, 10, 11, or 12 hours. In certain embodiments, the applicator is placed at a site of skin defect or deficiency or at undesired lines, wrinkles folds for at least a full night. As used herein, a full night is between 6-10 hours. In certain embodiments, the applicator is placed at a site of skin defect or deficiency or at undesired lines, wrinkles folds for at least 24 hours. In certain embodiments, the applicator is placed at a site of skin defect or deficiency or at undesired lines, wrinkles folds for at least 1, 2, 3, 5, 6, or 7 days. In certain embodiments, the applicator is placed at a site of skin defect or deficiency or at undesired lines, wrinkles folds for a period of time sufficient for the degradation of the biodegradable carrier. In certain embodiments, the applicator is placed at a site of skin defect or deficiency or at undesired lines, wrinkles folds for 24-72 hours.

In certain embodiments, the skin augmentation composition is a slow-releasing skin augmentation composition. As used herein, the term "slow-releasing skin augmentation composition" refers, in certain embodiments, to a composition configured for slow-release of a skin augmentation material and/or of a drug and/or of a toxin. In a non-limiting example, the applicator of the invention comprising a slow-releasing skin augmentation material is placed on the face of the subject for several days. According to this non-limiting example, the applicator induces slow release and slow delivery of the skin augmentation material, thus achieving a more efficient augmentation of the target site.

In certain embodiments, the subject places the applicator of the invention at a desired site. In certain embodiments, the applicator of the invention remains at a desired site for a desired time period through the use of an adhesive. As used herein, the adhesive is inert, biologically compatible and enables easy removal of the applicator of the invention. In certain embodiments, the adhesive is resistant to water. In certain embodiments, the adhesive is located only on part of the inner surface of the substrate. In certain embodiments, the adhesive is transparent. In certain embodiments, the adhesive is in the skin color. In certain embodiments, the applicator of the invention is resistant to water. In certain embodiments, the applicator is shaped like an adhesive bandage so that it is configured be placed inconspicuously on the subject's face for a desired time. In certain embodiments, the applicator of the invention is configured to be affixed to the treatment area using external fixation aid such as, but not limited to, a bandage, a handkerchief and the like.

In certain embodiments, the applicator is removed following a desired time period. In certain embodiments, the desired time period depends on the types of microneedles and skin augmentation compositions used in the applicator, on the amount of composition used, on the site of treatment, on the desired effect and a combination thereof.

In certain embodiments, the invention provides a kit comprising at least one of the applicators of the invention and instructions for use of the applicator. In certain embodiments, the applicators, methods and kits of the invention are configured to be used by the subject without needing assistance from a medical care giver. In certain embodiments, the applicators, methods and kits of the invention do not require surgical intervention. In certain embodiments, the methods of the invention are used to fill undesired lines, wrinkles, depressed scars and folds in the face of a subject without use of surgical intervention or needles.

In certain embodiments, the method of the invention would have to be repeated several times in order to fill a site of skin defect or deficiency. According to other embodiments, a single use of the applicator of the invention is sufficient to fill a site of skin defect or deficiency. In certain embodiments, the dimensions and/or shape of the site of skin defect or deficiency determine how many times the applicator of the invention would have to be used at the same site of skin defect or deficiency in order to achieve the desired filling. In a non-limiting example, a deep and/or wide and/or irregularly shaped skin defect or deficiency may require several repetitions of the method of the invention and/or several applicators of the invention and/or a longer application time for proper filling of the skin defect or deficiency.

As used herein, the terms "subject", "a subject in need thereof" and "a patient in need thereof" are used interchangeably and refer, in certain embodiments, to a subject in need of skin or sub cutis augmentation or a combination thereof. In certain embodiments, the subject is a subject having undesired lines, wrinkles, and folds such as, but not limited to, elderly people. According to other embodiments, the subject is a subject having a scar in need of augmentation or filling. In a non-limiting example, a subject is a subject having facial wrinkles which he or she would like to have filled for a younger, healthier and fuller looking facial skin. Of note, a subject may have normal looking skin and wish to use the applicator/method of the invention in order achieve an appearance of fuller skin at a desired area, such as, but not limited to, the cheeks and lips.

The term "room temperature" as used herein generally refers, in certain embodiments, to any temperature between 10° C. and 40° C., or alternatively, in certain embodiments, to any temperature between 15° C. and 30° C.

The term "substantially" as used herein refers, in certain embodiments, to the complete or nearly complete extent or degree of an action, characteristic, property, state, structure, item, or result. For example, a composition which is "substantially consists of A and B" would mean that the composition is either completely made of A and B or nearly completely made of A and B, taking into account minute impurities. The exact allowable degree of deviation from absolute completeness depends in some cases on the specific context. However, generally speaking the nearness of completion will be so as to have the same overall result as if absolute and total completion were obtained.

The use of "substantially" is equally applicable when used in a negative connotation to refer, in certain embodiments, to the complete or near complete lack of an action, characteristic, property, state, structure, item, or result. For example, a composition that is "substantially free of A" would either completely lack A, or so nearly completely lack A that the effect would be the same as if it completely lacked A. In other words, a composition that is "substantially free/devoid of" an ingredient or element may still actually contain such item as long as there is no measurable effect thereof.

As used herein, the term "about" is used to provide flexibility to a provided numerical value, by providing that a given value may be "a little above" or "a little below" the provided number. As used herein, the term "about" further refers, in certain embodiments, to ±10%, preferably ±5%, and most preferably ±1% of the mentioned numerical value.

As used herein, the terms "sub cutaneous" and "sub cutis" are used interchangeably. It is to be understood that the applicator and/or the microneedles of the invention are configured for administration of a skin augmentation composition to skin or to sub-cutaneous layers or to a combination thereof. It is to be understood that the methods of the invention provide augmentation or filling of skin or sub cutaneous layers or a combination thereof.

In certain embodiments, the present invention provides a use of the applicator of the invention for augmentation of skin in a subject in need thereof. In certain embodiments, the present invention provides a use of the applicator of the invention for the filling of an undesired fold, wrinkle, line or depressed area in the skin of a subject in need thereof.

As used herein, the term "biocompatible filler soft-tissue augmentation material", "biocompatible filler material" and "biocompatible filler" are used interchangeably.

In certain embodiments, the present invention fills the need for devices for self-administration of a skin augmentation composition, that are highly efficient, easy to use, cause minimal discomfort to the treated subject and do not require a trained medical professional. The devices of the invention are able to provide homogenous augmentation of skin lines, wrinkles, depressed scars and folds, thus resulting in a substantially smooth skin surface that are difficult to obtain through injection or transplantation, especially in fine wrinkles. The methods of use of the microneedles and applicators provided by the present invention are very accurate in delivering exact amounts or volumes of skin augmenting materials into specific skin layers in specific skin contours. Such methods were nor previously possible due to the limited control of prior devices in accurate and controllable delivery.

In certain embodiments, the method of the invention provides filling of an undesired fold, wrinkle, line or depressed area in a skin of a subject or in sub-cutis layers of a subject or in a combination thereof.

In certain embodiments, the biodegradable carrier comprises magnesium sulfate and polyethylene glycol. In certain embodiments, the augmentation composition comprises hydroxyapatite particles, magnesium sulfate and polyethylene glycol. In certain embodiments, the augmentation composition comprises hydroxyapatite particles and polyethylene glycol.

In certain embodiments, a non-biodegradable synthetic polymer is selected for example from the group consisting of: polymethyl methacrylate, polymethyl methacrylate beads, silicones, silicone rubber, expanded polytetrafluoroethylene, polyacrylamide, polyalkylimide and combinations thereof.

In certain embodiments, the substrate is flexible. In certain embodiments, the applicator comprises a plurality of segments, wherein the segments are configured to flexibly move relative to one another. In certain embodiments, each segment comprises a substrate and an array of microneedles. In certain embodiments, the shape of the applicator is adaptable to the outlines of a skin which requires augmentation. In certain embodiments, the substrate is curved.

In certain embodiments, at least a part of each microneedle is substantially composed of the augmentation composition. In certain embodiments, the augmentation composition is within at least a part of each microneedle. In certain embodiments, the microneedles are at least partly coated with the augmentation composition. In certain embodiments, the augmentation composition at least partly surrounds the middle section of the microneedle's skeleton.

In certain embodiments, the skeleton is attached to the surface of the substrate intended for being placed proximal to the skin of a subject. In certain embodiments, the skeleton is at least partly inserted into substrate.

In certain embodiments, the augmentation composition comprises at least 30% biocompatible filler material. In certain embodiments, the skin augmentation composition comprises hydroxyapatite, and polyethylene glycol.

In certain embodiments, the array of microneedles is located on at least a portion of the substrate's surface intended for being placed proximal to the skin of a subject. In certain embodiments, at least part of the substrate's surface intended for being placed proximal to the skin of the subject is an adhesive surface.

In certain embodiments, the applicator is configured for self-application. In certain embodiments, the applicator is disposable after a single use. In certain embodiments, at least part of the applicator is substantially transparent. In certain embodiments, the applicator further comprises a marking indicating the location of the array of microneedles on the substrate.

In certain embodiments, the microneedles are configured for delivery of the augmentation composition. In certain embodiments, the length (L) of the microneedles is from 0.05 mm to 1 mm. According to additional embodiments, the length (L) of the microneedles of the invention is up to 7 mm. In certain embodiments, the length of the microneedles is variable in correlation to the location of the microneedles on the substrate.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

MORE EXAMPLES

Example 4

METHOD: 3 grams of PEG 10000 (solid at room temperature) were warmed for 4 hours at 80° C. 0.5 ml of sodium phosphate monobasic dihydrate solution ($[H_2NaO_4P]=1$ g/ml) were then added. Hydroxyapatite (HA) was added with mixing to the molten PEG. RESULT: only 1 gram of HA could be added to the 3.5 grams of PEG and sodium phosphate.

Example 5

METHOD: 6.5 grams of HA were slowly added to 3 grams of PEG 600 (liquid at room temperature) and 0.5 ml of sodium phosphate solution. Ethanol was also added. The liquid obtained was well mixed. The ethanol was evaporated at room temperature. RESULT: powder-like mixture.

Example 6

METHOD: 1.25 grams of PEG 10000 and 0.25 grams of PEG 15000 were dissolved overnight in ethanol (5 gram total mass PEG+EtOH). 0.25 grams of sodium phosphate and 5 grams of HA were added to the liquid PEG. RESULT: The solid obtained after extraction of the ethanol was too soft and looked like a powder.

Example 7

METHOD: 2.5 grams of PEG 10000 and 0.5 grams of PEG 15000 were dissolved overnight in ethanol (10 gram total mass PEG+EtOH). 0.5 grams of sodium phosphate and 5 grams of HA were to the liquid PEG. RESULT: The white paste had the same consistency as toothpaste. The solid obtained after extraction of the ethanol was hard and had a good homogeneity. The final weight percentage of HA from the solid was 58.8%.

Example 8

METHOD: 3 grams of PEG 12000 were dissolved overnight in ethanol (10 gram total mass PEG+EtOH). 0.5 grams of sodium phosphate and 5 grams of HA were added to the liquid PEG. RESULT: The white paste had the same consistency as toothpaste. The solid obtained after extraction of the ethanol was hard and had a good homogeneity. The final weight percentage of HA from the solid was 58.8%.

Example 9

METHOD: 3 grams of PEG 12000 were dissolved overnight in ethanol (10 gram total mass PEG+EtOH 70%). 5 grams of HA were added to the liquid PEG. The white paste had the same consistency as toothpaste. RESULT: The solid obtained after extraction of the ethanol was hard and had good homogeneity. The final weight percentage of HA from the solid was 62.5%. Good impregnation of the solid on the needles.

Example 10

METHOD: 3 grams of PEG 12000 were dissolved overnight in ethanol (10 gram total mass PEG+EtOH). 0.5 grams of sodium phosphate and 5 grams of HA were added to the liquid PEG. RESULT: The white paste had the same consistency as toothpaste. The solid obtained after extraction of the ethanol was hard and had good homogeneity. The final weight percentage of HA from the solid was 62.5%. The solid filled the spaces in the needles, and had good stability.

Example 11

METHOD: 3 grams of PEG 12000 were dissolved overnight in ethanol (7 gram total mass PEG+EtOH). 0.5 grams of sodium phosphate and 5 grams of HA were added to the liquid PEG. RESULT: The white paste had the same consistency as toothpaste. The solid obtained after extraction of the ethanol was hard and had good homogeneity. The final weight percentage of HA from the solid was 62.5%. Using less solvent gave non-homogenous filling of the solid into the spaces in the needles.

Example 12

METHOD: 3 grams of PEG 12000 were dissolved overnight in 7 grams of ethanol. 5 grams of HA were added to the liquid PEG. RESULT: The final weight percentage of HA from the solid was 62.5%. The product was warmed to 50° C. and spread on the needles.

Example 13

Figure 16A:
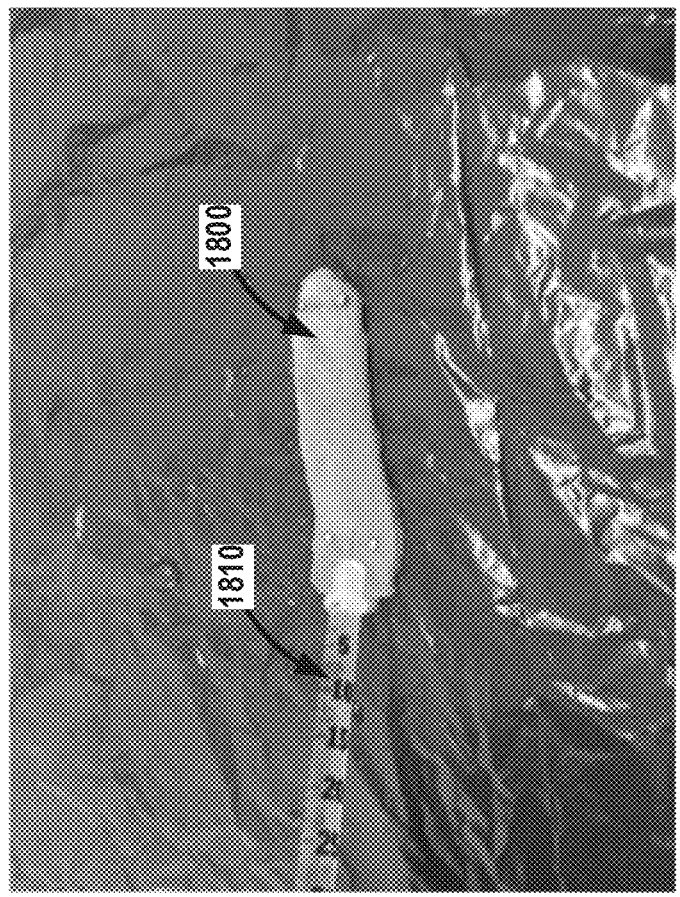
FIG. 16A demonstrates human facial skin pieces used in the skin augmentation experiments described herein, and the lidocaine solution used as local anesthetic to simulate real-life procedures.
Figure 16B:
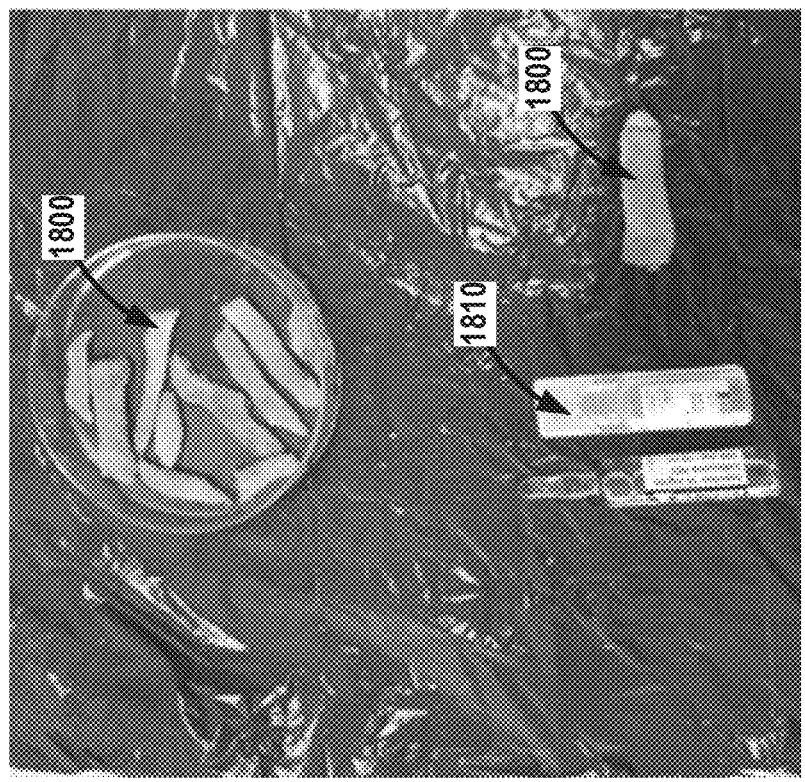
FIG. 16B demonstrates a lidocaine solution being administered to a representative piece of human facial skin.
Figure 17B:
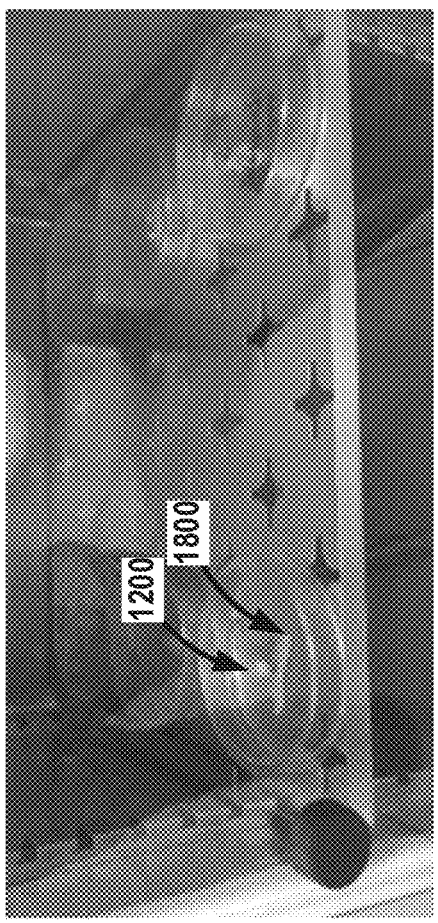
FIG. 17B demonstrates an incubation of the human facial skin pieces at 37° C. and at 88% humidity.
Figure 17A:
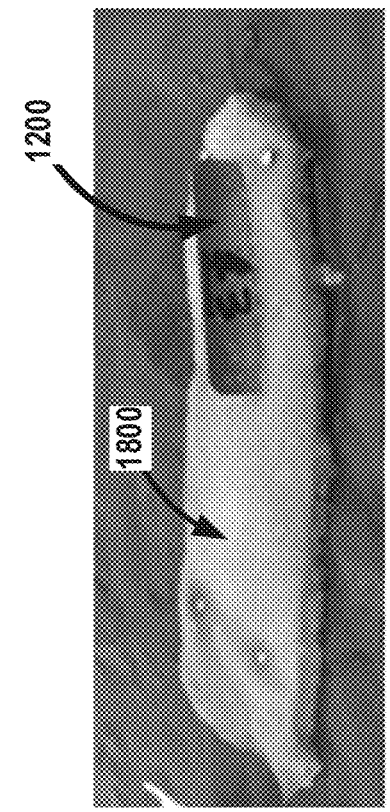
FIG. 17A demonstrates a single line applicator, according to some embodiments of the invention, attached to a representative piece of human facial skin.
Figure 18:
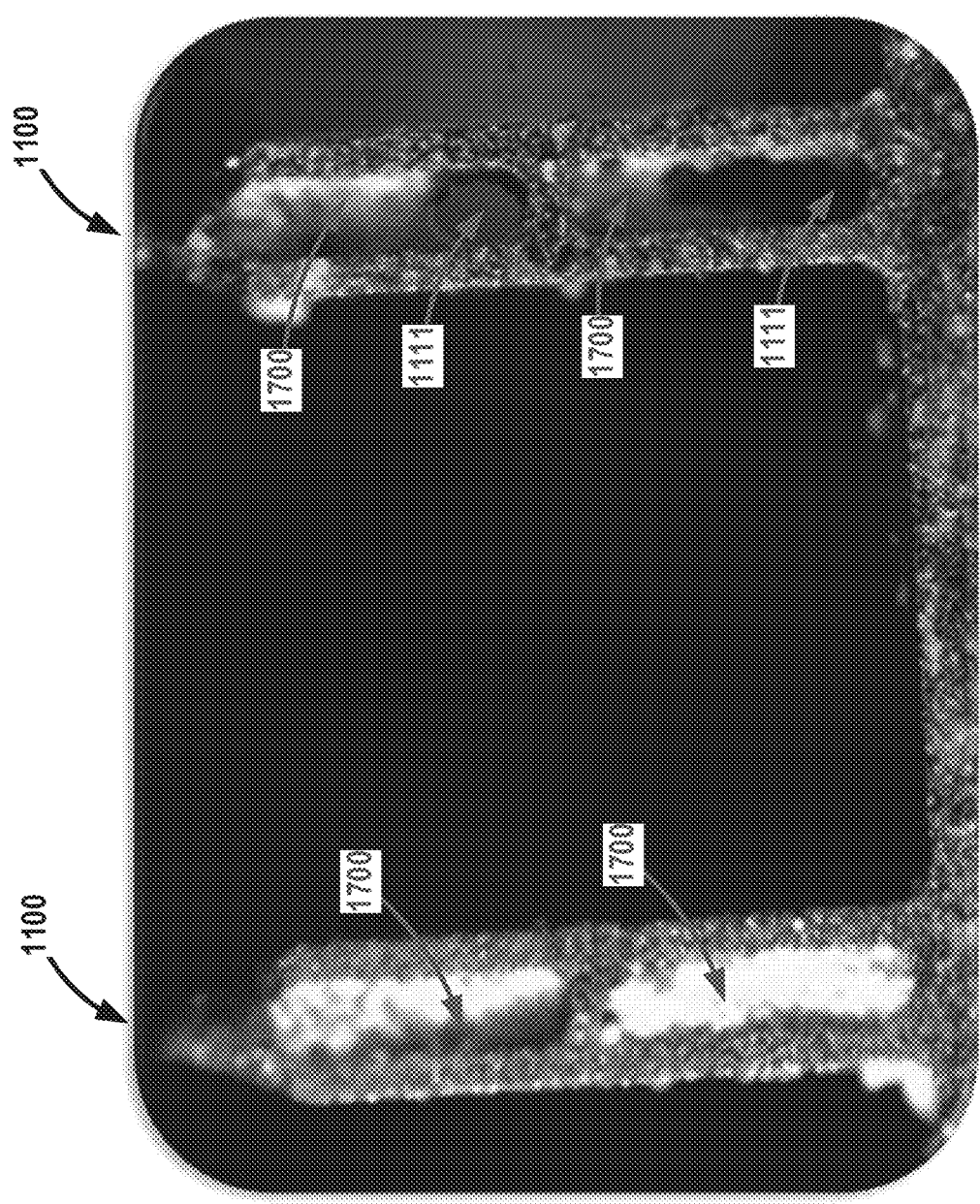
FIG. 18 demonstrates a single line applicator, according to some embodiments of the invention, after removal from the piece of human facial skin, after 3 hours of incubation.
Figures 19A, 19B:
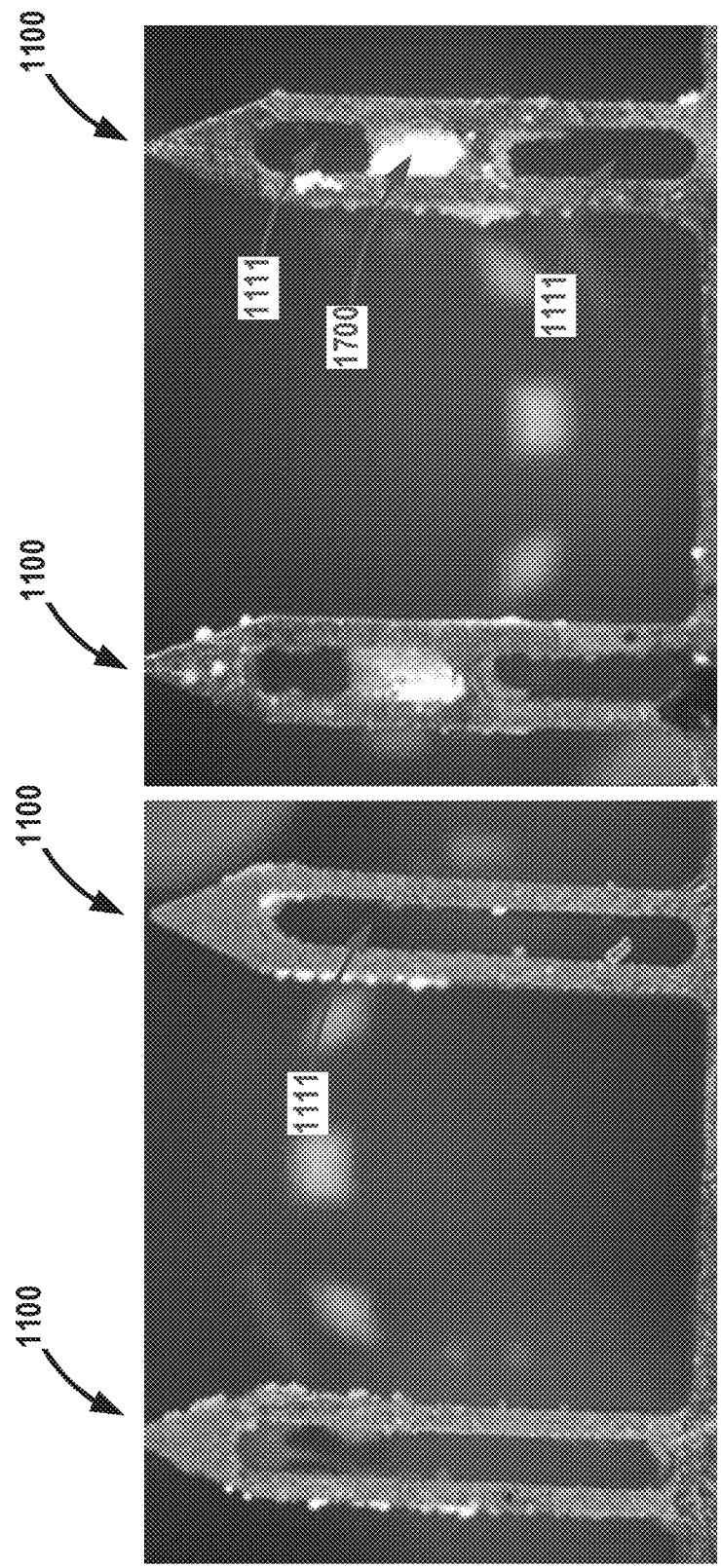
FIGS. 19A and 19B demonstrate the single line applicator, according to some embodiments of the invention, after removal from the piece of human facial skin, after 24 hours of incubation.
Figure 20:
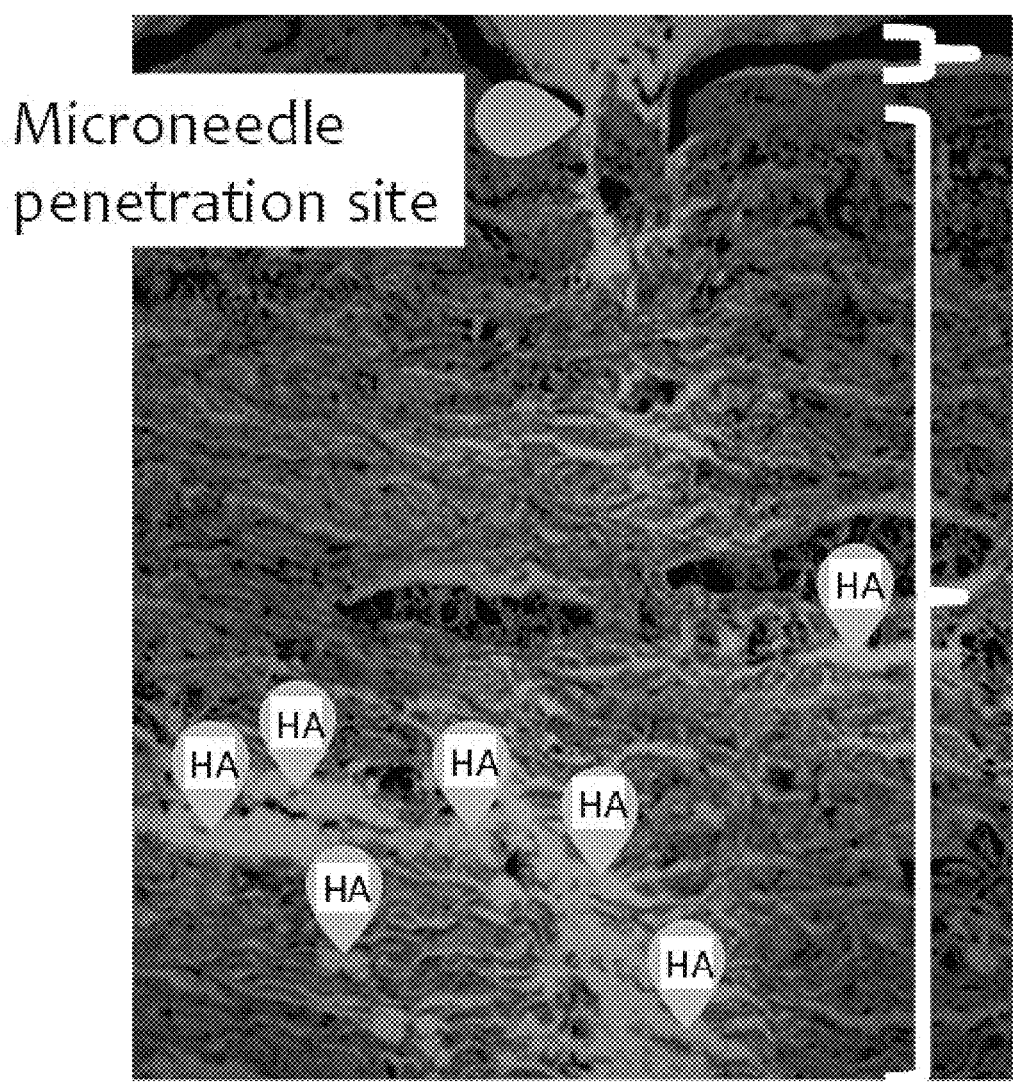
FIG. 20 demonstrates a histological examination of a piece of human facial skin after the removal of the single line applicator, according to some embodiments of the invention, showing Calcium hydroxylapatite (CaHA) spheres in the dermis layer.

METHOD: Experiments were conducted on extra-skins 1800 (shown in for example in FIGS. 8A-8B) that have been removed during face-lift procedures, less than 24 hours from surgery. The microneedles of the present invention were filled 1700 with a mixture of HA spheres having a diameter of 15 to 63 µm and PEG 12000 (demonstrated in FIGS. 15A and 15B). In order to simulate real-life procedures, skins were first intradermally treated with an anesthetic solution 1810, which included saline and lidocaine solution (1%) (demonstrated in FIGS. 16A and 16B). Then, an applicator 1200, according to some embodiments of the present invention, was attached to the skins for inserting the microneedles into the skin-piece 1800 (demonstrated in FIGS. 17A-17B. After incubation of 3 hours, and after incubation of 24 hours, at 37° C. and at 88% humidity, as demonstrated in FIG. 17B, the applicator and microneedles were retracted. RESULTS: FIG. 18 demonstrates the microneedles retracted after 3 hours (in this case microneedles 1100 had two cavities 1111). FIG. 19A demonstrates the microneedles 1100 with a single cavity 1111 retracted after 24 hours, and FIG. 19B demonstrates the microneedles 1100 with two cavities 1111 retracted after 24 hours. As shown, with an optical microscope, almost all of the skin augmentation composition was dispersed from the microneedles. FIG. 20 demonstrates that the skin augmentation composition having hydroxyapatite spheres (HA) was successfully delivered to the middle and deep dermal layers.

Example 14

Figure 21A:
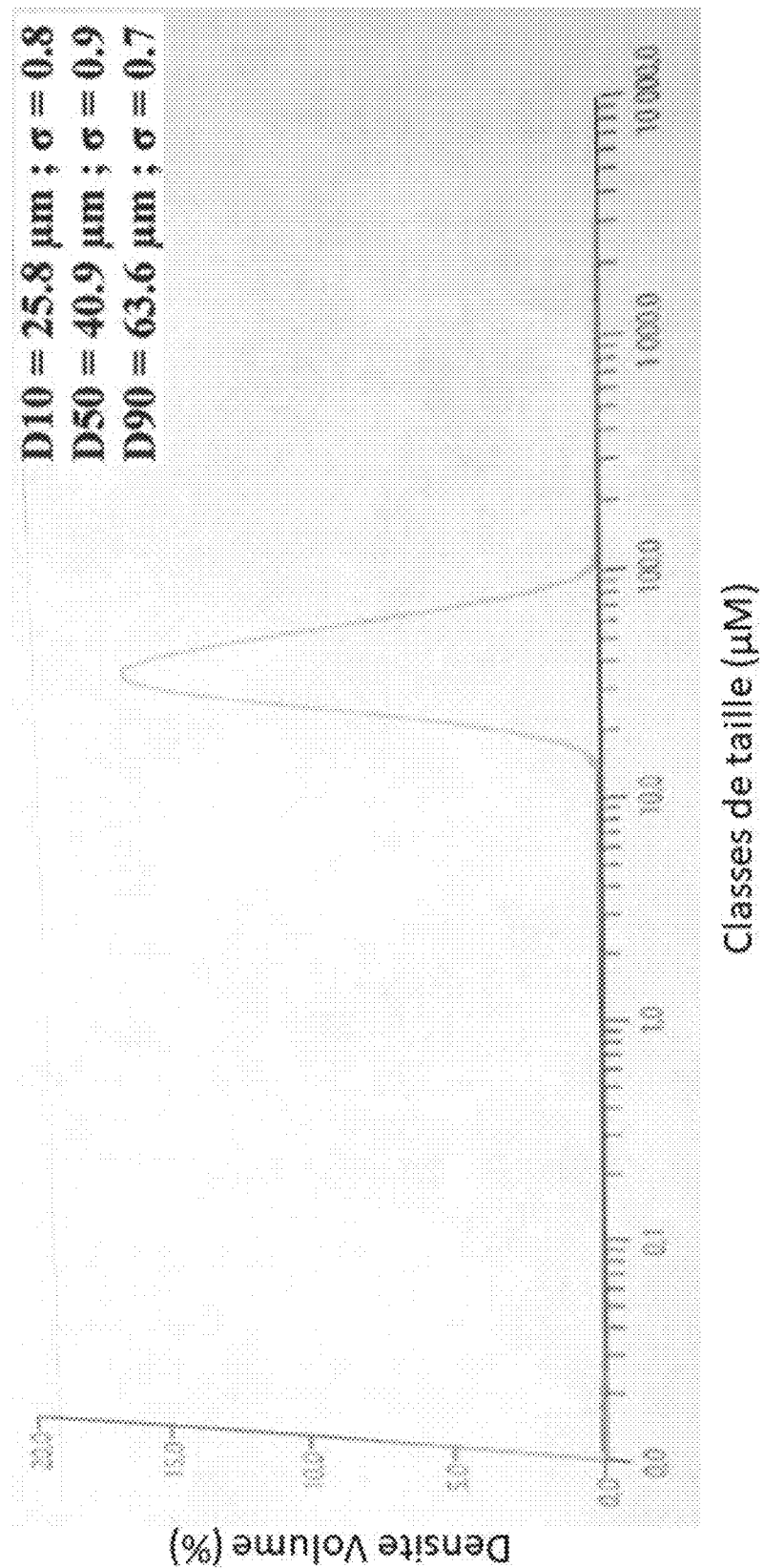
FIG. 21A shows a representative size distribution of Calcium hydroxylapatite (CaHA spheres.
Figure 21B:
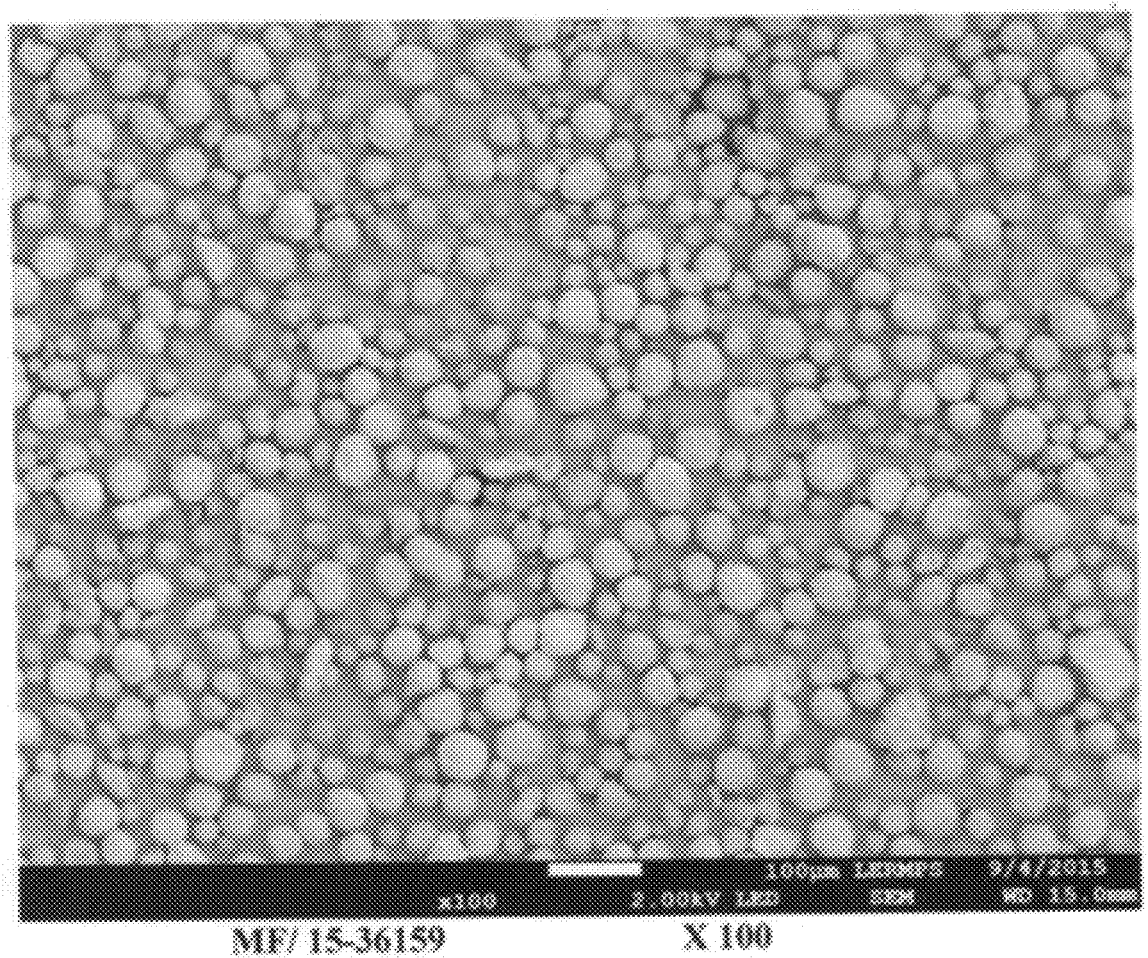
FIG. 21B shows a representative picture of Calcium hydroxylapatite (CaHA) spheres.

Laboratory tests of the hydroxyapatite particles/spheres, used in the experiments above, revealed that about 10% of the particles were up to about 26 Nm in diameter, that about 50% of the particles were up to about 41 µm in diameter, and that about 90% of the particles were up to about 64 µm in diameter. The size distribution of the hydroxyapatite particles/spheres, used in the experiments above (as determined by laser), is provided in FIG. 21A. A picture of the hydroxyapatite particles/spheres, used in the experiments above, is provided in FIG. 21B.

Example 15

Figure 22A:
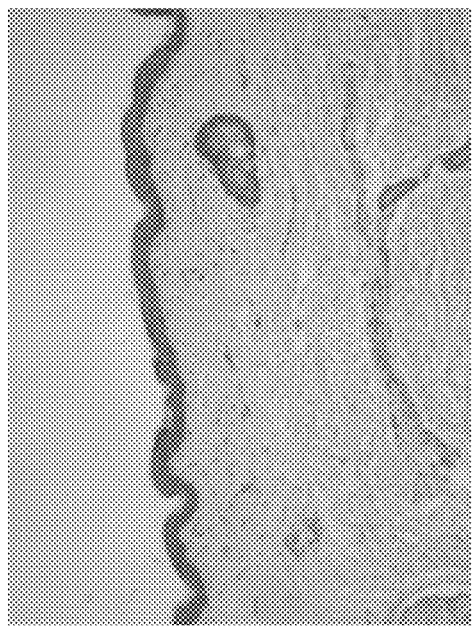
FIGS. 22A and 22B demonstrates another histological examination of pieces of human facial skin, FIG. 22A demonstrates a non-treated piece of skin, while FIG. 22B demonstrates a treated piece of skin, after the removal of the single line, according to some embodiments of the invention, with calcium hydroxylapatite (CHA) spheres in the dermis layer.
Figure 22B:
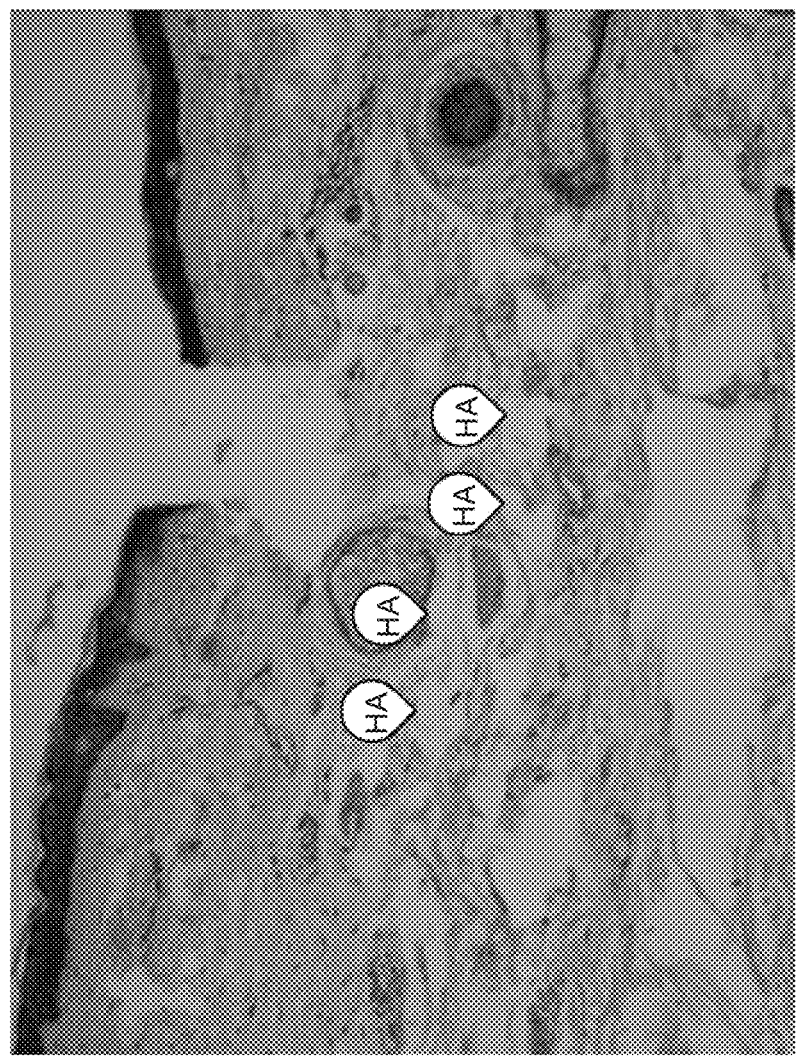

METHOD: Experiments were conducted on extra-skins that have been removed during face-lift procedures. First, the skin pieces were injected with lidocaine and water for injection. Then, microneedles were filled with RADIESSE® which comprises: calcium hydroxylapatite (CaHA) microspheres having a diameter of 25-45 µm, mixed with glycerin, carboxymethylcellulose and sterile water. Then the microneedles were applied into the skin pieces. RESULTS: FIG. 22A demonstrates a non-treated piece of skin. After 15 minutes from microneedles insertion, a translocation of the filler-compound from the microneedles to the dermis was observed. After 30 minutes, most of the filler-compound moved from the microneedles to the dermis. FIG. 22B demonstrates that the skin augmentation composition having hydroxyapatite spheres (HA) was successfully delivered to the middle and deep dermal layers.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A microneedle configured for administration of a biocompatible medical composition to a dermis layer and/or hypodermis layer of a subject, the microneedle comprising:
    a rigid rod section having a constant circumference along its length and having at least one cavity which is open along its length, the cavity is configured to temporarily accommodate a biocompatible medical composition there-within;
    a rigid sharp tip section, at one end of the rod section, configured to allow penetration of at least a part of the rod section to a dermis layer and/or hypodermis layer of a subject;
    a rigid base section, at the second end of the rod section, comprising a length of at least 30 µm;
    wherein the sharp tip section and the base section are configured to be devoid of the biocompatible medical composition; and wherein the at least one cavity comprises the biocompatible medical composition, and wherein the biocompatible medical composition or at least part of the biocompatible medical composition is solid and/or semi-solid at room temperature and is configured to be released from the cavity/ies to the dermis and/or hypodermis upon contact with liquid in the dermis layer and/or hypodermis layer.

2. The microneedle of claim 1, wherein a shape of a cross-section area of the rod section, the tip section and the base section is selected from: rectangular, triangular, circular, oval, polygonal, and any combination thereof.

3. The microneedle of claim 1, wherein at least one of the following holds true:
the biocompatible medical composition is configured to at least partially separate from the cavities and the microneedle, when in dermis and/or hypodermis environment;
the biocompatible medical composition comprises at least one of:
at least one of: skin augmenting material, botulinum material, medical pigment material, steroids, and any combination thereof;
at least one dispersant material, configured to disperse the at least one of: skin augmenting material, botulinum material, medical pigment material, steroids, and any combination thereof, upon contact with the dermis layer and/or the hypodermis layer; and
at least one dispersant material, configured to promote diffusion and/or solubility and/or dispersion in water and/or water solution, and is selected from: water-soluble polymer, polyethylene glycol (PEG), polyethylene oxide (PEO), polyoxyethylene (POE), glycerin, carboxymethylcellulose, sterile water, magnesium sulfate, salt, and any combination thereof.

4. The microneedle of claim 1, wherein the base section is connected and/or anchored to a rigid connecting bar and/or a section of a substrate, such that the rod section is about perpendicular to the section of the substrate and/or to the rigid connecting bar.

5. An applicator configured for administration of a biocompatible medical composition to a dermis layer and/or hypodermis layer of a subject, the applicator comprising:
a substrate, configured to be attached to the subject's skin; and
one or more microneedles according to claim 1, connected and/or anchored to the substrate, such that the microneedle/s are about perpendicular to the substrate and such that the microneedle/s are configured to penetrate the dermis layer and/or hypodermis layer when the substrate is attached to the subject's skin.

6. The applicator of claim 5, wherein at least one of the following holds true:
at least a part of the substrate is at least partially transparent;
at least a part of the substrate is not transparent;
the substrate comprises markings on a surface of the substrate, which is opposite to the surface of the connected and/or anchored microneedle/s, the markings configured to assist a care giver with the application of the microneedle/s;
the substrate is: rigid, at least partially flexible, or flexible;
the substrate comprises an adhesive material, configured to attach at least a part of the substrate to the subject's skin;
the substrate comprises a form of at least one strip or at least one patch;
the microneedle/s are connected and/or anchored and arranged in a form selected from the group consisting of: at least one row, at least one array, at least two segments, and any combination thereof;
for the case of more than one microneedle, the microneedles comprise at least one of: various lengths for the different rod sections, various lengths for the different base sections, various lengths for the different tip sections, and any combination thereof.

7. A method for administrating of a biocompatible medical composition to a dermis and/or hypodermis of a subject; the method comprising:
providing one or more microneedles according to claim 1;
inserting the microneedle/s to the dermis layer and/or hypodermis layer of a subject; and
retracting the microneedle/s from the dermis layer and/or hypodermis layer of the subject, after a predetermined time period.

8. The method of claim 7, further comprising a step of injecting water solution or water for injection or saline, with or without an anesthetic material to a treated area, about 1 minute to about 30 minutes, prior to the insertion of the microneedle/s.

9. The method of claim 7, wherein the step of inserting is provided via attaching an applicator to the skin of the subject; and wherein the step of retracting comprises a retraction of the applicator.

10. The method of claim 7, further comprises providing the biocompatible medical composition with:
at least one of: skin augmenting material, botulinum material, medical pigment material, steroids, and any combination thereof; and
at least one dispersant material, configured to disperse the at least one of: skin augmenting material, botulinum material, steroids, and medical pigment material, upon contact with the dermis layer and/or the hypodermis layer.

11. The method of claim 10, wherein the dispersant material is configured to promote dispersion, diffusion and/or solubility in water or water solution, and is selected from: water-soluble polymer, polyethylene glycol (PEG), polyethylene oxide (PEO), polyoxyethylene (POE), glycerin, carboxymethylcellulose, sterile water, magnesium sulfate, salt, and any combination thereof.

12. A method for manufacturing the applicator according to claim 5, the method comprising:
cutting and/or carving at least one applicator from a sheet of a rigid material; and
spreading the biocompatible medical composition onto the of the rod section, such that cavity/ies are filled.

13. The method of claim 12, in a case of cutting or carving the at least one applicator out of the sheet, further comprising a step of returning the cut/carved applicator/s back to the sheet before spreading the composition, and removing the cut/carved applicator/s out again after the spreading step.

14. The method of claim 12, further comprising a step of removing any excessive composition from at least one of: the substrate, the tip section, the base section, and an outer surface of the rigid rod, while leaving the composition within the cavity/ies.

15. The method of claim 12, further comprising a step of providing the biocompatible medical composition with:
at least one of: skin augmenting material, botulinum material, medical pigment material, steroids, and any combination thereof; and
at least one dispersant material in a frozen state, configured to disperse by melting while in the tissue, at least one of the: skin augmenting material, botulinum material, steroids, and medical pigment material, upon contact with the dermis layer and/or the hypodermis layer.

16. The method of claim 12, further comprising a step of connecting together at least two applicators each having a single row of microneedles, to provide an applicator with multiple rows of microneedles.

17. The method of claim 12, further comprising a step of selecting the rigid material for manufacturing the at least one applicator from a group consisting of: metal, plastic, polymeric, a ceramic material, a silicone, and an absorbable material configured to be absorbed in the dermis layer or hypodermis layer or in both dermis layer and hypodermis.

* * * * *